US009526760B2

(12) United States Patent
Kompella et al.

(10) Patent No.: US 9,526,760 B2
(45) Date of Patent: Dec. 27, 2016

(54) LEDGF PEPTIDES AND FORMULATIONS THEREOF FOR TREATMENT OF DEGENERATIVE DISORDERS

(71) Applicant: The Regents of the University of Colorado, a body corporate, Denver, CO (US)

(72) Inventors: Uday B. Kompella, Aurora, CO (US); Rinku Baid, Aurora, CO (US); Arun K. Upadhyay, Aurora, CO (US); Sarath Yandrapu, Christianburg, VA (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 47 days.

(21) Appl. No.: 14/402,426

(22) PCT Filed: May 21, 2013

(86) PCT No.: PCT/US2013/042074
§ 371 (c)(1),
(2) Date: Nov. 20, 2014

(87) PCT Pub. No.: WO2013/177198
PCT Pub. Date: Nov. 28, 2013

(65) Prior Publication Data
US 2015/0147404 A1 May 28, 2015

Related U.S. Application Data

(60) Provisional application No. 61/649,847, filed on May 21, 2012.

(30) Foreign Application Priority Data

Nov. 16, 2012 (WO) ................ PCT/US2012/065620

(51) Int. Cl.
*A61K 38/18* (2006.01)
*C07K 14/475* (2006.01)
*A61K 47/48* (2006.01)
*A61K 38/00* (2006.01)

(52) U.S. Cl.
CPC ......... *A61K 38/18* (2013.01); *A61K 47/48015* (2013.01); *A61K 47/48884* (2013.01); *C07K 14/475* (2013.01); *A61K 38/00* (2013.01)

(58) Field of Classification Search
CPC .................................................. A61K 38/18
See application file for complete search history.

(56) References Cited

U.S. PATENT DOCUMENTS 4,221,787 A 9/1980 Bodor et al.
4,469,689 A 9/1984 Anderson et al.

6,750,052 B1 6/2004 Shinohara et al.
7,514,233 B2 4/2009 Debyser et al.
7,708,915 B2 5/2010 Castor
7,820,195 B2 10/2010 Kauper et al.
2010/0056488 A1 3/2010 Teicher et al.
2012/0028889 A1 2/2012 Debyser et al.

FOREIGN PATENT DOCUMENTS

EA          013931        8/2010
WO   WO 2007/011875     1/2007
WO   WO 2008/053478     5/2008

OTHER PUBLICATIONS

Shinohara et al., 2002, LEDGF, a survival factor, activates stress-related genes, Progress in Retinal and Eye Research, 21: 341-358.*
Baid et al., "Biosynthesis, characterization, and efficacy in retinal degenerative diseases of lens epithelium-derived growth factor fragment (LEDGF$_{1-326}$), a novel therapeutic protein", Journal of Biological Chemistry, 228(24): 17372-17383, 2013.
Extended European Search Report issued in European Application No. 13794410.4, dated Feb. 19, 2016.
Holz and Miller, "[Pharmacological therapy for age-related macular degeneration. Current developments and perspectives]", Ophthalmologe, 100(2): 97-103, 2003. English Abstract.
Shinohara et al., "LEDGF, a survival factor, activates stress-related genes", Progress in Retinal and Eye Research, 21(3): 341-358, 2002.
Baid et al., "LEDGF$_{1-326}$ decreases P23H and wild type rhodopsin aggregates and P23H rhodopsin mediated cell damage in human retinal pigment epithelial cells", PLoS One, 6(9):e24616, 2011.
Dryja et al., "A point mutation of the rhodopsin gene in one form of retinitis pigmentosa", Nature, 1990. 343(6256): 364-6.
Hartong, et al., "Retinitis pigmentosa", Lancet, 2006. 368(9549): p. 1795-809.
International Preliminary Report on Patentability issued in International Application No. PCT/US2013/042074, issued Nov. 25, 2014.
International Preliminary Report on Patentability issued in International Application No. PCT/US2012/065620, issued May 20, 2014.
International Search Report and Written Opinion issued in International Application No. PCT/US2013/042074, mailed Oct. 21, 2013.
International Search Report and Written Opinion issued in International Application No. PCT/US2012/065620, mailed Mar. 15, 2013.
Jung et al., "Prednisolone 21-sulfate sodium: a colon-specific prodrug of prednisolone", Journal of Pharmacy and Pharmacology, 55: 1075-1082, 2003.
Ohguro, H., et al., "[Molecular pathology of retinitis pigmentosa]", Nihon Ganka Gakkai Zasshi, 2002. 106(8): 461-73. (English Abstract).
Pakula et al., "Genetic analysis of protein stability and function",*Anna Rev Genet.*, 23: 289-310, 1989.
Tokuriki et al., "Stability effects of mutations and protein evolvability",*Curr Opin Struct Biol.*, 19(5): 596-604, 2009.

* cited by examiner

Primary Examiner — Amber D Steele
(74) Attorney, Agent, or Firm — Parker Highlander PLLC

(57) ABSTRACT

LEDGF peptides with anti-protein aggregation activity and methods of use are provided. The LEDGF peptides disclosed herein demonstrate an ability to treat degenerative diseases and diseases with various cellular stresses including oxidative stress and protein-aggregation stress. In addition, extended release formulations, including formulations suitable for ophthalmic administration are provided.

26 Claims, 31 Drawing Sheets

Additives= 0.1 % Tween 20 + 1 mM EDTA + 10 % Sucrose

LEDGF PEPTIDES AND FORMULATIONS THEREOF FOR TREATMENT OF DEGENERATIVE DISORDERS

RELATED APPLICATIONS

This application is a national phase application under 35 U.S.C. §371 of International Application No. PCT/US2013/042074, filed May 21, 2013, which claims priority to U.S. Provisional Patent Application No. 61/649,847 filed May 21, 2012, and International Patent Application No. PCT/US2012/065620 filed on Nov. 17, 2012. The contents of the above-identified priority applications are hereby fully incorporated herein by reference.

TECHNICAL FIELD

The present invention relates generally to novel peptides of lens epithelium derived grown factor (LEDGF) and compositions thereof for use in treating degenerative diseases and diseases with various cellular stresses including oxidative stress and protein-aggregation stress. More specifically, the present inventions relates to novel formulations of $LEDGF_{1-326}$ with enhanced stability and sustained delivery profiles and their use in treating protein aggregation-mediated diseases, age-related diseases, and degenerative diseases.

BACKGROUND

Diseases of the posterior segment of eye which includes age related macular degeneration (AMD) and retinitis pigmentosa (RP) are the leading cause of blindness in United States. (Jager et al., N ENGL J MED, 2008. 358(24): 2606-17). Currently, about 8 million individuals are suffering from AMD in the United States and by 2020 this number is expected to reach 12 million. (Jager et al.; Friedman et al. Arch Ophthalmol, 2004. 122(4): p. 564-72). Dry form of AMD (Dry AMD) associated with chronic oxidative stress and inflammation accounts for 90% of AMD cases. (Libby et al. Adv Exp Med Biol, 2010. 664: p. 403-9; Stuen. Generations, 2003. 27: p. 8-14). On the other hand RP is a genetically inherited disease caused by more than 50 different gene mutations. (Ohguro, H., et al., Nihon Ganka Gakkai Zasshi, 2002. 106(8): p. 461-73; Dryja, et al., Nature, 1990. 343(6256): p. 364-6.) Around 1.5 million people worldwide currently suffer from RP. (Hartong, et al., Lancet, 2006. 368(9549): p. 1795-809).

The unique anatomy and physiology of the eye is a major hurdle in the advancement of drug therapeutic for the back of the eye including retinal degenerative diseases. (Kompella et al., Ther Deliv. 1(3): p. 435-56). Topical routes of administration are inefficient in delivering drugs to the back of the eye because of the presence of various static barriers (cornea, conjunctiva, and sclera among others tissues) and dynamic barriers (blinking, tear film, tear turn over, and induced lacrymation). (Gaudana, R., et al., *Ocular drug delivery*. Aaps J, 2010. 12(3): p. 348-60; Thrimawithana et al. Drug Discov Today, 2011. 16(5-6): p. 270-7). On the other hand blood retinal barrier (BRB), systemic degradation, systemic side effects, and low concentrations at target site are major challenges for the intravenous route. Other routes such as intra cameral, periocular, subretinal have their own subset of problems sharing some issues in common with topical and systemic route of administration (Baid et al. Drug Development and the back of the eye. ed. Kompella UB. 2010, p. 409-448: Springer). Local delivery such as an intravitreal injection places the drug to close proximity to the retina (the target tissue for retinal degenerative diseases) and thus is the most effective route in delivering drug to retina. However, frequent intravitreal injections of the drug leads to various complications such as retinal detachment, retinal hemorrhage, endopthalmitis, increased intraocular pressure, and not to mention patient compliance and infections. (Peyman et al. Retina, 2009. 29(7): p. 875-912; Wu et al. Semin Ophthalmol, 2009. 24(2): p. 100-5). Thus there is a need of for compositions and delivery system that can extend the retention of drugs in the eye.

Novel drug delivery systems have gained major attention which could sustain or control the release of drug for extended period of time as well as increase the stability and bioavailability of therapeutic agents such as proteins, genes and other small molecules. Biodegradable (PLGA, PCL) and non-biodegradable (e.g Vitraset and Retisert) implants provides a platform for sustaining release of drug over several months to years. However, erratic drug release profile for biodegradable implants and requirement of highly invasive eye surgery are few drawbacks. Micro and nanoparticles provide sustained release of encapsulated molecules for weeks to months. However, use of organic solvents such as dichloromethane during preparation denatures and reduces protein efficacy leading to non-effective treatment. Further encapsulation efficiency, controlled particles size, and sterility during preparations are among the other hurdles. Iontophoresis, microneedles, ultrasound based ocular deliver have also been tried, however, the major advances are with the small molecule drugs and still are in investigation stage and needs validations to establish their efficacy and safety. Thus non- or minimally-invasive, controlled, and sustained delivery to the posterior segment is becoming extremely vital with escalating advances in the emerging therapies for retinal degenerations.

SUMMARY

The present invention is directed to biologically active peptides of LEDGF that can be produced in high quantity, purity, or both. For example, the present invention is directed to peptides of LEDGF that can be produced at, or greater than, 20 mg per liter of culture and at, or greater than, 90% purity as quantified by SDS-PAGE and SEC-HPLC. In one exemplary embodiment the peptide is approximately a 40 kDa monomer, that may exist as an 80 kDa dimer. In another exemplary embodiment, the peptide has primarily a random coil structure and includes an N-terminal stress related binding domain, and optionally a TAT binding domain.

In another exemplary embodiment, the peptide comprises amino acids 1-326 of LEDGF ($LEDGF_{1-326}$). In yet another exemplary embodiment, the peptide comprises SEQ ID NO: 2. In another exemplary embodiment, the peptide comprises an amino acid sequence with at least 70%, at least 75%, at least 80%, at least 85%, at least 90%, or at least 95% sequence identity with SEQ ID NO: 2. In addition, the present invention includes nucleic acid sequences encoding SEQ ID NO: 2, or nucleic acid sequences encoding amino acid sequences having at least 70%, at least 75%, at least 80%, at least 85%, at least 90%, or at least 95% sequence identity with SEQ ID NO: 2. The present invention further includes vectors containing such nucleic acid sequences. In one exemplary embodiment, the vector is a pET-28a(+) vector.

In another aspect, the present invention comprises compositions containing the LEDGF peptides. In one exemplary embodiment, the composition comprises the LEDGF peptide in combination with a pharmaceutical carrier, diluent, excipient, or combination thereof. In another exemplary embodiment, the composition comprises the LEDGF peptide associated with or bound to colloidal metal particles, such as zinc, to form nano-assemblies. In yet another exemplary embodiment, the compositions comprise the LEDGF peptide encapsulated or bound to an inner particle loaded into a porous outer particle. In certain exemplary embodiments, the LEDGF peptide used in the above compositions is $LEDGF_{1-326}$.

In another aspect, the present invention is directed to methods of treating protein aggregation-mediated diseases by administering the above LEDGF peptide compositions to a patient in need thereof. In certain exemplary embodiments, the protein aggregation-mediated disease is a retinal degeneration disease. Exemplary retinal degeneration diseases include, but are not limited to, age related macular degeneration (AMD) retinitis pigmentosa (RP) and diabetic retinopathy (DR). In another exemplary embodiment, the protein aggregation-mediated diseases are neurodegenerative diseases including, but not limited to, Alzheimer's disease (AD), Parkinson's disease (PD), Huntington's disease (HD), amyotrophic lateral sclerosis, or a prion disease.

DETAILED DESCRIPTION

Definitions

Figure 1:
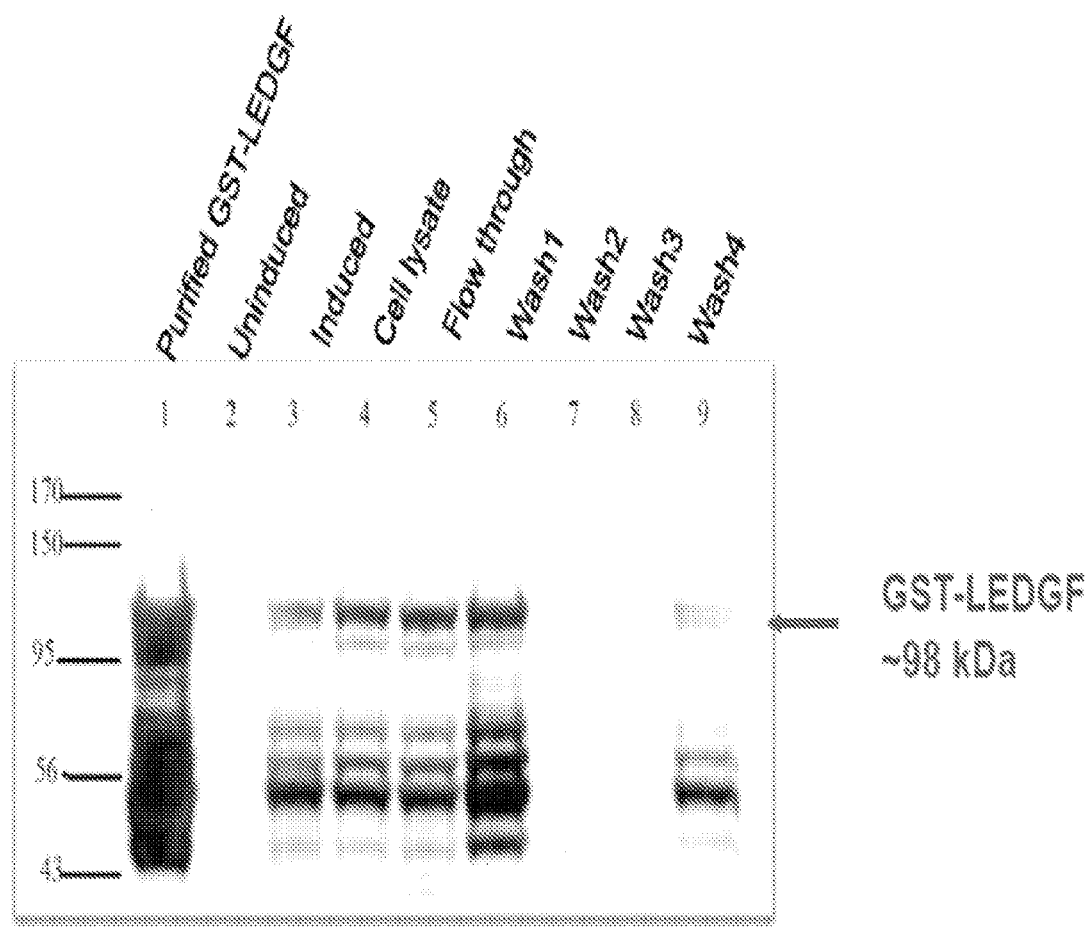
FIG. 1 is an immunoblot of purified full-length LEDGF indicating that attempts to purify full length LEDGF result in an unstable and fragmented product.
Figure 2:
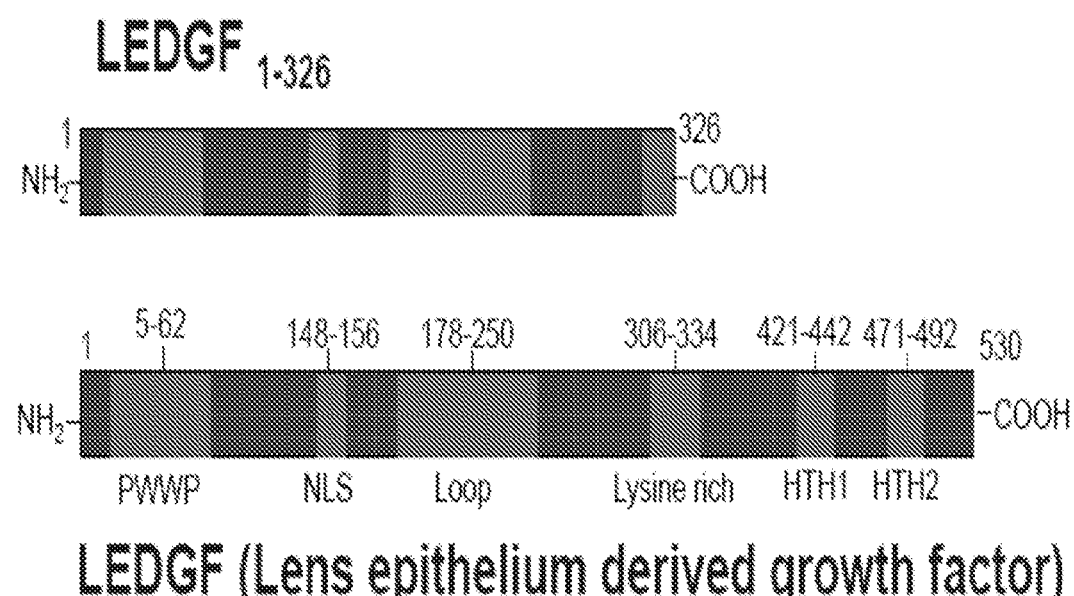
FIG. 2 is a diagram comparing full length LEDGF to $LEDGF_{1-326}$.

As used herein "retina and retinal" refers both to the retina as well as the general posterior segment of the eye adjacent to the retina.

As used herein "treating or treatment" refers to a complete reversal or elimination of the underlying disease, a temporary or sustained prevention of disease progression, a temporary or sustained regression of the disease, and amelioration of one or more symptoms associated with the disease.

The terms "peptide," "polypeptide" and "protein" are used interchangeably herein. Unless otherwise noted, the terms refer to a polymer having at least two amino acids linked through peptide bounds. The terms thus include oligopeptides, protein fragments, analogs, derivatives, glycosylated derivatives, pegylated derivatives, fusion proteins and the like.

As used herein, "sequence identity/similarity" refers to the identity of, or similarity of two or more amino acid sequences. Sequence identity can be measured in terms of percentage identity, the higher the percentage, the more identical the sequences are. Methods of alignment and sequences for comparison are well known in the art. Various programs and alignment algorithms are described in: Smith & Waterman, *Adv. Appl. Math.* 2:482, 1981; Needleman & Wunsch, *J. Mol. Biol.* 48:443; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al. *Nuc. Acids. Res.* 16:10881-10, 1990, present detailed consideration of sequence alignment methods and homology calculations.

The NCBI Basic Local Alignment Research Tool (BLAST) (Altschule et l al. *J. Mol. Biol.* 215:403-10, 1990) is available from several sources, including the National Center for Biological Information (NCBI, National Library of Medicine, Building 38A, Room 8N805, Bethesda, Md. 20894) and on the internet, for use in connection with the sequence analysis programs blastp, blastn, blastx, tblastn, and tblastx. Blastp is used to compare amino acid sequences. Additional information can be found at the NCBI web site.

In general, once aligned, the number of matches is determined by counting the number of positions where an identical amino acid residue is present in both sequences. The percent identity is determined by dividing the number of matches either by the length of the sequence set forth in the identified sequences, or by an articulated length (such as 100 consecutive nucleotides or amino acids residues from a sequence set forth in an identified sequence), followed by multiplying the resulting value by 100.

INTRODUCTION

Full length LEDGF has the ability to rescue retinal pigment epithelial cells from P23H mutant rhodopsin aggregation induced stress (Baid et al., PLoS One. 6(9): p. e24616). However, the use of therapeutic peptides is challenging due to the need of the protein to maintain a specific three-dimensional structure in order to remain biologically active. In addition, production and biosynthesis often fail because of a lack of protein stability throughout the biosynthesis and purification process. Further, in order to use protein therapeutics effectively, it is often necessary to achieve production of several milligrams in order to characterize the proteins properties effectively. For example, full length LEDGF yields only 0.9 mg per 500 ml, well short of the tens of milligrams needed to properly characterize the protein, and results in a fragmented product.

The present invention provides peptides of LEDGF that maintain the full-length protein's cell surviving activity while allowing production and purification of LEDGF peptides in high quantity and purity. Further, the LEDGF peptides of the present invention have anti-protein aggregation activity. The LEDGF peptides of the present invention demonstrate an ability to treat degenerative diseases and diseases associated with various cellular stresses including oxidative stress and protein-aggregation stress. Accordingly, a molecule like the LEDGF peptides of the present invention may represent a universal therapeutic protein for treating multiple protein-aggregation mediated diseases, including other retinal degenerative and neurodegenerative diseases. The present invention further comprises extended release formulations of the LEDGF peptides useful in treating the above diseases.

LEDGF Peptides

The LEDGF peptides of the present invention contain N-terminal peptides of full-length LEDGF. In one exemplary embodiment, the LEDGF peptide comprises the LEDGF N-terminal stress related binding domain. While not limited by the following theory, LEDGF's ability to function as a transcription factor and initiate transcription of other stress response genes may contribute to LEDGF peptide's ability to protect against protein aggregation-mediated diseases. Alternatively, LEDGF peptides may bind to mis-folded proteins, either directly or through other intermediary proteins, and facilitate normal folding, or ubiquitnation of mis-folded proteins to ensure proteolytic degradation. In certain exemplary embodiments, the LEDGF peptide may further comprise a TAT binding domain.

In one exemplary embodiment, the LEDGF peptide is $LEDGF_{1-326}$ (SEQ ID NO: 2). $LEDGF_{1-326}$ was purified to near homogeneity. $LEDGF_{1-326}$ has a primarily random coiled structure, is stable at room temperature, and exists as a 40 kDa monomer and/or 80 kDa dimer. As described in further detail in the Examples section below, $LEDGF_{1-326}$ was able to prevent P23H mutant rhodopsin mediated aggregation stress in ARPE-19 cells. Single intravitreal injection of $LEDGF_{1-326}$ reduced the functional loss of photoreceptors in retinal degenerative rat model for over eight weeks.

LEDGF peptides of the present invention also include LEDGF peptides having at least about 70%, at least about 75%, at least about 80%, at least about 85%, at least about 90%, or at least about 95% sequence identity with $LEDGF_{1-326}$. In one exemplary embodiment, LEDGF peptides include peptides encompassing the N-terminal stress related binding domain of full-length LEDGF and at least about 70%, at least about 75%, at least about 80%, at least about 85%, at least about 90%, or at least about 95% sequence identity with $LEDGF_{1-326}$. In another exemplary embodiment, LEDGF peptides include peptides with the N-terminal stress related binding domain and a TAT binding domain and at least about 70%, at least about 75%, at least about 80%, at least about 85%, at least about 90%, or at least about 95% sequence identity with $LEDGF_{1-326}$. Further, the present invention includes peptides encompassing more than or less than the 326 amino acids of SEQ ID NO: 2, wherein the larger or smaller peptides do not result in a significant decrease in LEDGF biological activity or stability during biosynthesis and purification. The suitability of an LEDGF peptide for use with the present invention can be determined by one of ordinary skill in the art by assessing the putative peptide's similarity to the biophysical and biochemical properties and biological activity using the assays described in the Examples section below. One of ordinary skill can predictably recognize that LEDGF peptides with similar biophysical properties, biochemical properties, and biological activity to $LEDGF_{1-326}$ will have similar utility and accordingly fall within the scope of the present invention.

In certain example embodiments, the LEDGF peptides described above are made synthetically. In certain other example embodiments, the LEDGF peptides described above are made recombinantly. Host suitable for expression of the LEDGF peptides include, but are not limited to, *E. coli, Saccharomces, Picchia, Bacillus*, CHO, BHK, COS, and NSO cells.

Standard Pharmaceutical Formulations

The LEDGF peptides described herein can be provided as physiologically acceptable formulations using known techniques. *Remington's Pharmaceutical Sciences*, by E. W. Martin, Mack Publishing Co., Easton, Pa., 19th Edition (1995), describes compositions and formulations suitable for pharmaceutical delivery of LEDGF peptides disclosed herein.

The formulations in accordance with the present invention can be administered in the form of a tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, an implant, in a device, as an eye drop or a transdermal patch.

The formulations include those suitable for oral, rectal, nasal, inhalation, topical (including dermal, transdermal, buccal, and eye drops), vaginal, parenteral (including subcutaneous, intramuscular, intravenous, intradermal, intraocular, intratracheal, and epidural), ophthalmic (periocular, intraocular, including suprachoroidal, subretinal, and intravitreal), or inhalation administration. In one exemplary embodiment, the peptides of the present invention are formulated for transcleral, suprachoroidal, subretinal, or intravitreal delivery. Transcleral delivery includes subconjunctival, subtenons', and retrobulbar transcleral delivery. The formulations can conveniently be presented in unit dosage form and can be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored base, usually sucrose and acacia or tragacanth; pastilles comprising the active ingredient in an inert base such as gelatin and glycerin, or sucrose and acacia; and mouthwashes comprising the ingredient to be administered in a suitable liquid carrier.

Formulations suitable for topical administration to the skin may be presented as ointments, creams, gels, pastes, and eye drops comprising the ingredient to be administered in a pharmaceutical acceptable carrier.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken; i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; gels; and surgically placed implants.

Nanoassembly Formulations

In certain exemplary embodiments, the LEDGF peptides of the present invention may be delivered as nanoparticle assemblies by binding or otherwise associating the LEDGF peptides with colloidal metal particles. Any colloidal metal can be used in the present invention. Colloidal metals include any water-insoluble metal particle, metallic compound dispersed in liquid water, a hydrosol, or a metal sol. The colloidal metal particle may be selected from the metals in groups IA, IB, IIB, and IIIB of the periodic table, as well as the transition metals, especially those of group VIII. Exemplary metals include zinc, gold, silver, aluminum, ruthenium, iron, nickel, and calcium. Other suitable metals include the following in all of their various oxidation states; lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium.

The metals are preferably derived from the appropriate metal compound in ionic form, for example $Al^{3+}$, $Ru^{3+}$, $Zn^{2+}$, $Fe^{3+}$, $Ni^{2+}$, and $Ca^{2+}$.

In one exemplary embodiment, the nanoparticles are formed by adding the colloidal metal directly to a solution containing the LEDGF peptide. As used herein "nanoparticles" refer to one or more peptides bound or adsorbed to the surface of a single colloidal metal particle, or a peptide bound to or adsorbed to multiple colloidal metal particles. By way of example, LEDGF/Zn nanoparticles are formed by adding Zn(II) in a controlled manner of 10 mM at room temperature. Thereafter the nanoassemblies are allowed to form over 24 hours time period at 37° C. Conditions for formation of other nanoassemblies using other colloidal metals may be readily determined by one of ordinary skill in the art.

Particle-in-Particle Formulations

In another exemplary embodiment, the LEDGF peptides are formulated as particle-in-particle extended release formulations. The extended release compositions of the present invention comprise an inner particle contained within a larger porous outer particle, including various architectures such as a nanoparticle in porous microparticle (NPinPMP), small nanoparticle in porous large nanoparticle (SNPinPLNP), and small microparticle in porous large microparticle (SMPinPLMP). The inner particle is smaller and relatively non-expandable as compared to the larger particle. The outer particle is expandable and forms a significantly porous structure during processing that allows the embedding of the inner particle within the outer particle' porous structure.

As used in the context of the present invention, a particle is considered to expand in the presence of a supercritical fluid if the particle's initial surface area increases within a range of approximately 1.25 to approximately 100 times. In certain exemplary embodiments, the particle is considered to expand if the particle's initial surface area expands within a range of approximately 1.25 to approximately 5 times, approximately 5 to approximately 25 times, approximately 25 to approximately 50 times, approximately 50 to approximately 75 times, or approximately 75 to 100 times. Alternatively, a particle is considered to expand if the particle's initial size increases by at least 5%, 10%, 15%, 20%, 25%, 30%, 35%, 40%, 45%, or 50%.

Inner particles of the present invention are made using polymeric or non-polymeric materials that do not expand in the presence of a supercritical fluid. In certain exemplary embodiments, the nanoparticle material is a polymeric material that will not expand in the presence of supercritical fluids. In certain exemplary embodiments, the polymeric material is a material that will not expand in the presence of supercritical carbon dioxide. Examples of suitable polymeric and non-polymeric materials that may be used in the present invention include polylactide (PLA), poly(glycolic acid), co-polymers of lactic and glycolic acid (PLGA), cellulose derivatives, chitosan, polyethylene (PE), polypropylene, poly(tetrafluoroethylene), poly(ethylene terephathalate), iron oxide, cerium oxide, zinc oxide, gold, silver, other biocompatible metals and crystals, and silica. Crystalline materials or those with large crystalline regions are less likely to expand during supercritical fluid processing. Polymeric inner particles may be prepared using conventional emulsion-solvent evaporation methods or other similarly suitable synthesis method. LEDGF peptides may be encapsulated in the inner particles during formation or loaded on the surface after formation of the inner particles.

Outer particles of the present invention are made using materials that expand in the presence of a supercritical fluid. In certain exemplary embodiments, the microparticle material is a polymeric material that expands in the presence of a supercritical fluid. In certain exemplary embodiments, the material that expands in the presence of supercritical carbon dioxide. Examples of suitable polymeric materials that may be used in the present invention include lactide-co-glycolide, polyamides, polycarbonates, polyakylene glycols, polyalkylene oxides, polyvinyl alcohols, polyvinyl ethers, polyvinyl esters, polyvinylpyrrolidone, polyglycolides, and co-polymers thereof. In addition, suitable polymer materials also include alkyl cellulose, hydroxyalkyl celluloses, cellulose eethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate cellulose acetate butyrate, cellulose acetate phthalate, carboxylethyl cellulose, cellulose poly(methyl methacrylate), poly(elthylmethacrylate), poly(butymethacrylate), poly(vinyl alcohols), poly(vinyl acetate), and polyvinylpryrrolidone. In general, amorphous materials or those with large amorphous regions are suitable for expansion during supercritical fluid processing. Polymeric outer particles may be prepared using conventional emulsion-solvent evaporation, or other similarly suitable synthesis method. In certain exemplary embodiments, LEDGF peptides may be encapsulated in the outer particles during formation or loaded on the surface after formation of the outer particles.

The process of generating various particle architectures is achieved using supercritical fluid flow technology. The resulting organic solvent-free loading is especially well suited to drugs, such as peptide and nucleotide based drugs, which are susceptible to aggregation or degradation. For example, LEDGF peptide may be loaded on the surface of the inner particle, the outer particle or both; in the matrix of the inner particle, outer particle or both; present in the pores of the outer particle; or a combination thereof. In certain exemplary embodiments, LEDGF peptides may be present on the surface of the inner particle. In another exemplary embodiment, LEDGF peptide may be present on the surface of the inner and outer particle. In yet another exemplary embodiment, LEDGF peptides may be present in the matrix of the inner particle. In another exemplary embodiment, LEDGF peptides may be present in the matrix of both the inner and outer particle. In another exemplary embodiment, a therapeutic agent may further be present in the porous structure of the outer particle.

Inner and outer particles are admixed together and exposed to a supercritical fluid under high pressure. In certain exemplary embodiments, the supercritical fluid is carbon dioxide. Upon exposure to the supercritical fluid the outer particles expand to create a porous structure on the outer surface. The supercritical fluid then infuses the inner particles into the outer particles to form particle-in-particle extended release formulations. In one exemplary embodiment, the particle-in-particle extended release formulations comprise the incorporation of inner nanoparticles having a diameter of approximately 1 nm to approximately 900 nm in an outer microparticle having a diameter of approximately 1 μm to approximately 100 μm. In another exemplary embodiment, the particle-in-particle extended release formulations comprise the incorporation of an inner nanoparticle having a diameter of approximately 1 nm to approximately 300 nm in an outer nanoparticle having a diameter of approximately 10 nm to approximately 999 nm. In yet another exemplary embodiment, the particle-in-particle extended release formulations include the incorporation of an inner microparticle having a diameter of approximately 1 μm to approximately 100 μm in an outer microparticle having a diameter of approximately 2 μm to approximately 500 μm. Selection of an appropriate sized inner and outer particle will depend on the type of material comprising the particles, the expansive ability of the outer particle in the supercritical fluid used, and the size of inner particles to be incorporated within the outer particle. These are all factors that can be readily selected for by one of ordinary skill in the art. In general, the size ratio between the inner and outer particle may vary from approximately 1:5 to approximately 1:100. In one exemplary embodiment the size ratio may be 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100

Formation of NPinPMPs may be achieved by exposure of the nanoparticles and microparticles at approximately 1000 psi to approximately 1400 psi. The time of exposure may vary, for example, from approximately 5 minutes to approximately 2 hours. The temperature may range from 30° C. to 45° C. The selection of an appropriate pressure and temperature range are determined primarily by the range of temperature and pressures near the supercritical point for a given supercritical fluid. Accordingly, one of ordinary skill in the art will be able to select the appropriate time, temperature, and pressure ranged based upon the supercritical fluid used, the size or amount of outer particle expansion desired, and the degree of porosity in the outer particle desired. For example, exposure for longer periods of time and/or at higher pressures followed by pressure quench will result in greater expansion and porosity than shorter exposure times and/or pressures.

In one exemplary embodiment, the inner particles and outer particles are mixed at a ratio of approximately 1:3. In one exemplary embodiment, the ratio of inner particles to outer particles used is approximately 1:9. These ratios will influence the extent of nanoparticle incorporation and slow release of the drug. In general, the larger the amount of inner particles relative to outer particles the higher the amount of inner particles incorporated in outer particle, increasing the drug release rates and the dose. The smaller the amount of inner particles relative to the outer particles, the smaller the burst release.

Protein Aggregation-Mediated Diseases and Methods of Treatment

The LEDGF formulations of the present invention may be used to treat protein-aggregation mediated diseases. Protein aggregation-mediated diseases that may be treated with the LEDGF compositions of the present invention include retinal degenerative diseases and neurodegenerative diseases. Retinal degenerative diseases include age related macular degeneration retinitis pigmentosa, and diabetic retinopathy. Neurodegenerative diseases include Alzheimer's disease (AD), Parkinson's disease (PD), Huntington's disease (HD), amyotrophic lateral sclerosis, and prion diseases.

In one exemplary embodiment, the present invention comprises methods of treating a retinal degenerative disease comprising administering to a patient with a retinal degenerative disease a composition comprising a LEDGF peptide of the present invention. In certain exemplary embodiments the LEDGF peptide is SEQ OD NO: 2. In one exemplary embodiment, the LEDGF composition is delivered transclerrally. In another exemplary embodiment, the LEDGF composition is administered to the eye topically in the form of eye drops. In another exemplary embodiment, the LEDGF composition is implanted or systemically administered in an extended release formulation. In one exemplary embodiment, the extended release formulation is a nanoassembly extended release formulation, such as a LEDGF/zinc nanoassembly formulation. In another exemplary embodiment, the extended release formulation is a particle-in-particle formulation, such as a nanoparticle in porous microparticle (NPinPMP) formulation.

In one exemplary embodiment, the present invention comprises methods of reducing protein aggregation in a retinal degenerative disease comprising administering to a patient with a retinal degenerative disease a composition comprising a LEDGF peptide of the present invention. In certain exemplary embodiments the LEDGF peptide is $LEDGF_{1-326}$. In one exemplary embodiment, the LEDGF composition is delivered transclerrally. In another exemplary embodiment, the LEDGF composition is administered to the eye topically in the form of eye drops. In another exemplary embodiment, the LEDGF composition are implanted or systemically administered in an extended release formulation. In one exemplary embodiment, the extended release formulation is a nanoparticle extended release formulation of the present invention, such as a LEDGF/zinc nanoparticle formulation. In another exemplary embodiment, the extended release formulation is a particle-in-particles formulation, such as a nanoparticle in porous microparticle (NPinPMP) formulation.

In another exemplary embodiment, the present invention comprises methods of treating neurodegenerative diseases comprising administering to a patient with a neurodegenerative disease a composition comprising a LEDGF peptide of the present invention. In certain exemplary embodiments, the LEDGF peptide is $LEDGF_{1-326}$. In one exemplary embodiment, the LEDGF composition is delivered intraperitoneally. In another exemplary embodiment, the LEDGF composition is administered orally. In another exemplary embodiment, the LEDGF composition are administered systemically in an extended release formulation. In one exemplary embodiment, the extended release formulation is a nanoparticle extended release formulation of the present invention, such as a LEDGF/zinc nanoparticle formulation. In another exemplary embodiment, the extended release formulation is a particle-in-particle formulation, such as a nanoparticle in porous microparticle (NPinPMP) formulation.

In another exemplary embodiment, the present invention comprises methods of reducing protein aggregation in a neurodegenerative disease comprising administering to a patient with a neurodegenerative disease a composition comprising a LEDGF peptide of the present invention. In certain exemplary embodiments, the LEDGF peptide is $LEDGF_{1-326}$. In one exemplary embodiment, the LEDGF composition is delivered intraperitoneally. In another exemplary embodiment, the LEDGF composition is administered orally. In another exemplary embodiment, the LEDGF composition is administered in an extended release formulation. In one exemplary embodiment, the extended release formulation is a nanoparticle extended release formulation of the present invention, such as a LEDGF/zinc nanoparticle formulation. In another exemplary embodiment, the extended release formulation is a particle-in-particle formulation, such as a nanoparticle in porous microparticle (NPinPMP) formulation.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention.

EXAMPLES

Example 1

1. Materials

Plasmid pEGFP-LEDGF was gifted by Dr. Toshimichi Shinohara (University of Nebraska Medical Center, Omaha, Nebr.). Forward and reverse primers were obtained from Integrated DNA Technologies (Coralville, Iowa). DNA polymerase I, T4 DNA ligase, and restriction enzymes were obtained from New England Biolab Inc. (Ipswich, Mass.). QIAquick gel extraction kit, QIAprep spin miniprep kit, and QIAGEN plasmid mini kit were obtained from Qiagen (Valencia, Calif.). XK 16/20 column, S-200 gel filtration column, SP sepharose beads were obtained from GE Lifesciences Healthcare (Piscataway, N.J.). ARPE-19 cells were obtained from ATCC (Manassas, Va.). DMEM/F12 cell culture medium, fetal bovine serum, Lipofectamine 2000, LB medium, and ultra-pure agarose were obtained from Invitrogen (Carlsbad, Calif.). All other materials unless specified were obtained from Sigma-Aldrich (St. Louis, Mo.).

Preparations of $LEDGF_{1-326}$ DNA Construct

Gene encoding $LEDGF_{1-326}$ protein was cloned into a pET-28 a (+) vector (Novagen, Madison, Wis.). Briefly, the $Ledgf_{1-326}$ gene was PCR (polymerase chain reaction) amplified from the pEGFP-LEDGF plasmid using the forward primer 5'AGTAGTGGATCCATGACTCGCGATT-TCAAAC3' (SEQ ID NO: 3) consisting of HindIII restriction endonuclease site and reverse primer 5'AATAAT AAGCTTTCACTGCTCAGTTTCCATTTGTTC'3 (SEQ ID NO: 4) consisting of BamHI restriction endonuclease site. PCR amplification was done using DNA polymerase I at 94° C. denaturation for 5 min followed by 36 cycles of denaturation at 94° C. for 30 secs, annealing at 50° C. for 45 secs, and extension at 72° C. for 2 min, and a final step of extension at 72° C. for 5 min. The amplified $Ledgf_{1-326}$ gene was purified using the QIAquick gel extraction kit as per manufacturer's protocol. Thereafter the purified $Ledgf_{1-326}$ gene insert and pET-28a(+) vector were serially digested at 5' and 3' end using HindIII and BamHI restriction enzymes respectively. They were then purified using a QIAprep spin miniprep kit as per manufacturer's protocol. The sticky ends of the insert and the vector were ligated overnight at 4° C. using T4 DNA ligase. Competent Escherichia coli DH5α cells were transformed with the ligation product using heat shock procedure as per the manufacturer's protocol. Ten colonies were picked and the plasmid was amplified, extracted, and purified using the QIAGEN plasmid mini kit. Insertion of the $Ledgf_{1-326}$ in pET-28a(+) vector was confirmed by three different ways, first by PCR screening, second by restriction digest, and finally by DNA sequencing. Purity and the size of the recombinant DNA was analyzed using 2% agarose gel. DNA quantifications were done using NanoDrop 1000 (Thermo scientific, Wilmington, Del.). The colony showing positive PCR signal and correct sequencing was cultured further and the bacterial glycerol stock was made and stored at −80° C. for all future use.

Bioinformatic Analysis $LEDGF_{1-326}$ amino acid sequence was submitted to ExPASy bioinformatics resource portal and the molecular weight, theoretical pI, amino acid composition, atomic composition, extinction coefficient, estimated half-life of LEDGF$_{1-326}$ was computed.

Expression and Purification of LEDGF$_{1-326}$

For protein biosynthesis, pLEDGF$_{1-326}$ plasmid was amplified and purified from *Escherichia coli* DH5α colony using QIAGEN plasmid mini kit as per manufacturer's protocol. The plasmid was then transformed in *Escherichia coli* BL21(DE3) strains as per manufacturer's protocol. Thereafter, a single colony of the bacteria containing the plasmid was inoculated into LB (Luria broth) medium containing 50 μg/ml of kanamycin overnight. A 1% inoculum of overnight grown culture was added to one liter of LB medium containing 50 μg/ml of kanamycin. The culture was allowed to grow at 37° C. until the optical density (O.D.) of 0.6-0.8 was reached for the culture medium. Protein expression was induced by adding IPTG (Isopropyl-β-D-thiogalactoside) to the final concentration of 200 μM. Thereafter, cells were further incubated for 3 hours at 37° C. and harvested by centrifugation at 3000 g for 15 min at 4° C. Harvested cells were resuspended in buffer A (25 mM Tris-HCl pH 7.0, 1 mM EDTA, 1 mM PMSF, and 5% sucrose). Cells were pulse sonicated (Mesonix, Sonicator 3000, Farmingdale, N.Y.) at 70% output (36 watt) for 5 secs followed by cooling for 15 secs for total of 30 min. Lysed cells were centrifuged at 13000 g for 20 min at 4° C. to separate the soluble and insoluble fractions of the lysate. The soluble (supernatant) and insoluble (pellet) fractions were analyzed on SDS-PAGE for protein content and determination of soluble/insoluble nature of produced protein.

FPLC:

LEDGF$_{1-326}$ was solely expressed in soluble fraction as determined by SDS-PAGE. LEDGF$_{1-326}$ was purified using fast protein liquid chromatography (FPLC) technique in two steps, first based on charge (cation exchange) and then based on size (gel filtration). Briefly, cation exchange SP sepharose beads were packed in XK 16/20 column and equilibrated using buffer A at 2 ml/min flow rate. Thereafter, the soluble fraction was loaded on the column at flow rate of 1 ml/min. The column was then washed with five column volume of buffer A at 2 ml/min flow rate. Most of the non-specifically and loosely bound impurities were eluted using a sharp gradient of sodium chloride (0 to 28% conductance). After removal of significant proportion of column bound impurities, further elution of LEDGF$_{1-326}$ was achieved using second gradient of NaCl from 28 to 40% conductance in 40 min. The protein elution profile was monitored by measuring absorbance at 280 nm using an inbuilt UV detector. Fractions of 2.5 ml were collected during elution process and analyzed on SDS-PAGE to determine purity. Fractions containing high protein amount were pooled together. The pooled fractions were dialyzed using dialysis buffer (25 mM Tris pH 7.0, and 0.1% sucrose) and then lyophilized for 48 hours. The lyophilized protein was solubilized in 2 ml of D.I. water. For the next step of purification, pre-packed S-200 gel filtration column was equilibrated using the equilibration buffer B (25 mM Tris-HCl pH 7.0, and 100 mM NaCl) at flow rate of 1 ml/min. The LEDGF$_{1-326}$ concentrated solution from the cation exchange was then loaded onto the S-200 column. LEDGF$_{1-326}$ was eluted using the buffer B at a flow rate of 1 ml/min. A sharp peak was obtained at about 100 min, fractions of 1 ml were collected. The collected fractions were analyzed using SDS-PAGE. Fractions containing the pure LEDGF$_{1-326}$ were pooled together. The purified LEDGF$_{1-326}$ was then dialyzed extensively in the dialysis buffer (25 mM Tris-HCl pH 7.0, and 0.1% Sucrose), for 48 hours at 4° C. with three buffer exchanges, to remove excess salt and other impurities. The dialyzed LEDGF$_{1-326}$ was frozen and lyophilized for 48 hours at −80° C. The lyophilized LEDGF$_{1-326}$ was aliquoted and stored at −80° C. for all future purposes.

UV spectroscopy:

Twelve mg of the lyophilized LEDGF$_{1-326}$ was accurately weighed and then dissolved in 1 ml of D.I. water. UV absorbance spectrum was recorded from 200 nm to 400 nm using Spectramax M5 (Molecular Devices, Downingtown, Pa.). The sample was serially diluted using D.I. water until absorbance of less than 1 was obtained at 280 nm. This absorbance was used to calculate the amount of purified protein present in the sample based on the molar extinction coefficient.

Physical Characterization

The molecular weight and the purity of the LEDGF$_{1-326}$ protein were determined by SDS-PAGE, SEC-HPLC, and MALDI-TOF.

SDS-PAGE:

Briefly 5 μg of LEDGF$_{1-326}$ was boiled for 10 min in SDS-PAGE sample buffer (containing beta-mercaptoethanol). The protein sample was loaded onto 4-15% SDS-PAGE gel (Bio-Rad, Hercules, Calif.) and electrophoresed for 90 min at 30 mA. The gel was then stained with coomassie brilliant blue and visualized under white light using GelDoc™ XR (Biorad, Hercules, Calif.). For non-reducing SDS-PAGE, LEDGF$_{1-326}$ was diluted in non-reducing sample buffer (no beta-mercaptoethanol) and boiling was avoided.

SEC-HPLC:

The lyophilized protein was dissolved in D.I. water to final concentration of 500 μg/ml and filtered through 0.22 um (PVDF) filter. The protein was assessed using Agilent Bio SEC-3 column using 25 mM Tris buffer containing 1 mM CaCl$_2$, pH 7.0 at 25° C. with a flow rate of 1 ml/min. The column was calibrated with molecular weight standards (Invitrogen). UV-absorbance was measured at 214 nm.

MALDI-TOF:

Protein homogeneity and identity was confirmed by 4800 Plus MALDI TOF/TOF™ (AB Sciex, Framingham, Mass.) by determining the molecular weight. The protein sample was dissolved into a solution of standard MALDI matrix sinnapinic acid, spotted and dried onto the metal target plate. Data were collected as total ion current (TIC) from 1000 laser shots of 5900 intensity.

DLS:

The homogeneity and size of the LEDGF$_{1-326}$ protein was analyzed using zetasizer Nano ZS (Malvern, Westborough, Mass.). Briefly, lyophilized protein sample was dissolved in D.I. water to get final protein concentration of 2.5 mg/ml. Size was measured in terms of number, intensity and volume means using the dynamic light scattering technique with data collection at 173° backscatter angle. Measurement was an average of 13 scans.

Biophysical Characterization

For biophysical characterization the protein was extensively dialyzed in 25 mM phosphate buffer pH 7 to remove Tris-HCl and sucrose and filtered through 0.22 μm PVDF syringe filter. Spectra obtained were analyzed using either Origin® 8.5 (OriginLab Corp., Northampton, Mass.) or SigmaPlot 11.0 (Systat Software, Inc, Chicago, Ill.). The data was fitted using equations 1 and 2, defined by Scholtz et. al. as below to determine the ΔG, m-value, and [urea]$_{1/2}$ [62].

$$y = \frac{\left\{(y°_F + m_F[\text{urea}]) + (y°_U + m_U[\text{urea}]) \times e^{-\left(\frac{\Delta G(H_2O) - m[\text{urea}]}{RT}\right)}\right\}}{1 + e^{-\left(\frac{\Delta G(H_2O) - m[\text{urea}]}{RT}\right)}}$$

$$\Delta G = \Delta G(H_2O) - m[\text{urea}]$$

where $y°_F$ and $y°_U$ are the intercepts, $m_F$ and $m_U$ are the slopes of the pre- and post-transition phase baselines, and m-value is the slope of the transition phase. AG is the free energy change at any particular urea concentration and it varies linearly with urea concentration, and is used to estimate $\Delta G(H_2O)$. $\Delta G(H_2O)$ is defined as the conformational stability of a protein in the absence of urea at 25° C. R is universal gas constant and T is the temperature of the sample. [urea]$_{1/2}$ is the concentration of urea at which LEDGF$_{1-326}$ is 50% folded and 50% unfolded.

CD:

To determine the secondary structures of LEDGF$_{1-326}$ and determine its conformational stability parameters, far-UV CD spectrum of the dialyzed protein was recorded. Briefly, 500 μg/ml of protein sample was placed in 1 mm quartz cuvette and spectra was recorded at a scan speed of 0.5 secs per time point, step size of 1 nm and the bandwidth of 4 nm from 200 to 280 nm using Chirascan® CD instrument (Applied Photophysics Ltd, UK). All scans were done in triplicate. The native LEDGF$_{1-326}$ spectrum thus obtained was deconvulated using CDNN 2.1 CD spectra deconvulation software (Dr. Gerald Bohm, Martin-Luther-University at Halle, Wittenberg, Germany, UK) to get the percentage of various secondary structures present in native LEDGF$_{1-326}$ protein. For conformational stability of LEDGF$_{1-326}$, chemical denaturation was performed at various urea concentrations. Briefly, 300 μg/ml of protein was incubated with 0 to 6 M urea in 25 mM phosphate buffer pH 7.0 for 24 hours. CD signal was recorded as mentioned above. The conformational stability parameters of LEDGF$_{1-326}$ were determined by plotting the CD signal at 230 nm as a function of urea concentration to obtain the maximum CD signal difference between the folded and unfolded protein spectrum at this wavelength. Similarly, to investigate the thermal stability of LEDGF$_{1-326}$, 500 μg/ml of LEDGF$_{1-326}$ was subjected to heat denaturation from 25° C. to 90° C. in smooth ramp mode at ramp rate of 1° C. per min. The CD signal at 222 nm was used to determine the melting point ($T_m$).

Fluorescence Spectroscopy:

Steady state fluorescence spectroscopy was done to determine the tertiary structure perturbation. The protein sample (final concentration 300 μg/ml) was incubated with various concentration of urea solution (0 to 6 M) in 25 mM phosphate buffer pH 7.0 for 24 hours. The intrinsic tryptophan fluorescence spectra were recorded from 300 to 400 nm, at 280 nm excitation wavelength, with an increment of 1 nm using Spectramax M5 (Molecular Devices, Downingtown, Pa.). The conformational stability parameters of LEDGF$_{1-326}$ were determined by plotting the fluorescence intensity ratio at 340/356 nm as a function of urea concentration. All intensity values were corrected for buffer effects and inner filter effects.

Cell Viability Assay

ARPE-19 cells were used to determine the cell survival function of LEDGF$_{1-326}$ in presence of aggregation mediated stress. Briefly, ARPE-19 cells were maintained as describer earlier (Baid et al., PLoS One. 6(9): p. e24616). For cell viability assay, 10,000 cells were plated in 96-well plate and incubated for 24 hours. After 24 hours, the serum containing medium was aspirated out. The test groups (pP23H-Rho+ LEDGF$_{1-326}$) were transiently transfected with pP23H-Rho plasmid (1 μg/ml) using 1:3 ratio of lipofectamine 2000 in serum free medium as per manufacturer's protocol. After six hours of transfection, the medium were aspirated out and cells were treated with increasing amount of LEDGF$_{1-326}$ with the concentration range of 0.001 μg/ml to 50 μg/ml for 48 hours. No cells (just the medium), cells with no lipofectamine 2000 and cells with lipofectamine 2000 were also maintained as control. After 48 hours, the medium was aspirated out and 200 μl of fresh serum free medium was added. 20 μl of MTT reagent (3-(4,5-dimethylthiazol-2-yl)-2,5-diphenyl tetrasodium bromide, 5 mg/ml in PBS pH 7.4) was added to each well and further incubation was done for 3 hours at 37° C. The MTT containing medium was aspirated out and the formazan crystal formed was dissolved in 200 μl of DMSO. The absorbance of the color developed was measured at 570 nm using Spectramax M5. The percentage viability of groups was calculated with reference to the control group containing cells with no lipofectamine 2000. All groups were repeated as n=4.

Animal Maintenance

A RCS rat colony was maintained in the animal facility of University of Colorado Anschutz Medical Campus and with approval of IUCAC. The experiments were carried as per the ARVO statement for the Use of the Animals in Ophthalmic and Vision Research.

Electroretinography

At 4 weeks age, rats were dark adapted for 30 min. Thereafter, the animal was prepared for ERG under dim red light. Briefly, the rat was anaesthetized with intraperitoneal injection of mixture of 80 mg/kg of ketamine and 12 mg/kg of xylazine. The pupil was then dilated with a drop of 0.5% tropicanamide (Akorn, Lake Forest, Ill.) and was kept moist using a drop of 2.5% hypromellose (Akorn, Lake Forest, Ill.). Thereafter, the animal was placed on a heated water jacket stabilized at 37° C. A reference electrode (LKC Technologies Inc., Gaithersburg, Md.) was inserted into the animal's tail and cheek. A DTL plus electrode (LKC Technologies Inc., Gaithersburg, Md.) was placed across the cornea of each eye. Each animal was exposed to brief flashes of 0.4 log cd-s/m2 with interval of 10 secs between each flash and scotopic ERG was recorded. Thereafter, the animal was light adapted for 3 min with a background light of 30 cd/m². Photopic ERG was recorded at same intensity flash but with background light on. At least three ERGs were averaged to get a single ERG for each rat. Thereafter, sterile filtered, 2 μl of 0.25, 0.5, or 2.5 mg/ml of LEDGF$_{1-326}$ was given intravitreally in one eye and vehicle in contralateral eye. ERGs were recorded every two weeks for 8 weeks after intravitreal injection, i.e. till week 12 age of rats.

Statistical Analysis

Data are represented as the mean±SD. An independent-samples student's t-test or one-way ANOVA followed by Tukey's post hoc analysis (SPSS, ver.11.5; SPSS, Chicago, Ill.) was performed for comparisons between the two or multiple experimental groups, respectively. The differences were considered statistically significant at p≤0.05.

2. Results

LEDGF$_{1-326}$ Cloned into pET28a(+)

Figure 3:
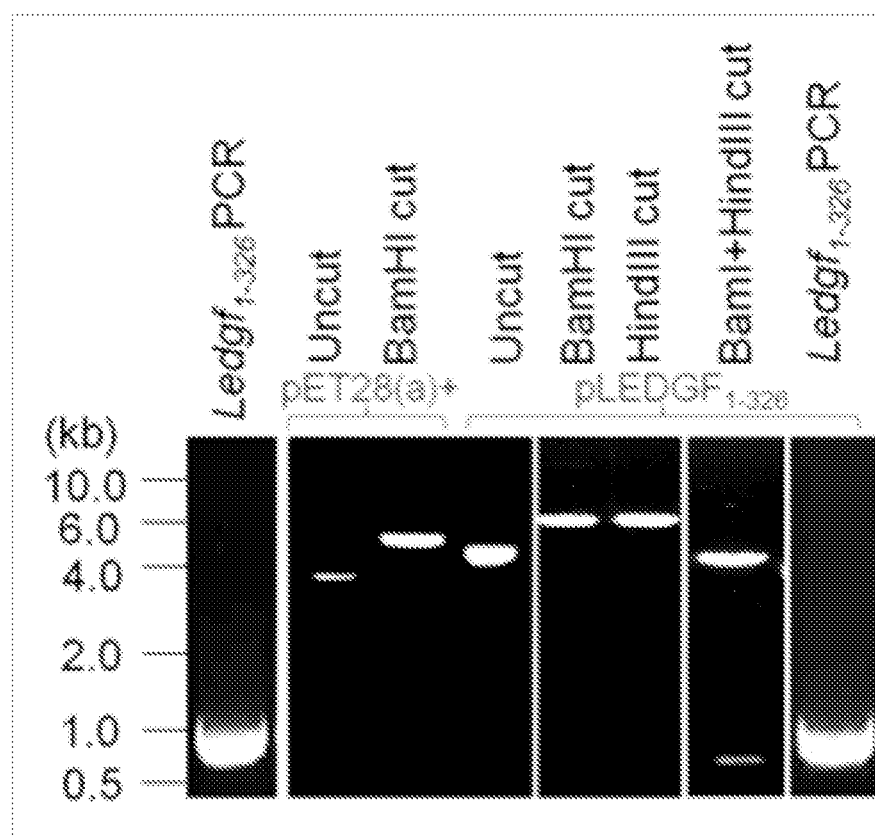
FIG. 3 is a picture of an agarose gel showing the successful cloning of a nucleic acid sequence encoding $LEDGF_{1-326}$ into pET-28 a (+). $Ledgf_{1-326}$ gene was PCR amplified and then ligated into pET-28 a (+) vector. Lane 1: PCR amplified $Ledgf_{1-326}$ gene, Lane 2: uncut circular pET-28 a (+), Lane 3: linearized BamHI digested pET-28 a (+), Lane 4: uncut circular $pLEDGF_{1-326}$ (pET-28 a (+) ligated with $Ledgf_{1-326}$), Lane 5: linearized BamHI digested $pLEDGF_{1-326}$, Lane 6: linearized HindIII digested $pLEDGF_{1-326}$, Lane 7: BamHI and HindIII double digested $pLEDGF_{1-326}$, Lane 8: PCR amplification of $Ledgf_{1-326}$ gene from $pLEDGF_{1-326}$.

DNA fragment of about 1000 base pairs was obtained from the polymerase chain reaction (PCR) amplification of Ledgf$_{1-326}$ gene (FIG. 3, Lane 1) from pEGFP-LEDGF plasmid. The undigested pET-28 a (+) vector (Lane 2) showed a positive band at about 4.5 kb, which when digested using BamHI got linearized and shifted upward in between 5 and 6 kb DNA marker (Lane 3). When Ledgf$_{1-326}$ gene was ligated in pET-28a (+) vector (the plasmid so obtained will be designated as pLEDGF$_{1-326}$ from here onwards), there was an upward band shift equivalent to ~1000 bp, indicating successful insertion of Ledgf$_{1-326}$ gene in the pET28a(+) vector (Lane 4). To confirm the ligation, pLEDGF$_{1-326}$ was singly digested either with BamHI (Lane 5) or HindIII (Lane 6). pLEDGF$_{1-326}$ was linearized by both restriction enzyme digestion reactions and the DNA band was seen at about 6.4 kb which was 1000 bp more than pET28a(+) vector. Double digest of pLEDGF$_{1-326}$ using BamHI and HindIII resulted in two fragments, a bigger fragment of ~5.4 kb (upper band, Lane 8) and a smaller fragment of ~1000 bp (lower band, Lane 7). PCR amplification of Ledgf$_{1-326}$ gene from pLEDGF$_{1-326}$ resulted in a positive DNA band of about 1000 bases (Lane 8), indicating that LEDGF$_{1-326}$ was inserted successfully in pET-28 a (+) vector.

Bioinformatic Analysis of LEDGF$_{1-326}$

Bioinformatics analysis of LEDGF$_{1-326}$ sequence using SIB ExPASy (Gasteiger et al., Nucleic Acids Res, 2003. 31(13): p. 3784-8) indicated its theoretical molecular weight of 36.9 kDa. The computed isoelectric point (pI) of LEDGF$_{1-326}$ was 9.23, with 73 positively charged (arginine and lysine) and 63 negatively charged (aspartic acid and glutamic acid) amino acid residues. The theoretical molar extinction coefficient was 15470 $M^{-1}$ $cm^{-1}$ at 280 nm in water. Based on its N-terminal amino acid methionine, its half-life in mammalian cells was predicted to be 30 hours.

LEDGF$_{1-326}$ Purified in Bulk Quantities

Figure 4:
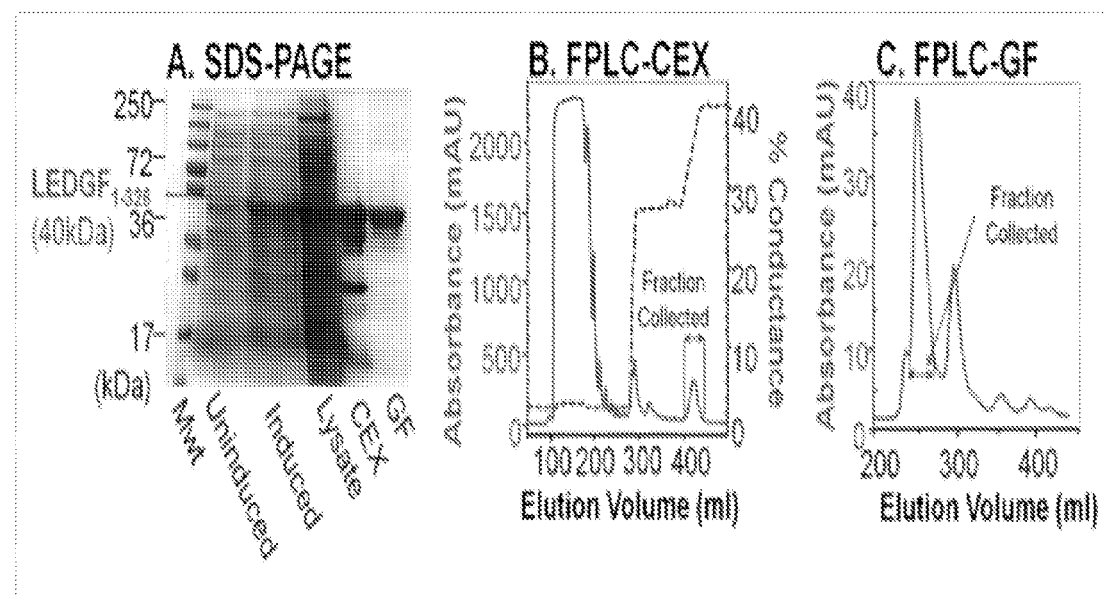
FIGS. 4A-C are set of graphs showing successful expression and purification of $LEDGF_{1-326}$: A) SDS-PAGE—Lane 1 Protein marker (Fermentas, Glen Burnie, Md.), Lane 2 uninduced cell lysate, Lane 3 IPTG induced cell lysate, Lane 4 Soluble fraction of lysate, Lane 5 $LEDGF_{1-326}$ obtained from FPLC-cation exchange column, Lane 6 $LEDGF_{1-326}$ obtained from FPLC-gel filtration column; B) FPLC-cation exchange chromatogram; C) FPLC-gel filtration chromatogram.

A new strong positive band appeared, at about 40 kDa, when LEDGF$_{1-326}$ was expressed under specified conditions in BL21(D3B) cells indicating expression of LEDGF$_{1-326}$ protein (FIG. 4A, Lane 3). This band appeared in the supernatant fraction after the bacterial cell lysis, indicating that LEDGF$_{1-326}$ was expressed as soluble protein in bacterial culture (Lane 4). LEDGF$_{1-326}$ was purified from the crude cell lysate using fast protein liquid chromatography (FPLC) system. In first step of purification, cation exchange column was used (FIG. 4B). The unbound protein and other cellular impurities including lipids got eluted during the column washing phase (100-280 ml). Thereafter, other cellular proteins which were loosely bound to the column got eluted out when the conductance of the mobile phase was increased from 0 to 28% using sharp sodium chloride (NaCl) gradient (280-400 ml). When the gradient of NaCl was further increased slowly over 40 min to reach 40% conductance, LEDGF$_{1-326}$ was eluted (400-450 ml). When the collected fraction was analyzed using SDS-PAGE, a strong band of LEDGF$_{1-326}$ at ~40 kDa was seen along with other lower molecular weight bands (FIG. 4A, Lane 5). On further purification using the gel filtration column, LEDGF$_{1-326}$ was eluted as the first peak (fractions collected), followed by peaks of other proteins of smaller molecular weights (FIG. 4C). Pooled fractions from the gel filtration columns indicated a strong positive band of ~40 kDa in SDS-PAGE along with very faint low molecular weight bands indicating almost complete purification of LEDGF$_{1-326}$ (FIG. 4A, Lane 6). Protein estimation indicated that about 20 mg of protein was obtained per liter of the shake flask culture.

LEDGF$_{1-326}$ is Purified to Near Homogeneity

Figure 5:
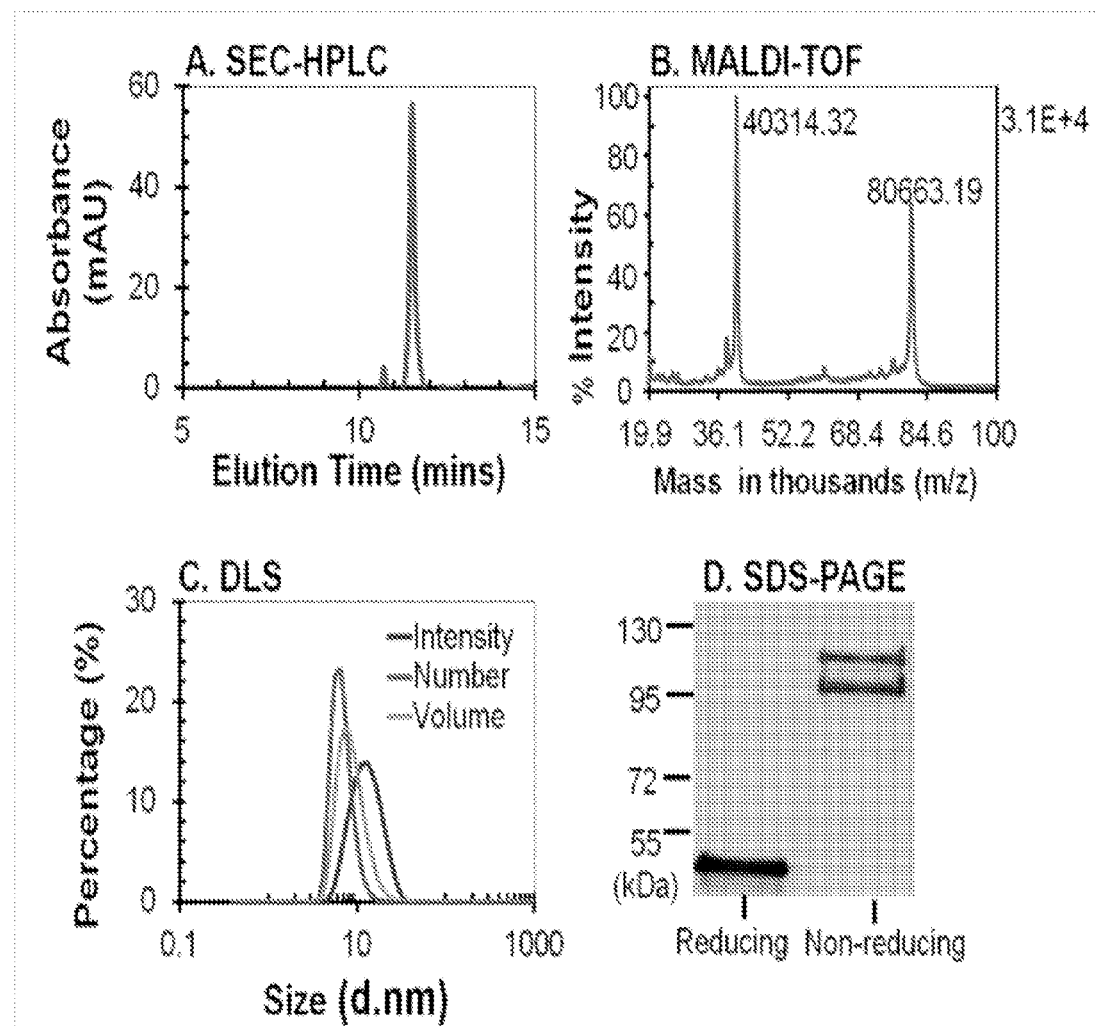
FIGS. 5A-D are set of graphs showing certain physical characteristics of $LEDGF_{1-326}$. A) SEC-HPLC: $LEDGF_{1-326}$ was size separated on Agilent Bio-SEC column using 25 mM Tris-HCL buffer containing 1 mM $CaCl_2$, pH 7.0. $LEDGF_{1-326}$ was eluted primarily as single peak at 11.5 min with about 5% higher molecular weight species. B) MALDI-TOF: $LEDGF_{1-326}$ has a molecular weight of 40 kDa, and may exist as a dimer. C) DLS: $LEDGF_{1-326}$ size was analyzed in 25 mM phosphate buffer, pH 7.0 using Nano ZS. $LEDGF_{1-326}$ had a monodispersed population of about 10 nm diameter, with the absence of aggregates. D) SDS-PAGE: $LEDGF_{1-326}$ was size separated on a 4-15% SDS-PAGE gel under reducing (beta-mercaptoethanol and boiling) and non-reducing (no beta-mercaptoethanol and no boiling) conditions. The non-reducing gel indicated the presence of dimers of $LEDGF_{1-326}$.

The purity of LEDGF$_{1-326}$ protein was determined by size exclusion chromatography (SEC-HPLC) (FIG. 5A). Two peaks were observed, first peak had a retention time of 10.5 min and the second peak had the retention time of about 11.5 min. When the area under the curve was integrated, the first peak was only 5% and the second peak was 95%, indicating that LEDGF$_{1-326}$ protein was about 95% pure. The molecular weight of LEDGF$_{1-326}$ was confirmed by matrix assisted laser desorption/ionization (MALDI-TOF). The major peak obtained in MALDI-TOF spectrum was at 40314.32 and 80663.19 m/z (mass to charge) ratio (FIG. 5B). MALDI-TOF indicated that LEDGF$_{1-326}$ has a molecular weight of 40 kDa, which was equivalent to theoretical molecular weight. A second peak at 80663 m/z was also seen, which indicated that LEDGF$_{1-326}$ may exist as dimer. To investigate the existence of the dimers, SDS-PAGE of LEDGF$_{1-326}$ was run under reducing and non-reducing conditions (FIG. 5D). Under non-reducing conditions, there was an upward shift of the LEDGF$_{1-326}$ band to 95-105 kDa size, indicating that LEDGF$_{1-326}$ may exist in dimeric form. Under reducing/denaturing conditions the dimers dissociated into monomers.

To further investigate whether LEDGF$_{1-326}$ self-associates to form any higher molecular weight oligomers, dynamic light scattering (DLS) was performed (FIG. 5C). A homologous population having a single peak (100% distribution) was obtained for intensity or number or volume size distribution of the particles. All three peaks were in the narrow size distribution indicating a very close size range. There were no other peaks of higher sizes indicating absence of any kind of oligomers. The z-average diameter of 11.32 nm, and a polydispersity index of 0.15 was obtained from DLS.

LEDGF$_{1-326}$ is Randomly Coiled

Figure 6:
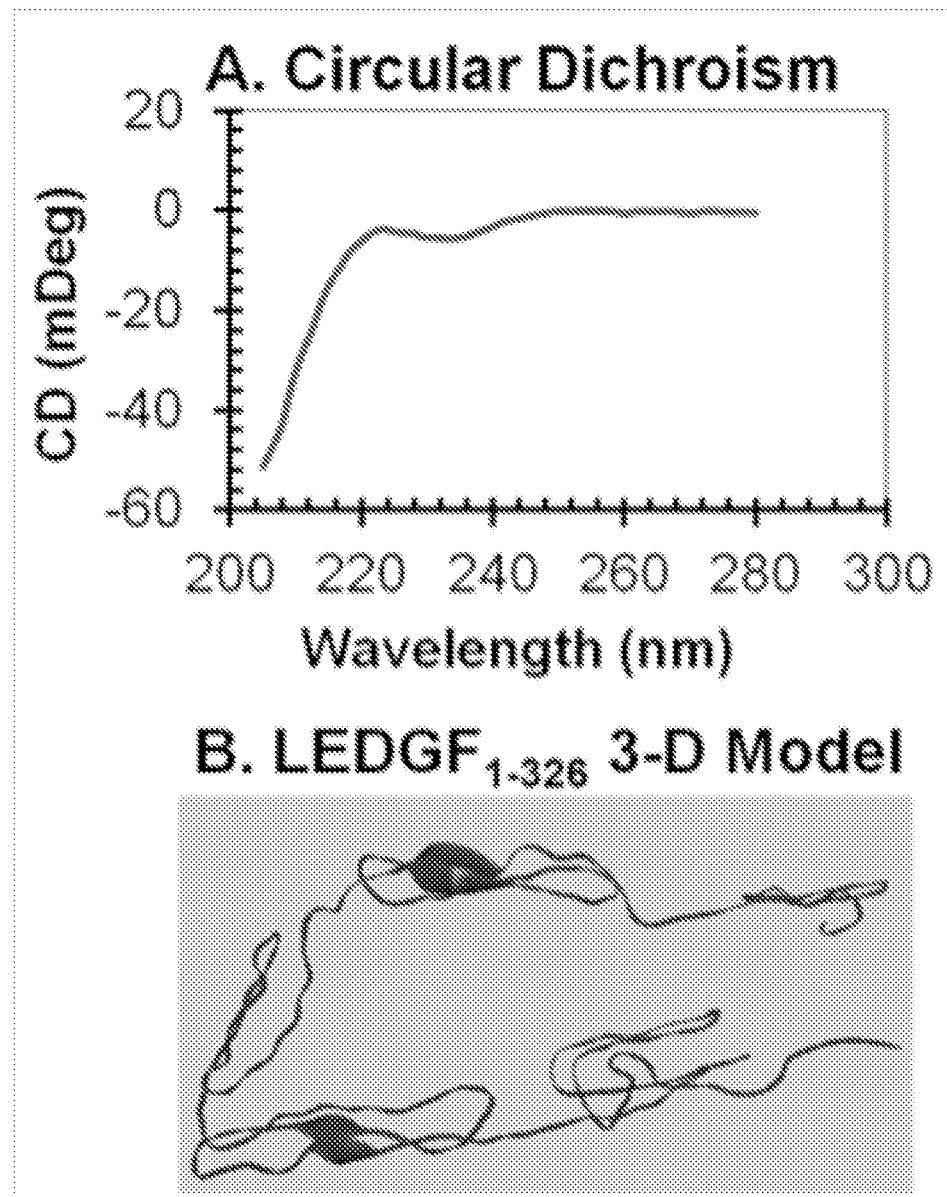
FIG. 6A-B are a set of graphs representing additional data on predicted structural features of $LEDGF_{1-326}$. A) Circular dichroism: Secondary structures of 500 µg/ml $LEDGF_{1-326}$ in 25 mM phosphate buffer pH 7.0 was analyzed using Chirascan. No characteristic peaks were obtained for α-helix or β-sheets. Further, presence of the strong negative signal at 200 nm indicated that $LEDGF_{1-326}$ is primarily a random coiled protein. B) $LEDGF_{1-326}$ 3-D Model: $LEDGF_{1-326}$ 3-D structure was predicted by I-Tasser protein modeling server based on its amino acid sequence and homology with proteins whose structures are available in protein data bank. According to the 3-D model, $LEDGF_{1-326}$ is a random coiled protein.

To investigate the secondary structure of LEDGF$_{1-326}$, far-UV circular dichroism (CD) spectrum of the native LEDGF$_{1-326}$ was analyzed (FIG. 6A). The CD signal remained negative from 280 to 200 nm. After 220 nm, there was a steep decline in the CD signal. There were no characteristic negative bands at 222 nm and 208 nm, neither there was any characteristic positive band near 200 nm indicating that LEDGF$_{1-326}$ do not possess predominantly α-helix or β-sheets. In fact very low ellipticity above 210 nm and negative band below 200 nm indicated that the LEDGF$_{1-326}$ may be composed of primarily random coils.

To further dissect the secondary structure of LEDGF$_{1-326}$, the CD spectrum was deconvulated using CDNN 2.1 software. Assuming that the spectrum obtained is the linear combination of the individual spectrum of the component secondary structure elements and noise due to the aromatic chromophores and prosthetic groups, LEDGF$_{1-326}$ was predicted to be 45.1% randomly coiled. The β-turn was about 21.2%, there were 15% parallel β-sheets and 16% antiparallel β-sheets. The contribution from the α-helix was about only 16%.

The three dimensional structure of LEDGF$_{1-326}$ native protein was predicted using I-Tasser (Iterative Threading Assembly Refinement) protein modeling server (FIG. 6B). LEDGF$_{1-326}$ predicted model had the confidence score (C-score) of −3.18, Template modeling (TM-score) of 0.36±0.12, and root mean square deviation (RMSD) was equal to 14.1±8 Å, indicating that the predicted model is reliable. According to the predicted model, LEDGF$_{1-326}$ was predominantly a random coiled protein.

LEDGF$_{1-326}$ is Conformationally Stable

Figure 7:
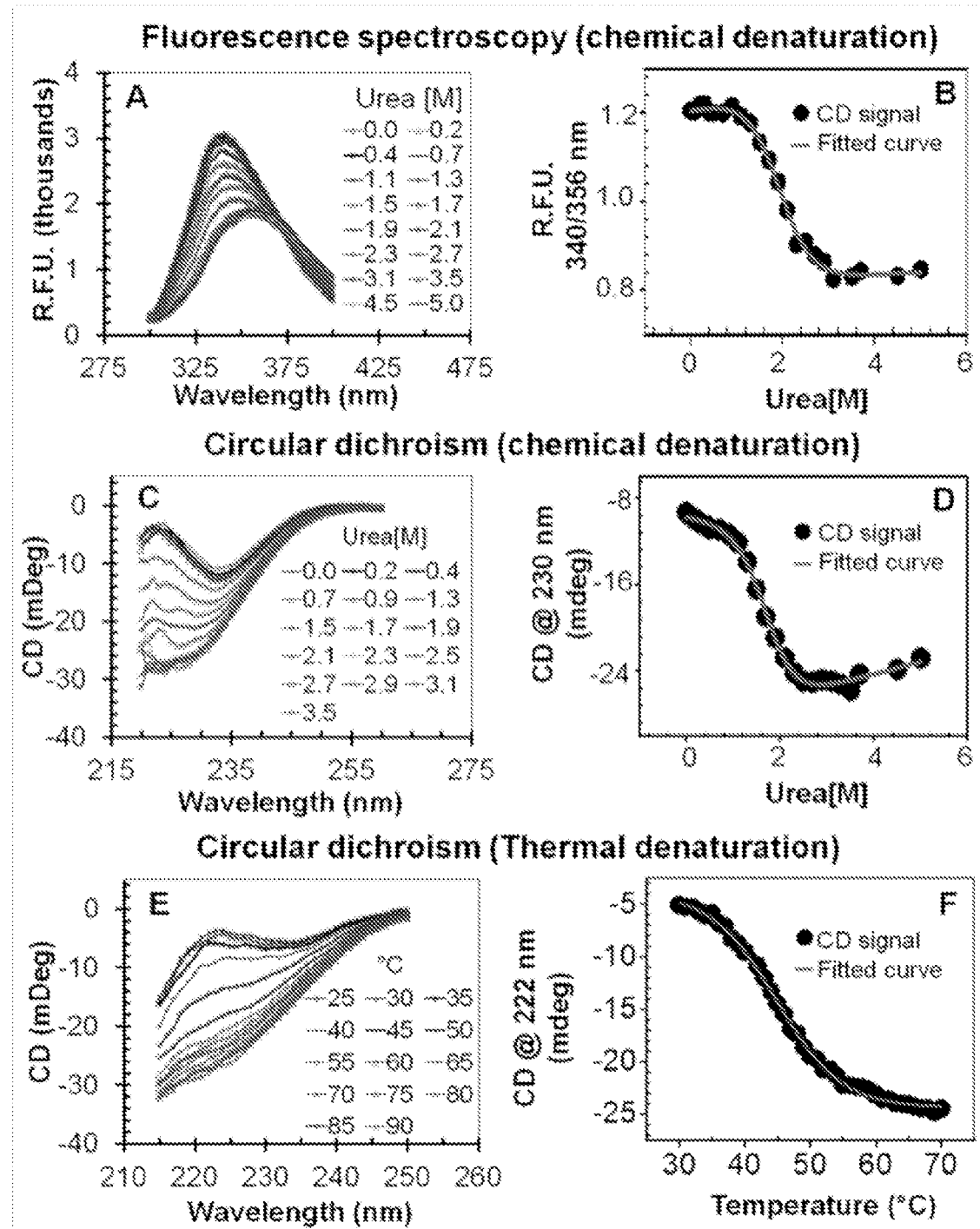
FIG. 7A-F provides additional graphs representing additional data on the predicted structural features of $LEDGF_{1-326}$. Fluorescence spectroscopy-chemical denaturation: A) Fluorescence spectra of 300 µg/ml of $LEDGF_{1-326}$ incubated with 0-6 M urea in 25 mM phosphate buffer at pH 7.0 was recorded from 300 to 400 nm at the excitation wavelength of 280 nm. B) Ratio of fluorescence intensity at 340/356 nm was plotted against the urea concentration to determine conformational stability parameters. C) CD spectra of 300 µg/ml of $LEDGF_{1-326}$ incubated with 0-6 M urea in 25 mM phosphate buffer at pH 7.0 was recorded from 220 to 260 nm. D) CD signal at 230 nm was plotted against the urea concentration to determine conformational stability parameters. E) $LEDGF_{1-326}$ was denatured using heat and the corresponding changes in the CD signal were recorded from 215 to 250 nm. F) CD signal at 222 nm was plotted against the temperature to determine the melting temperature of $LEDGF_{1-326}$.

To understand the conformational stability of LEDGF$_{1-326}$ in water, the perturbation in the tertiary structure due to chemical denaturation was determined by measuring the intrinsic fluorescence of tryptophan molecules present in LEDGF$_{1-326}$ (FIGS. 7A and 7B). Emission spectrum of native LEDGF$_{1-326}$ protein, in absence of urea, had a $\lambda_{max}$ at 340 nm and $\Delta\lambda_{1/2}$ (half width of $\Delta\lambda$) of 56 nm (FIG. 7A). As the concentration of urea increased from 0 to 5 M, quenching in the fluorescence signal as well as red shift (fluorescence maxima shifting towards right) was seen. The signal decreased slowly until 0.9 M urea concentration was reached. Thereafter, there was a sharp decrease in the fluorescence signal until 2.3 M urea concentration was reached. Beyond this concentration, the decrease in the fluorescence signal was minimal. The $\lambda_{max}$ of LEDGF$_{1-326}$ shifted to 356 nm and $\Delta\lambda_{1/2}$ was 71 nm at 5 M urea. When the ratio of LEDGF$_{1-326}$ fluorescence signal at 340 to 356 nm was plotted as a function of urea concentration, a sigmoidal curve was obtained (FIG. 7B). There was a slow decline of fluorescence signal from 0-1 M urea (pre transition phase) and then a steep decay from 1-3 M urea (transition phase) followed by a slow decline phase from 3-5 M (post transition phase). Using the equations 1 and 2 (described in methods), $\Delta G(H_2O)$ of LEDGF$_{1-326}$ was estimated to be 3.24±0.48 kcal mol$^{-1}$, the m-value to be 1.70±0.22 kcal mol$^{-1}$M$^{-1}$, and [urea]$_{1/2}$ to be 1.81±0.02 M, indicating that LEDGF$_{1-326}$ is a stable protein.

Far-UV CD spectroscopy was performed to investigate the perturbation in the secondary structures of LEDGF$_{1-326}$ in presence of urea (FIGS. 7C and 7D). The CD signal of the LEDGF$_{1-326}$ was traced against the wavelength at each urea concentration (FIG. 7C). The CD signal continuously became more negative as the concentration of urea was increased. When CD signal at 230 nm was plotted as a function of urea concentration (FIG. 7D), a sigmoidal curve was obtained. Fitting the data in equations 1 and 2, indicated $\Delta G(H_2O)$ of LEDGF$_{1-326}$ to be 3.28±0.40 kcal mol$^{-1}$, m-value of 1.90±0.19 kcal mol$^{-1}$M$^{-1}$, and [urea]$_{1/2}$ to be of 1.61±0.02 M.

LEDGF$_{1-326}$ is Thermally Stable

Thermal stability of LEDGF$_{1-326}$ was determined using far-UV CD spectroscopy (FIGS. 7E and 7F). The CD signal in the presence of heat as a denaturant was measured from 215-250 nm (FIG. 7E). As the temperature of the LEDGF$_{1-326}$ solution was increased, the negative dip obtained at about 235 nm was seen to increase. The CD signal followed the same pattern as chemical denaturation, a pre-transition phase between ~30-35° C., followed by transition phase between ~35-55° C., followed by post-transition phase from ~55-70° C. (FIG. 7F). When this data was fitted using a global fit analysis, the $T_m$ (the melting temperature) of LEDGF$_{1-326}$ obtained was 44.82±0.17° C. indicating LEDGF$_{1-326}$ will possibly be stable at 25° C. (room temperature).

LEDGF$_{1-326}$ Rescues ARPE-19 Cells from Aggregation Mediated Stress

Figure 8:
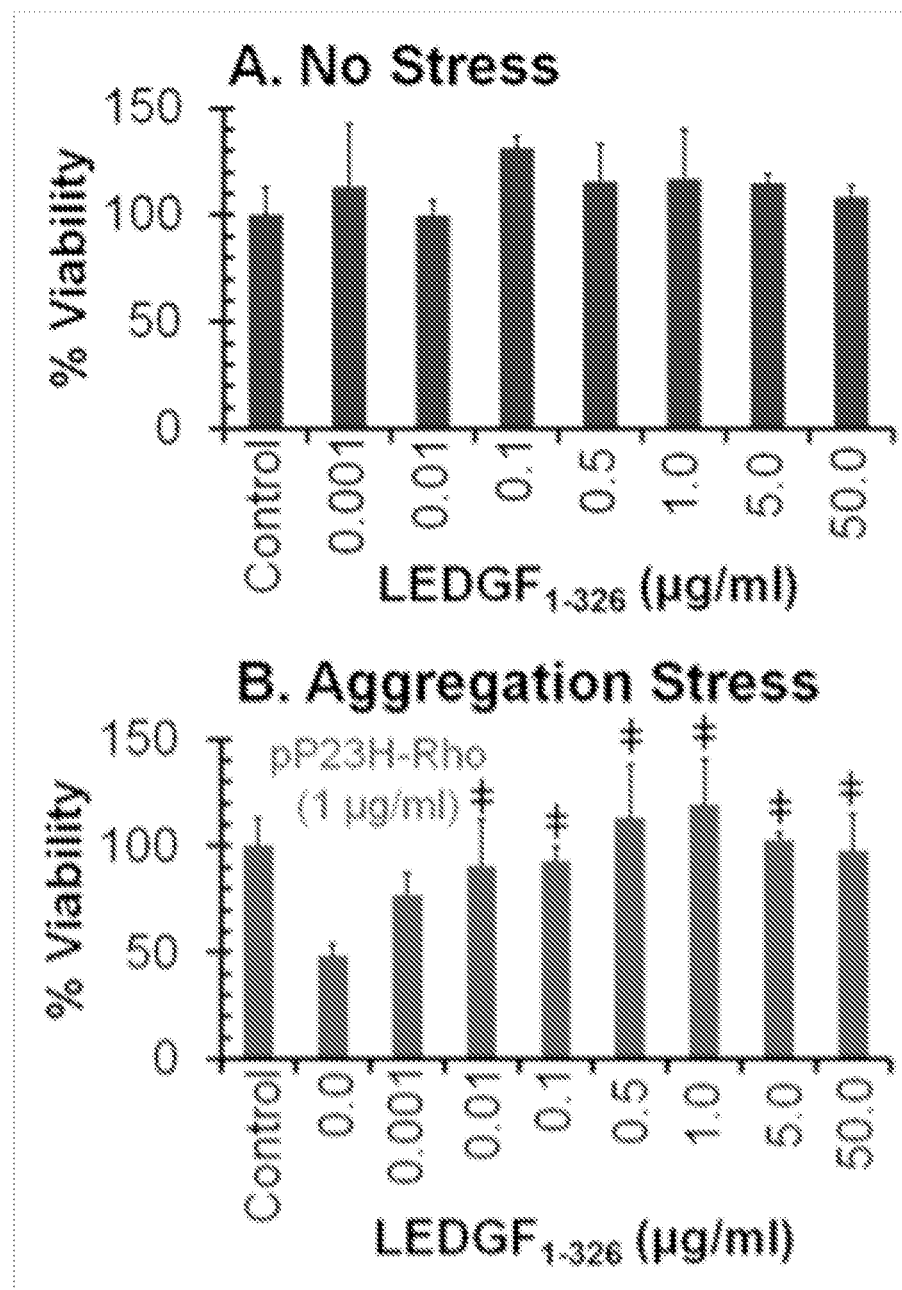
FIG. 8A-B is a set of graphs showing the ability of $LEDGF_{1-326}$ to rescue ARPE-19 cells from aggregation mediated stress. ARPE-19 cells were treated with $LEDGF_{1-326}$ for 48 hours in the A) absence or B) presence of aggregation stress.

LEDGF$_{1-326}$ activity to rescue ARPE-19 cells from protein aggregation mediated stress was measured by cell viability assay (FIG. 8). Initially, the ability of LEDGF$_{1-326}$ to increase the viability of ARPE-19 cells in absence of any stress was investigated (FIG. 8A). There was no significant difference in the cell viability in untreated and 0.001 to 50 µg/ml LEDGF$_{1-326}$ treated cells following 48 hr treatment. At the highest dose of LEDGF$_{1-326}$ (50 µg/ml), the cell viability was 108.14±5.63% (right most bar) as compared to 100±13.19% for untreated cells (left most bar), which was not significant. In pP23H-Rho transfected ARPE-19 cells, LEDGF$_{1-326}$ behaved differently (FIG. 8B). Cells expressing P23H mutant rhodopsin showed a decline in cell viability to 48.25±5.62% (Bar 2). This loss in cell viability could be attributed to toxic effect of expression and accumulation of aggregation prone P23H mutant rhodopsin protein within the cells. When cells expressing P23H mutant rhodopsin (Bar 3-9) were treated with increasing amount of LEDGF$_{1-326}$, an increase in the cell viability was seen. LEDGF$_{1-326}$ increased the cell viability of ARPE-19 cells at as low concentration as 0.001 µg/ml from 48.25±5.62 to 77.02±10. 20%. Beyond this point the cell viability remained significantly higher than the untreated pP23H-Rho transfected group (Bar 2).

LEDGF$_{1-326}$ Delays the Functional Loss of Photoreceptors

Figure 9:
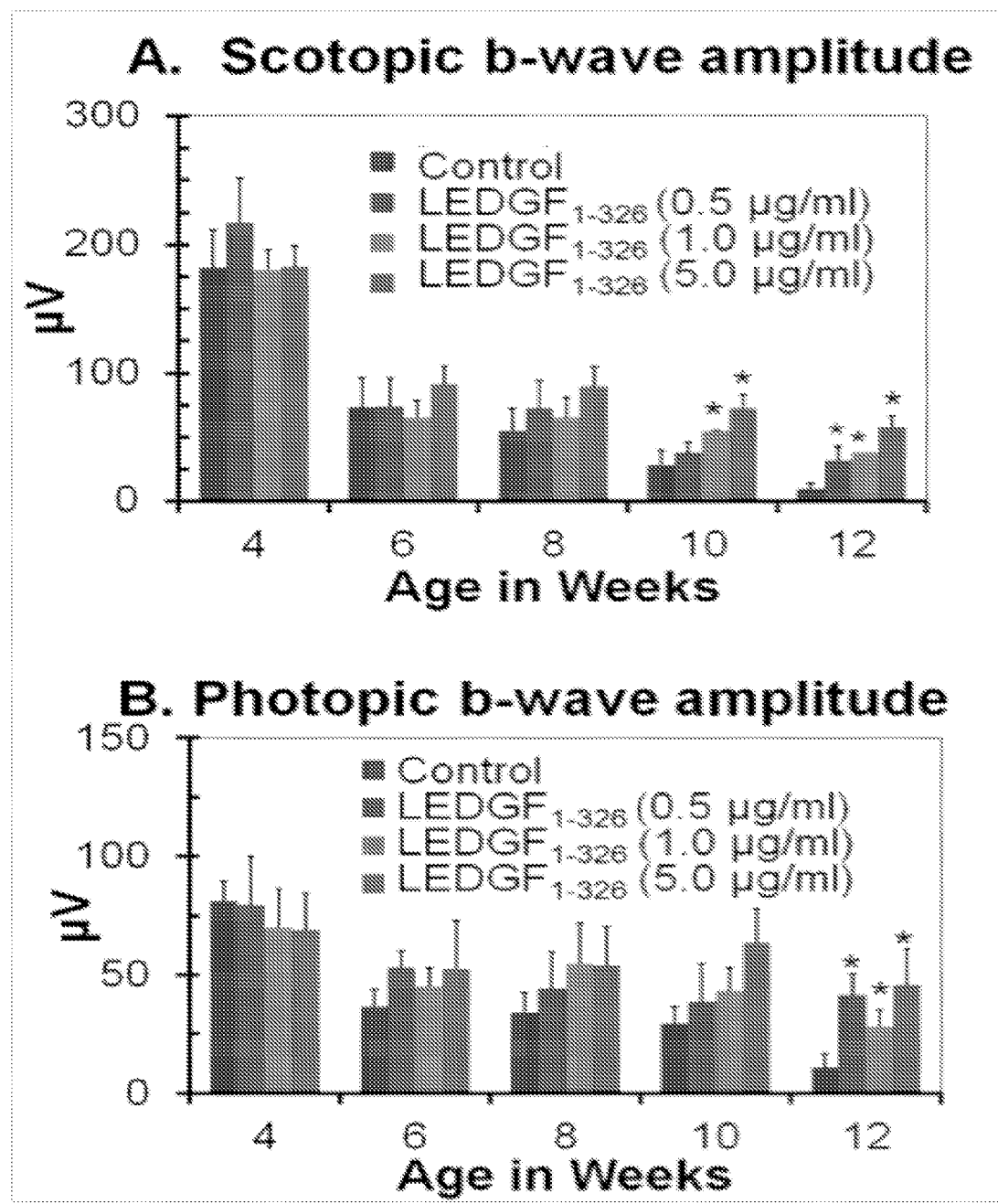
FIGS. 9A-B is a set of graphs demonstrating that $LEDGF_{1-326}$ delays the functional loss of photoreceptors in RCS rats. A) Scotopic ERG was recoded using 0.4 log cd-s/$m^2$ flashes and scotopic B-wave amplitude was plotted against the age of rats. For photopic ERG, rats were light adapted using 30 cd/$m^2$ background light for 3 min before recording the ERG. B) Photopic B-wave amplitude was plotted against the age of rats. Three ERGs were averaged for individual rat and then b-wave amplitude within each group was averaged to get the mean. Data represent mean±S.D. for N=3. *, p<0.05 compared to corresponding untreated group.

LEDGF$_{1-326}$ efficacy to delay the loss of visual function of photoreceptors was investigated in RCS rats by monitoring the electroretinograms (ERG). In dark adapted (scotopic) ERG, the b-wave amplitude of untreated and treated rats ranged from 180.17±27.42 to 216.60±35.30 µV at 4 weeks age (base ERG), before intravitreal injection was administered (FIG. 9A). At two weeks after intravitreal injection, there was a sharp decline in the b-wave amplitude in all groups, the value ranged from 65.80±15.44 to 91.13±13.94 µV. There was no significant difference in the untreated and LEDGF$_{1-326}$ treated groups. However, beyond two weeks, there was a continuous decline in the b-wave amplitude in all groups, with decline being slower in the LEDGF$_{1-326}$ treated groups. At eight weeks after the intravitreal injection, the b-wave amplitude of untreated, 0.5, 1.0, and 5 µg of LEDGF$_{1-326}$ treated groups was 9.40±4.57, 32.43±10.34, 37.93±0.60, and 57.63±8.81 µV, respectively. B-wave amplitude of LEDGF$_{1-326}$ treated groups were significantly ($p<0.05$) higher than the untreated group. A dose dependent delay in the b-wave amplitude decline was seen for the LEDGF$_{1-326}$ treated groups. With increasing dose of LEDGF$_{1-326}$, the loss of b-wave amplitude was reduced.

In light adapted (photopic) ERG, the base b-wave amplitude, before intravitreal injection, at week 4, was in range of 69.83±16.49 to 80.97±8.60 µV, with no significant difference between the untreated and LEDGF$_{1-326}$ treated groups (FIG. 9B). The b-wave amplitude of untreated group declined from 80.97±8.60 to 10.90±5.64 µV, whereas the decline was from 79.63±20.30 to 41.33±9.20, 69.83±16.49 to 28.00±7.23, and 68.75±15.93 to 45.78±15.18 µV for 0.5, 1.0, and 5.0 µg of LEDGF$_{1-326}$ treated groups, respectively. B-wave amplitude of LEDGF$_{1-326}$ treated groups were significantly ($p<0.05$) higher than the untreated group after eight weeks of single intravitreal injection of LEDGF$_{1-326}$ similar to scotopic ERG.

Example 2

1. Materials and Methods

Materials—

Isopropyl-β-D-thio-galactoside (IPTG) citric acid, dibasic sodium hydrogen phosphate, ethylene diamine tetra acetic acid (EDTA), Tween 20, sucrose, sodium azide were purchased from Sigma-Aldrich( ). AKTA FLPC was used for protein purification. All chromatograms were analyzed using UNICORN software. All chemicals unless specified was obtained from Sigma Aldrich and were of reagent or higher grade.

His-Tag Removal—

LEDGF$_{1-326}$ gene was amplified from pLEDGF$_{1-326}$ plasmid using 5'AGCAAGCC ATGGGCATGACTCGCGATTTCAAACCTGGA3' (SEQ ID NO: 5) and 5' AGCAAGAAGCTTCTACTGCTCAG-TTTCCATTTGTTCCTC3' (SEQ ID NO: 6) primers containing NcoI and HindIII sites, respectively. The LEDGF$_{1-326}$ gene was thereafter ligated into pET-28a (+) after digesting with Nco1 and HindIII enzymes. The ligated product was transformed in competent *Escherichia coli* DH5α cells as per user's manual. The insertion of the gene was confirmed by PCR, restriction digestion and sequencing methods.

LEDGF$_{1-326}$ Biosynthesis and Purification:

LEDGF$_{1-326}$ (His-tag free) was biosynthesized and purified as previously described (Ref-JBC). Briefly, LEDGF$_{1-326}$ was expressed in *Escherichia coli* BL21 (DE3) using 1 mM IPTG. LEDGF$_{1-326}$ was purified from cell lysates using two step fast protein liquid chromatography (FPLC), first based on charge (cation exchange) and then based on size (gel filtration). The purified LEDGF$_{1-326}$ was extensively dialyzed in citrate-phosphate buffer pH 7.0, concentrated and stored at −80° C. until further use.

Formulation Preparation:

LEDGF$_{1-326}$ (1 or 0.5 mg/ml) formulation in citrate-phosphate buffer was made with pH ranging from 6 to 7.5. Additives Tween 20, EDTA, and sucrose was added to the final concentration of 0.1% (w/v), 1 mM, 10% (w/v), respectively. Formulation containing 0.02% sodium azide was tested for any degradation that might happen due to microbial growth. All formulations once prepared were stored at 25° C. in temperature controlled incubator and adequate measure was taken to avoid any evaporation.

Fluorescence Spectroscopy:

The steady state fluorescence spectroscopy was done to determine the changes in the tertiary structure. The intrinsic tryptophan (Trp) fluorescence spectra of formulations were recorded from 300 to 400 nm, at 280 nm excitation, with every 1 nm increment using Spectramax M5 (Molecular Devices, Downingtown, Pa.). To measure the changes in the fluorescence, fluorescence intensity at 342 nm was plotted for each pH and each time point. Buffer and inner filter effects were corrected for all fluorescence values.

Circular Dichroism (CD):

Secondary structural changes of LEDGF$_{1-326}$ was determined by far-UV CD spectra. Briefly, the formulation was placed in 1 mm quartz cuvette and spectra was recorded at a scan speed of 0.5 sec per time point, step size of 1 nm and the bandwidth of 4 nm from 200 to 280 nm using Chirascan® CD instrument (Applied Photophysics Ltd, UK).

Dynamic Light Scattering (DLS):

The size of the LEDGF$_{1-326}$ protein was monitored using Nano ZS (Malvern, Westborough, Mass.). Briefly 100 µl of formulation was placed in low volume glass cuvette. Using dynamic light scattering, LEDGF$_{1-326}$ particle scattering data were collected at 173° backscatter angle. An average of 13 scans were recorded for each measurement.

Sodium Dodecyl Sulfate-Polyacrylamide Gel Electrophoresis (SDS-PAGE):

The LEDGF$_{1-326}$ formulation samples (10 µg) were boiled for 10 min at 75° C. along with 10 µL of 2× loading buffer. Samples were loaded on 4-15% mini-PROTEAN TGX gels and proteins were size separated. Proteins were visualized using Coomassie Blue staining as per user's protocol.

Protein Estimation:

For protein estimation, LEDGF$_{1-326}$ formulation was spin down at 10000 g for 5 min and the supernatant was collected. Protein estimation of supernatant was done using BCA assay kit as per user's manual. For insoluble aggregate estimation, the soluble protein measured at each time point was subtracted from the day 0 protein levels of the corresponding formulation.

ELISA:

An indirect ELISA method was developed to determine the percentage of immuno reactive LEDGF$_{1-326}$ in formulations. Briefly, in 96-well plate, 100 µl of either standard LEDGF$_{1-326}$ (freshly purified) or formulation samples were coated overnight at 4° C. in triplicates. Wells were washed three times with wash buffer (0.1% w/v Tween 20 in PBS pH 7.0) after each step. The nonspecific binding sites were blocked with blocking solution (0.5% bovine serum albumin, and 0.1% Tween 20 in PBS pH 7.0) for 4 hours. LEDGF$_{1-326}$ was detected by mouse anti-LEDGF antibody (BD Biosciences, San Diego, Calif.) which was cross detected with HRP conjugated anti-mouse secondary antibody (source). After through washing of the plate finally 3,3',5,5'-Tetramethylbenzidine (TMB) was added. Immuno reactive LEDGF$_{1-326}$ was quantitate by colorimetric absorbance at 650 nm upon development of blue color.

Statistical Analysis:

All data are represented as the mean±SD. For comparison between multiple groups, data has been combined for all pH, averaged and compared to corresponding additive containing formulations. Statistics was done by one-way ANOVA followed by Tukey's post hoc analysis (SPSS, ver.11.5; SPSS, Chicago, Ill.). $p \leq 0.05$ was considered to be statistically significant.

2. Results

His Tag Free LEDGF$_{1-326}$ Cloning and Purification

PCR amplification led to band of 1000 bp of LEDGF$_{1-326}$. Restriction digestion, ligation and subsequent PCR amplification from LEDGF$_{1-326}$ gene inserted plasmid indicated a positive band of LEDGF$_{1-326}$. Purification of LEDGF$_{1-326}$ protein indicated a monomer band of 40 kDa along with very faint small molecular weight bands indicating LEDGF$_{1-326}$ might have undergone some degradation during purification process.

Additives Increases LEDGF$_{1-326}$ Stability

Figure 11:
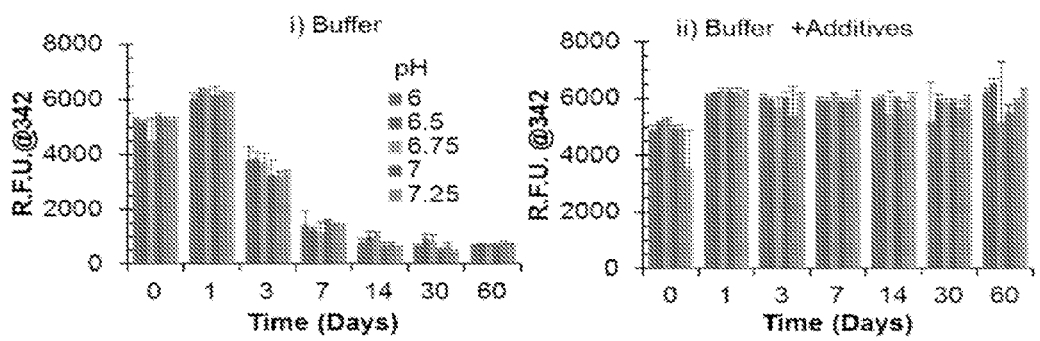
FIG. 11 A-C is a set of graphs showing LEDGF1-326 tertiary structure, secondary structure and size changes in absence or presence of additives
Figure 11:
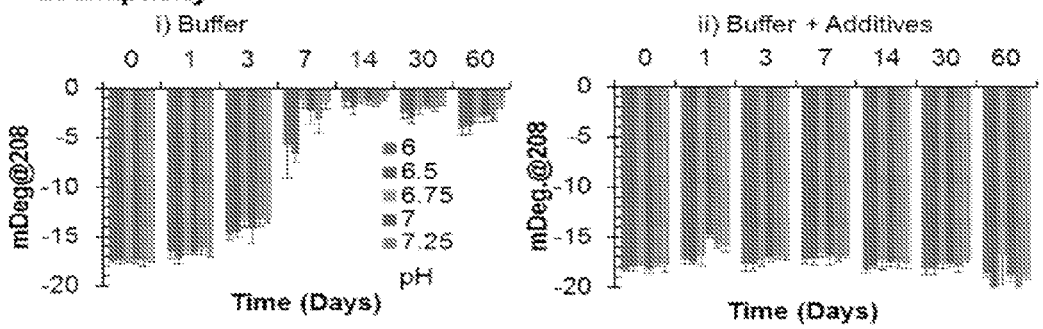
Figure 11:
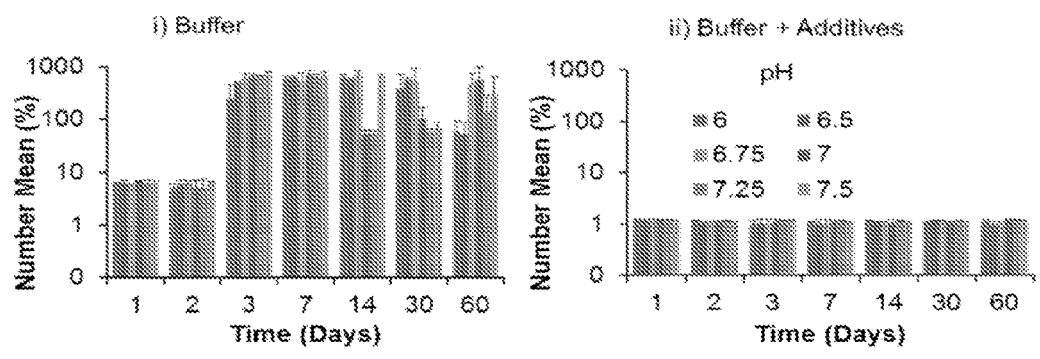

Effect of additives Tween 20, EDTA, and sucrose on LEDGF$_{1-326}$ stability was monitored in citrate-phosphate buffer between pH 6.0-7.5. The tertiary structure perturbation in LEDGF$_{1-326}$ was monitored by measuring the fluorescence behavior of tryptophan (Trp) in LEDGF$_{1-326}$ (FIG. 11A). LEDGF$_{1-326}$ formulation (0.5 mg/ml) indicated no significant difference in fluorescence intensity at 342 nm with respect to pH of the buffer (FIG. 11 A(i)). On day 0 plain buffer formulations of LEDGF$_{1-326}$ indicated initial fluorescence intensity of 5163±302 R.F.U. at 342 nm in 6.0-7.5 pH range. On day 1 there was an increase in fluorescence intensity to 6198±102 which decreased significantly to 3518±305 R.F.U. by day 3 indicating a loss of ~43% signal intensity as compared to day 1. By day 14 there was 87% loss in the signal intensity. The fluorescence spectra indicated red shift in the maximum fluorescence intensity on day 3, on day 7 and beyond the spectra were almost flat.

Additives did not change the initial LEDGF$_{1-326}$ fluorescence intensity and there was no significant difference in the fluorescence intensity of formulations with or without additives on day 0 (FIG. 11 A(ii)). There was no significant loss in the fluorescence signal as well as no shift in the fluorescence maxima until day 60 for all pH range.

The secondary structure perturbation in LEDGF$_{1-326}$ was monitored by CD. FIG. 11B indicates the ellipticity of LEDGF$_{1-326}$ at 208 nm for various formulations in 6.0-7.5 pH as function of time. CD indicated the secondary structure of LEDGF$_{1-326}$ is primarily random coil. LEDGF$_{1-326}$ indicated an ellipticity of −17.5±0.1 mDeg on day 0 which reduced significantly to −13.9±0.8 mDeg by day 3 (FIG. 11B(i)). There was further decline in the CD signal and by day 7 onwards the ellipticity was −3.4±2.3 mDeg. There was no significant difference in the CD signal in formulations with or without additives on day 0 (FIG. 11B(ii)). The CD signal on day 0 and day 60 was −17.9±0.3 and −19.1±1.4 mDeg, respectively, for all formulations containing additives indicating there were no significant changes.

The hydrodynamic (particle) size of LEDGF$_{1-326}$ was 7±1 nm on day 0 in all formulations with or without additives (FIG. 11C(i)) as indicated by DLS. By day 3 the particle size of LEDGF$_{1-326}$ increased to 200-700 nm in plain buffer formulations pH 6-7.5. In presence of additives, LEDGF$_{1-326}$ indicated a size of ~1 nm on day 0 and no change in size was indicated until day 60 (FIG. 11C(ii)).

Figure 12:
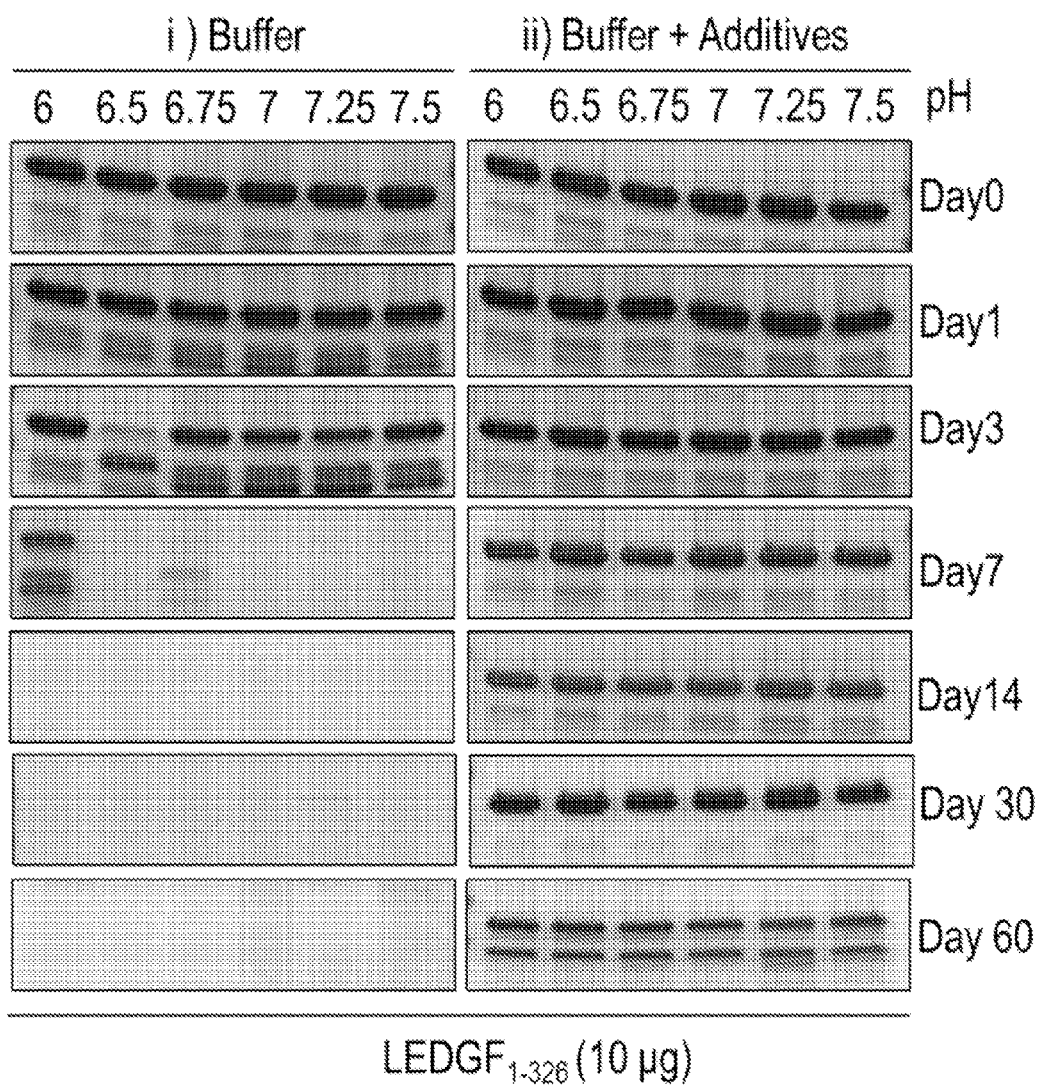
FIG. 12 is a picture of a SDS-PAGE gel of $LEDGF_{1-326}$ loaded under reducing conditions.

SDS-PAGE indicated LEDGF$_{1-326}$ is a 40 kDa protein. On day 0 there were very faint bands of small molecular weight proteins in all formulations. In plain buffer formulations the lower molecular weight fragments intensified as early as in day 1 (FIG. 12(i)). By day 3 there was significant amount of visible lower molecular weight bands. By day 7 there was complete loss of 40 kDa band and other fragments. Additives delayed the intensification of lower molecular bands until day 60 (FIG. 12(ii)). On day 60 lower molecular bands were visible along with the 40 kDa band in additive containing formulation irrespective of buffer pH.

Additives Reduces Insoluble Aggregates of LEDGF$_{1-326}$

Figure 13:
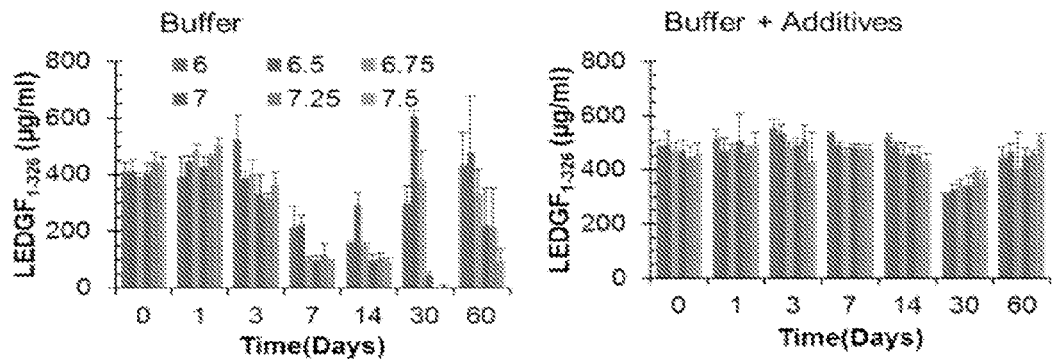
FIGS. 13A-B is a set of graphs showing quantities of soluble protein and insoluble aggregates of $LEDGF_{1-326}$ in the presence and absence of various additives.
FIG. 13C is a picture of microcentrifuge tubes showing absence of insoluble aggregates of $LEDGF_{1-326}$ in the presence of various additives.
Figure 13:
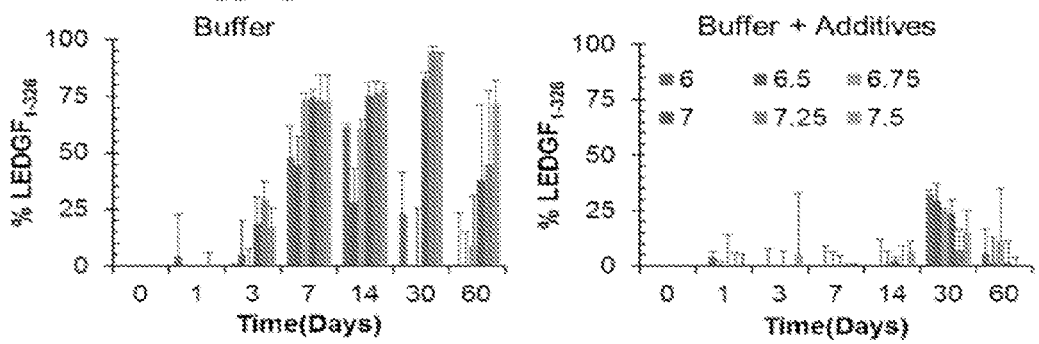
Figure 13:
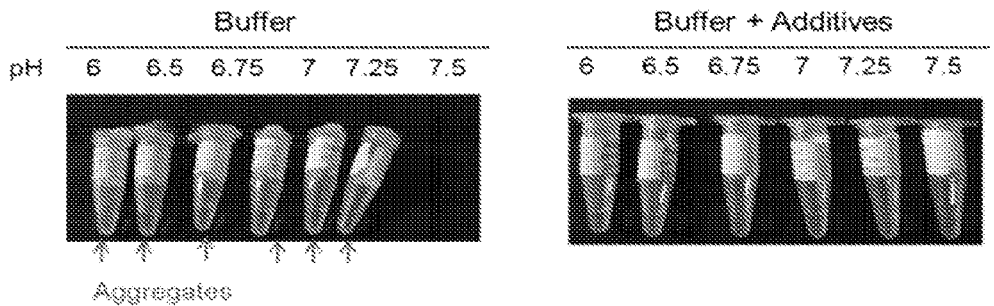

The soluble protein content on day 0 for LEDGF$_{1-326}$ plain buffer formulations pH 6.0-7.5 was 417.8±21.3 µg/ml (FIG. 13A). By day 7 there was significant decrease in the soluble protein content to 142.5±60.7 µg/ml. Thereafter, there was high variation in the protein content in plain buffer formulations at different pH, however there was no clear trend. On an average by day 60 the total soluble protein content was 316.2±140.0 µg/ml. Additives containing formulations indicated protein content of 470.5±17.3 µg/ml on day 0 and remained to be 469.0±33.4 µg/ml even until day 60.

Percentage aggregates present in the formulation was calculated from the soluble protein content (FIG. 13B). Plain buffer formulations indicated appearance of insoluble aggregates as early as day 3 and by day 7 there was 64.6±14.0% aggregates (FIG. 13B). Beyond day 7 there was unpredictable changes in the aggregate content in the formulation, however, presence of aggregates remained significantly high in all pH range. In presence of additives, the percentage aggregates remained below the detections limit for all days until day 60 except on day 30 where there was 22.3±9% aggregates (FIG. 13B).

Particles that settled down in the formulations were visible in plain buffer formulations (FIG. 13C), while the additive containing formulations were clear until day 60.

LEDGF$_{1-326}$ Remains Immunoreactive in Presence of Additives

Figure 14:
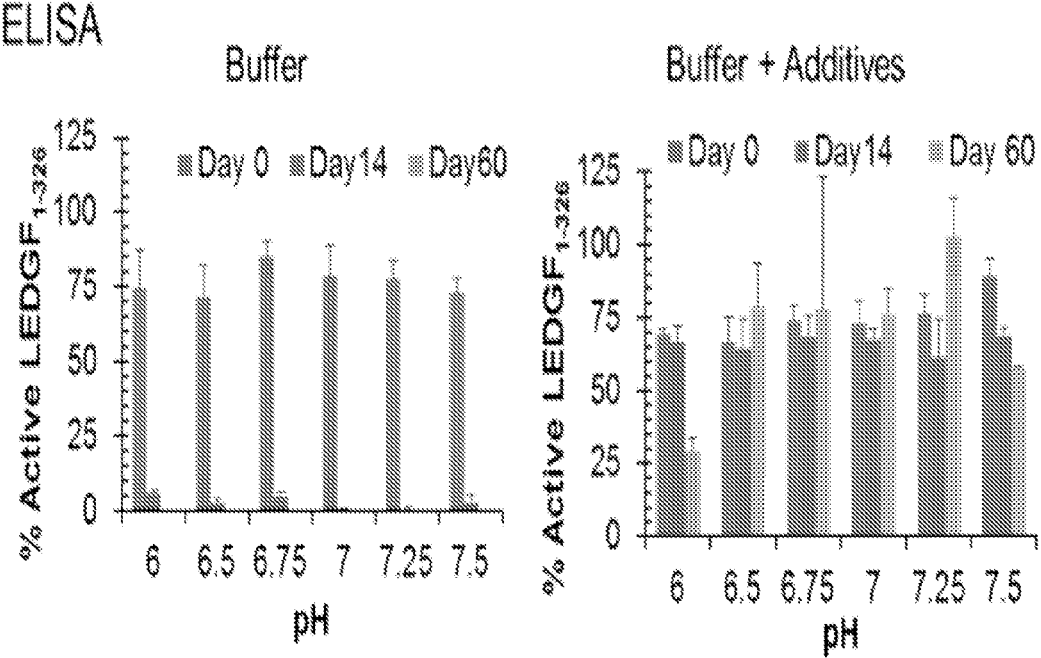
FIG. 14 are graphs depicting the immunoreactivity of LEDGF$_{1-326}$ in the presence and absence of various additives.

LEDGF$_{1-326}$ immuno reactivity was quantified using an indirect ELISA (FIG. 14). ELISA indicated 76.9±4.8% immuno reactive LEDGF$_{1-326}$ on day 0 in plain buffer formulations pH 6.0-7.5. On day 14 when immunoreactivity was tested it was found that LEDGF$_{1-326}$ lost almost all of its immunoreactivity with only 3.1±2.4% remaining By day 60 immunoreactive LEDGF$_{1-326}$ was undetectable. On the other hand additives containing formulations indicated 74.8±7.7, 66.2±2.8, and 70.4±24.5% immunoreactive LEDGF$_{1-326}$ on day 0, day 14, and day 60, respectively. The immunoreactivity was seen to have pH dependency, while pH 6, and 7.5 indicated 30±4 and 58±1% immunoreactive LEDGF$_{1-326}$, pH 6.5, 6.75, 7.0, and 7.25 indicated 78±15, 78±45, 76±9, and 102±13% immunoreactive LEDGF$_{1-326}$ on day 60.

Individual Additives are Less Effective in Increasing LEDGF$_{1-326}$ Stability

Figure 15:
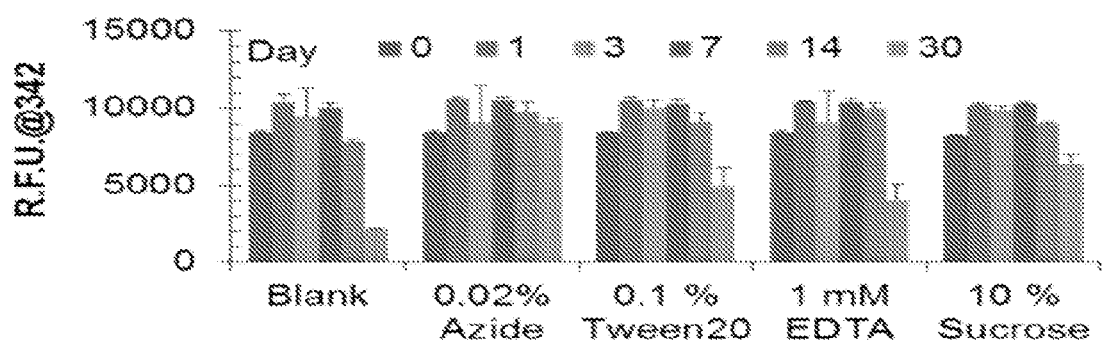
FIG. 15A-C is a set of graphs showing the biophysical characterization of structural integrity and conformational stability of LEDGF$_{1-326}$ in the presence of additives. A) Fluorescence intensity of LEDGF$_{1-326}$ at 342 nm with excitation at 280 nm as function of time in the presence of various additives. B) Circular dichroism (CD) of LEDGF$_{1-326}$ at 208 nm as a function of time and additives. C) Hydrodynamic size of LEDGF$_{1-326}$ as a function of time and additives.
Figure 15:
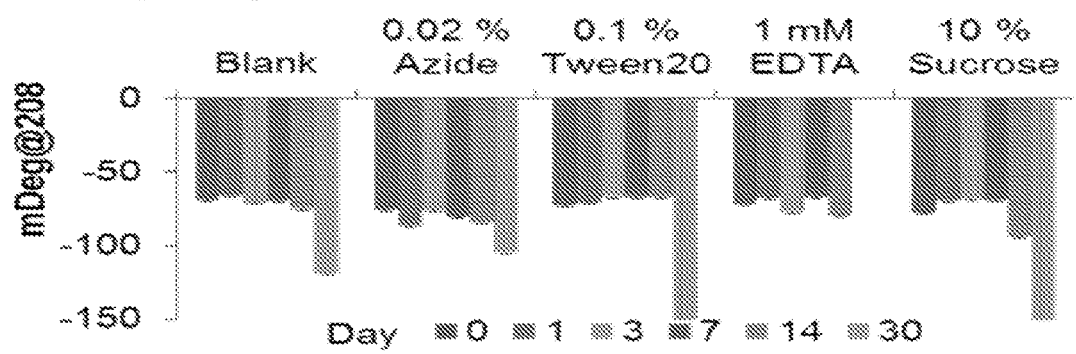
Figure 15:
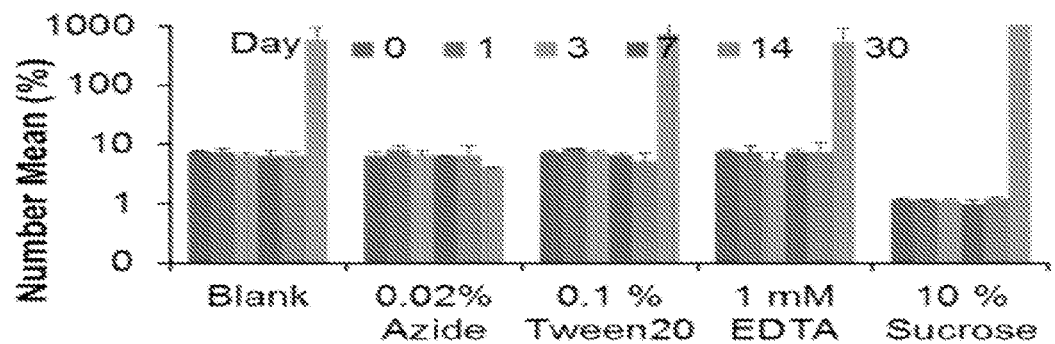
Figure 16:
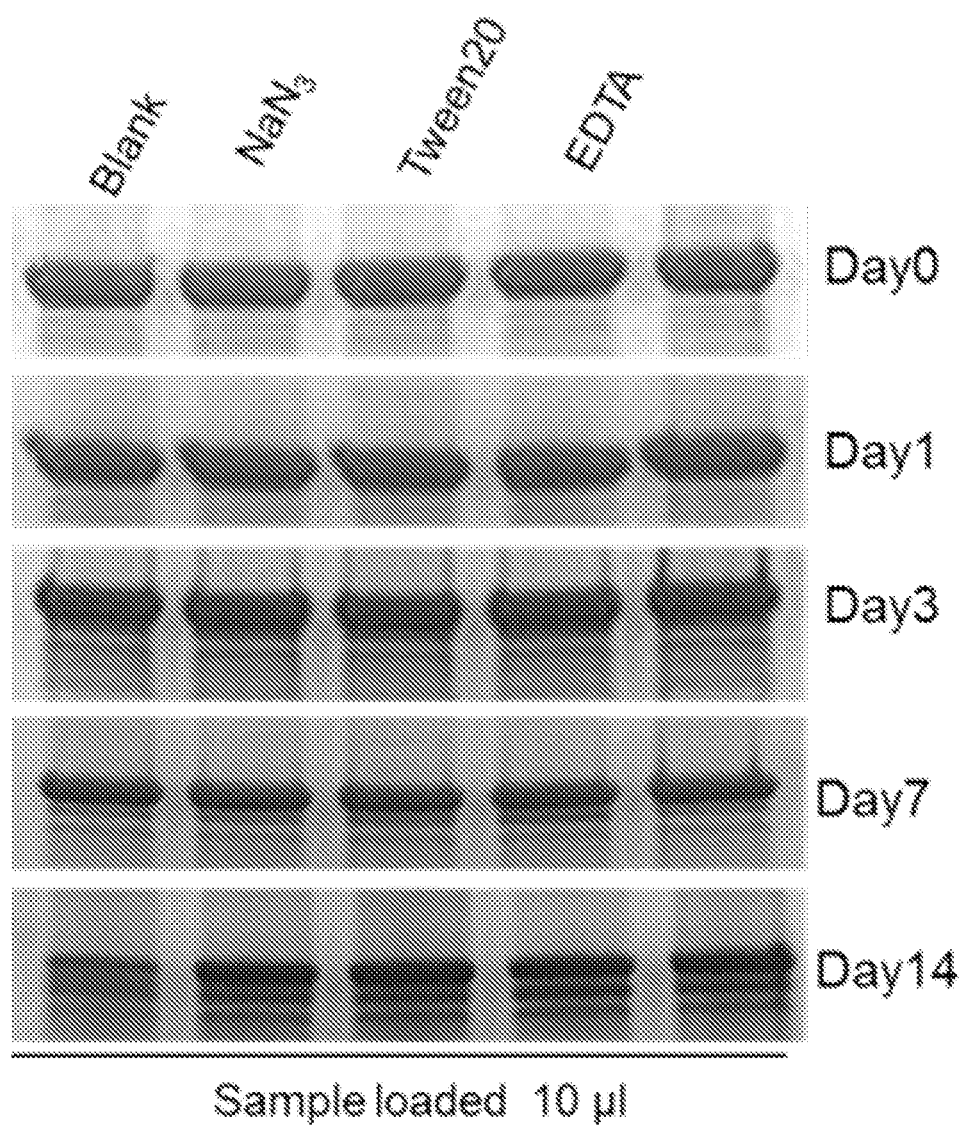
FIG. 16 is a picture of a SDS-PAGE gel providing a molecular weight analysis of LEDGF$_{1-326}$ as a function of time.

To understand the effect of individual additives on LEDGF$_{1-326}$ stability only one additive at a time was tested in LEDGF$_{1-326}$ (1 mg/ml) formulations at pH 7.0 (FIGS. 15, and 16). Fluorescence intensity of LEDGF$_{1-326}$ at 342 nm decreased from 8410±116 to 2178±22 R.F.U for plain citrate-phosphate buffer formulation by day 30 (FIG. 15A). While for 0.01% Tween 20, 1 mM EDTA, and 10% sucrose containing formulations, the fluorescence intensity was 4925±1249, 4056±979, and 6370±592 R.F.U., respectively on day 30. Sodium azide used as control to monitor the microbial contamination indicated fluorescence intensity of 9136±241 R.F.U. In absence of additive, LEDG$_{1-326}$ fluorescence signal lost was 75% of day 0 signal, Tween 20, EDTA, and sucrose retained the fluorescence signal to ~59, 48, and 76%, respectively. Similar to fluorescence, the CD signal also indicated LEDGF$_{1-326}$ instability (FIG. 15B).

On day 30 all formulations indicated significant difference in the ellipticity at 208 nm as compared to day 0 signal. There was a huge background signal noise indicating presence of non-native structures.

LEDGF$_{1-326}$ indicated a mean hydrodynamic size of 7±1 nm one day 0 for all formulations accept sucrose containing formulation (FIG. 15C). In presence of sucrose LEDGF$_{1-326}$ indicated hydrodynamic size of 1 nm. By day 30 particle size increased significantly to 578±366, 726±444, 490±423, and 1052±125 nm, for plain buffer, Tween 20, EDTA, and sucrose containing formulations, respectively. For sodium azide group, instead of increase in size there was decrease in size from 7 to 4 nm.

The monomeric native LEDGF$_{1-326}$ was monitored by SDS-PAGE (FIG. 16). Initially on day 0 the band intensity of LEDGF$_{1-326}$ at 40 kDa was similar in all groups. By day 7 there was thinning of 40 kda band indicating loss of LEDGF$_{1-326}$ monomers. On day 14 appearance of lower molecular weight bands in all groups were more pronounced as compared to day 0.

Example 3

1. Materials and Methods

ARPE-19 cells were obtained from American Type Culture Collection (ATCC; Manassas, Va.). Cell culture materials, reagents and Lipofectamine 2000 were obtained from Invitrogen Corporation (Carlsbad, Calif.). Chromic acid, HCl, NaOH and other supplies for circular dichroism were obtained from Fisher Scientific (Pittsburgh, Pa.). Tris base, ZnCl$_2$, EDTA (ethylene diamine tera acetic acid) were obtained from Sigma-Aldrich (St. Louis, Mo.).

Preparation of Nanoassemblies

Lyophilized LEDGF$_{1-326}$ was dialyzed extensively overnight in 25 mM Tris-HCl, 100 mM NaCl, pH 7.4 at 4° C. ZnCl$_2$ stock solution (100 mM) was prepared in same buffer. For nanoassembly preparation, zinc stock solution was diluted to final concentration of 0.1 mM, 1 mM, and 10 mM using 25 mM Tris-HCl, 100 mM NaCl, pH 7.4 and LEDGF$_{1-326}$ (final concentration 1 mg/ml) was added to it and incubated at 37° C. for 24 hr. LEDGF$_{1-326}$ with no zinc under similar conditions was kept as control. All solutions were filtered with 0.2 μm filter before preparation of formulations. Nano (xx) assembly indicates LEDGF$_{1-326}$ nanoassembly prepared with xx mM Zn(II).

Dynamic Light Scattering

Nanoassemblies homogeneity and size distribution was measured using zeta sizer Nano ZS (Malvern, Westborough, Mass.) based on dynamic light scattering (DLS). Briefly, sample was placed in 150 μl quartz cuvette and data was collected at 173° backscatter angle with eleven scans averaged for final size distribution plot. The time dependent variation in sizes of these nanoassemblies and their stability were monitored by measuring the number size distribution profile at different time points.

Fluorescence

The changes in the tertiary structure of LEDGF$_{1-326}$ were determined by measuring the steady state intrinsic fluorescence of tryptophan. The sample was placed in 150 μl of quartz cuvette and emission spectra were recorded from 300 to 400 nm, at 280 nm excitation wavelength, with an increment of 1 nm using Spectramax M5 (Molecular Devices, Downingtown, Pa.). Number of scans per data point was 6.

Circular Dichroism

To determine the secondary structural changes in LEDGF$_{1-326}$, far-UV CD spectrum of the formulations were recorded. Briefly, sample was placed in 1 mm quartz cuvette and spectra was recorded at a scan speed of 0.5 secs per time point, step size of 1 nm and the bandwidth of 4 nm from 200 to 280 nm using Chirascan® CD instrument (Applied Photophysics Ltd, UK). All scans were done in triplicate. The scans were subtracted for buffer component.

Cell Viability Assay

ARPE-19 cells were used to determine the cell survival function of LEDGF$_{1-326}$ in presence of aggregation mediated stress. Briefly, ARPE-19 cells were maintained as describer earlier (Baid et al. PLoS One. 6(9):e24616). For cell viability assay, 10000 cells were seeded in 96-well plate in serum containing DMEM-F12 media. After 24 hr, the medium was aspirated out and cells were washed with 100 μl of serum free medium. Thereafter, cells were treated with 200 μl of either LEDGF$_{1-326}$ alone or the LEDGF$_{1-326}$ +10 mM zinc nanoassemblies for 48 hr. No cells (just the media), cells with 25 mM Tris buffer as control for LEDGF$_{1-326}$ alone, cells with 25 mM Tris +10 mM zinc (equivalent to group containing highest amount of zinc) were maintained as control. The cells were incubated for 24, and 48 hr. Thereafter, the medium was aspirated out and 200 μl of fresh serum free medium was added. 20 μl of MTT reagent (3-(4,5-dimethylthiazol-2-yl)-2,5-diphenyl tetrasodium bromide, 5 mg/ml in PBS pH 7.4) was added to each well and further incubation was done for 3 hr at 37° C. The MTT containing medium was aspirated out and the formazan crystal formed was dissolved in 200 μl of DMSO. The absorbance of the color developed was measured at 570 nm using Spectramax M5. The percentage viability of groups was calculated with reference to the control group containing cells with no lipofectamine 2000. All groups were repeated as n=3.

Cell Uptake

ARPE-19 (50,000) cells were seeded in 24-well plate in serum containing DMEM-F12 medium. After 24 hr the medium was aspirated out and cells were washed with 100 μl of serum free medium. Thereafter, cells were treated with 200 μl of either LEDGF$_{1-326}$ or nano(10) assembly for 1 and 6 hr. Cells with 25 mM Tris buffer as control for LEDGF$_{1-326}$ alone, cells with 25 mM Tris +10 mM zinc (equivalent to group containing highest amount of zinc) were maintained as control. After 2 or 6 hr, cells were washed with 500 μl of cold PBS pH 7.4 twice followed by 2 washes of 500 μl of acid PBS pH 5. Thereafter, cells were lysed with 1% triton-x for 20 min at room temperature and scrapped and collected. Fluorescence was measured at 488 nm excitation and 519 nm emission.

Chelation

For investigating whether the formation of nanoassemblies can be reversed in presence of chelating agent, the nanoassemblies were allowed to be formed for 24 hr at 37° C. as described above. EDTA 500 mM stock solution was made using 25 mM Tris-HCl and 100 mM NaCl, pH 7.4. EDTA was added to final concentration of 50 mM to either LEDGF$_{1-326}$ or nanoassembly. It was incubated for 4 hr at room temperature, thereafter UV, fluorescence, and CD was taken as described above.

2. Results

Figure 17:
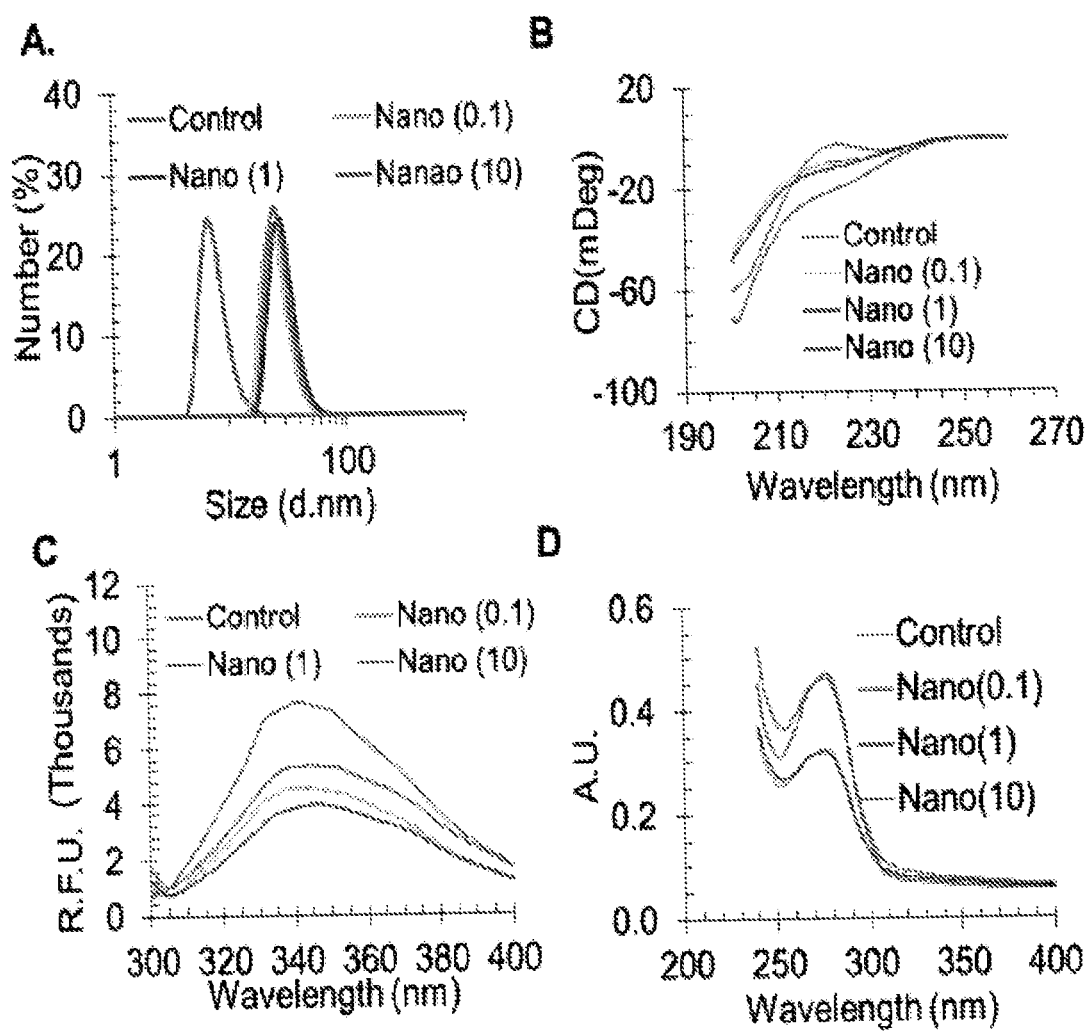
FIGS. 17A-D is a set of graphs showing formation of LEDGF$_{1-326}$ nanoassemblies in the presence of zinc. A) Dynamic light scattering. LEDGF$_{1-326}$ forms nanoassemblies in the presence of zinc. B) Circular dichorism. The secondary structure of LEDGF$_{1-326}$ is altered in the presence of zinc. C) Fluorescence spectroscopy. LEDGF$_{1-326}$ fluorescence spectra is quenched in the presence of zinc indicating the exposure of hydrophobic residues to more polar environment. D) Ultra violet spectroscopy: LEDGF$_{1-326}$ uv absorbance was quenched in the presence of 0.1 mM and 1 mM zinc but not with 10 mM zinc.

LEDGF$_{1-326}$ Undergoes Structural and Conformational Changes in Presence of ZnCl$_2$ Formation of nanoassemblies in presence of Zn(II) was monitored by dynamic light scattering (DLS), intrinsic trp-fluorescence, far-UV CD, and UV-vis spectra (FIG. 17). LEDGF$_{1-326}$ indicated a hydrodynamic diameter of 9±1 nm, which did not change significantly within the period of 24 hr as monitored by DLS (FIG. 17A). LEDGF$_{1-326}$ incubated with different concentration of Zn(II) underwent a change in size, indicating formation of nanoassemblies. With 0.1 mM ZnCl2 there no change in size until 24 hr. In presence of 1 mM and 10 mM Zn(II) LEDGF$_{1-326}$ indicated an increase in size within 30 min of incubation at 37° C. At 24 hr incubation, LEDGF$_{1-326}$ indicated a size of 7±1, 22±5, 26±5, and 28±5 nm for control, nano(0.1), nano(1), and nano(10) assemblies, respectively.

To investigate the changes in the secondary structure of LEDGF$_{1-326}$ in presence of Zn(II), the far-UV CD spectra of the LEDGF$_{1-326}$ was monitored from 200-260 nm (FIG. 17B). After 24 hr incubation at 37° C., LEDGF$_{1-326}$ indicated a negative ellipticity below 200 nm and a negative dip at 230 nm. Deconvolution of the spectra indicted that LEDGF$_{1-326}$ is primarily a random coiled structure. In presence of Zn(II) significant changes in CD spectra was indicated. The negative dip at 230 nm shifted towards left (to lower wavelength). The ellipticity of LEDGF$_{1-326}$ indicated increased negative signal as the concentration of Zn(II) increased. The change in the CD was dependent on the Zn(II) concentration, being slow for 0.1 mM Zn(II) and fastest for 10 mM Zn(II) formulation (data not shown). There was a shift in the negative dip at 230 nm towards lower wavelength in concentration dependent manner indicating possible formation of α-helix. However below 200 nm the negative signal also increased depending on the Zn(II) concentration. Deconvulation of CD spectra indicated 2% increase in the α-helix as compared to control in nano (10) formulation.

The intrinsic trp fluorescence spectrum of LEDGF$_{1-326}$ (FIG. 17C) indicated in presence of Zn(II) the intensity of the fluorescence signal decreased between 200-400 nm in presence of Zn(II). Interestingly the decrease in fluorescence signal was more in 0.1 mM Zn(II) formulation as compared to 10 mM Zn(II) formulation.

LEDGF$_{1-326}$ showed an A$_{max}$ at 276 nm in UV absorbance spectra. (FIG. 17D). In presence of Zn(II) there was a decrease in the UV signal for 0.1 and 1 mm Zn(II) formulation but no change was observed for 10 mM zinc formulation. The UV signal at 276 nm ($A_{max}$) was 0.47, 0.33, 0.32, and 0.46 for control, nano(0.1), nano(1), and nano(10) assemblies, respectively.

$LEDGF_{1-326}$ Forms Nanostructures

Figure 18:
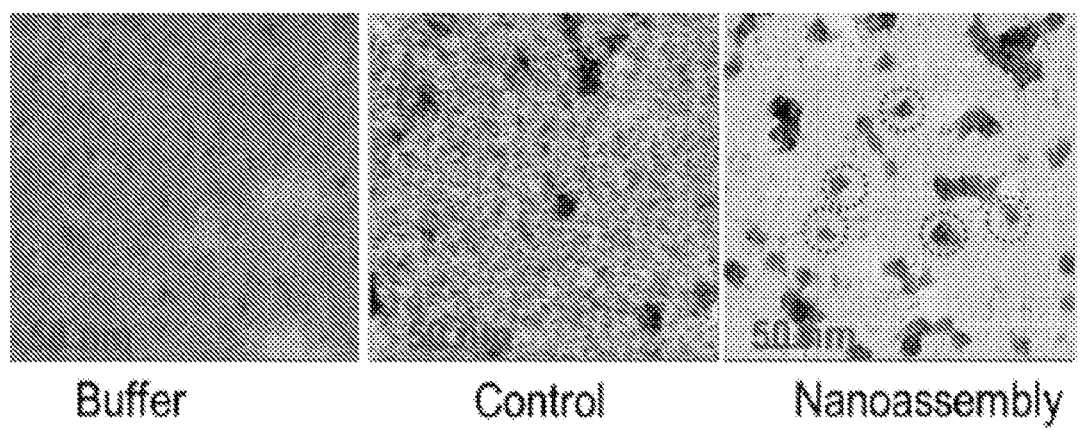
FIG. 18 is a set of TEM images of LEDGF$_{1-326}$ zinc nanoassemblies.

As shown in FIG. 18, $LEDGF_{1-326}$ nano (10) assemblies (right most panel) when visualized under transmission electron microscopy (TEM) indicated presence of loosely formed nanostructures as seen by dense negative stain. Some nanoassemblies clung to each other, while others were present as individual particle. In absence of Zn(II), $LEDGF_{1-326}$ (middle panel) did not indicate presence of any such structures.

Nanoassemblies is Stable Over Dilutions

Figure 10:
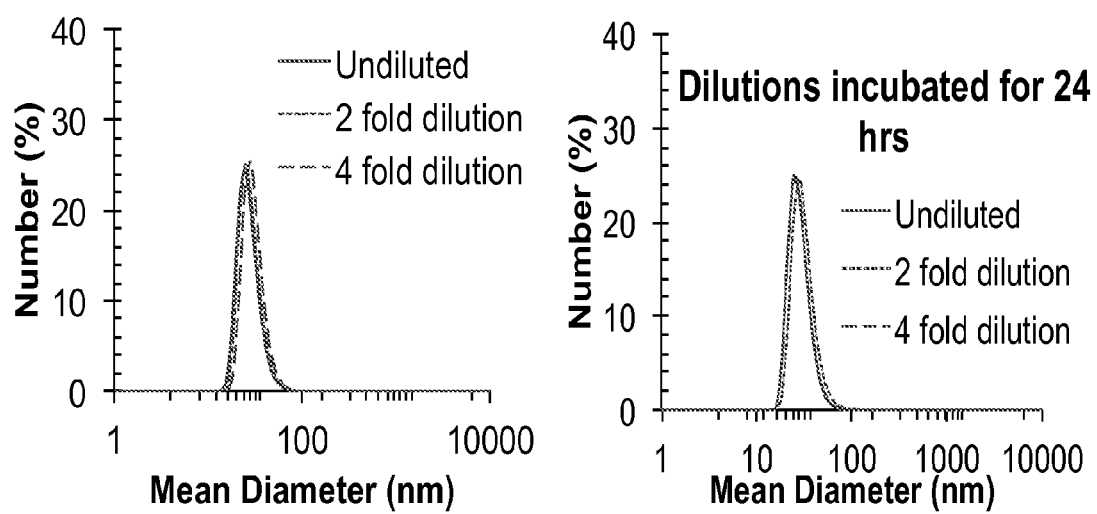
FIG. 10 is a set of graphs showing that $LEDGF_{1-326}$/zinc nano-assemblies are stable after dilution.

Stability of nanoassemblies over dilution was studied using DLS (FIG. 10). Nano (10) assemblies once formed did not indicate any change in size when diluted 2 and 4 times. Further, when these diluted nano (10) assemblies were stored at 4° C. for 24 hr and then size taken there was no change in size.

Formation of Nanoassembly is Reversible

Figure 19:
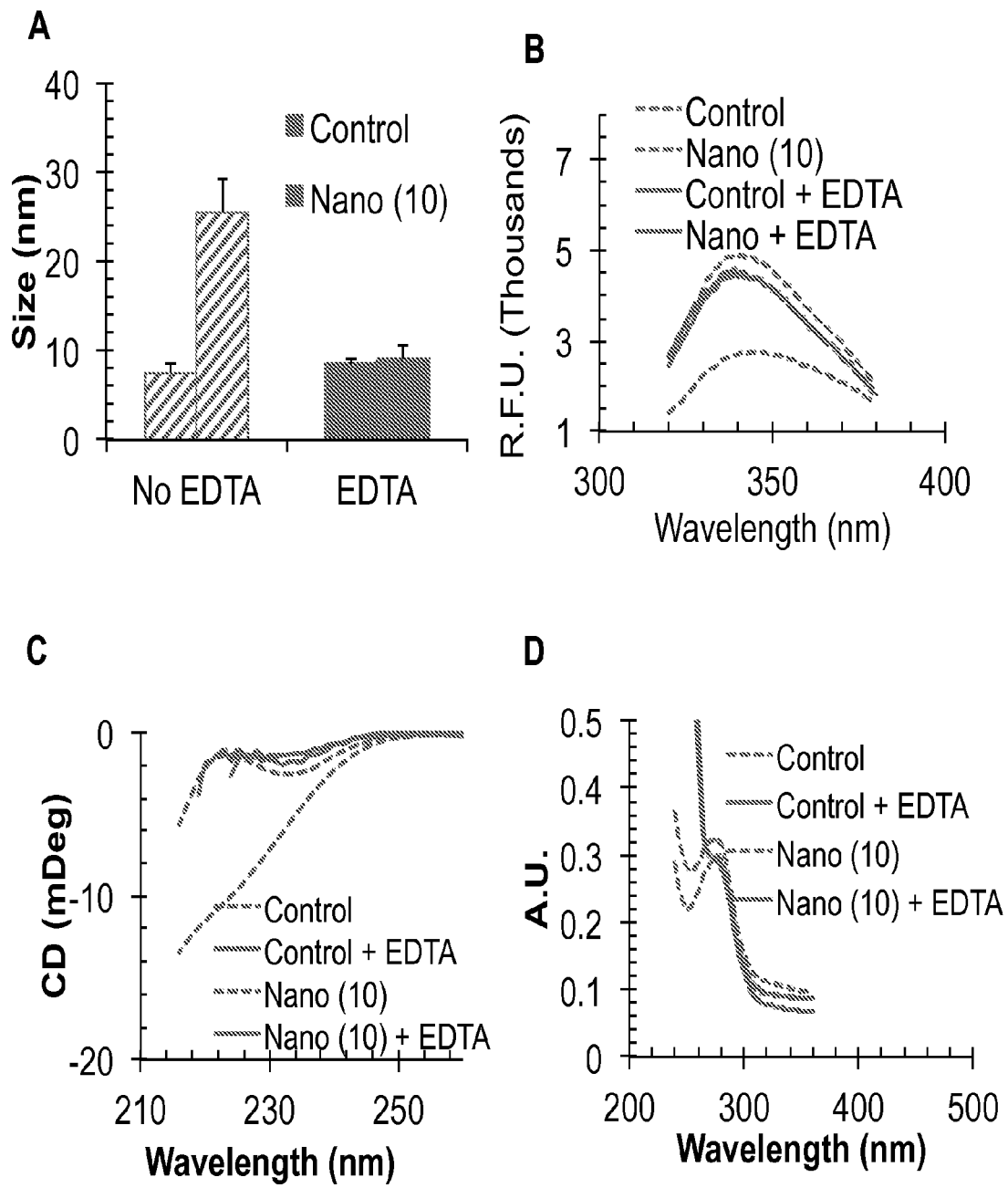
FIGS. 19A-D is a set of graphs demonstrating the reversible formation of LEDGF$_{1-326}$ nanoassemblies.

To investigate the kind of interaction between $LEDGF_{1-326}$ and zinc, we monitored the effect of EDTA on nano (10) (FIG. 19). Addition of EDTA to control $LEDGF_{1-326}$ did not indicate any significant size change and $LEDGF_{1-326}$ size remained to ~7-8 nm (FIG. 19A). Before addition of EDTA, nano (10) assembly indicated size of 25±4 which decreased to 9±2 upon EDTA addition. The fluorescence spectrum of nanoassembly which was quenched due to formation of nanoassembly reverted back (FIG. 19B). After addition of EDTA, control and nano (10) assemblies indicated similar fluorescence spectrum. All changes in the secondary structure as indicated by CD spectrum were similarly reverted (FIG. 19C). UV-vis spectrum also indicated reversal of changes that occurred due to assembly formation (FIG. 19D).

$LEDGF_{1-326}$ Stability is Increased in Nanoassemblies

Figure 20:
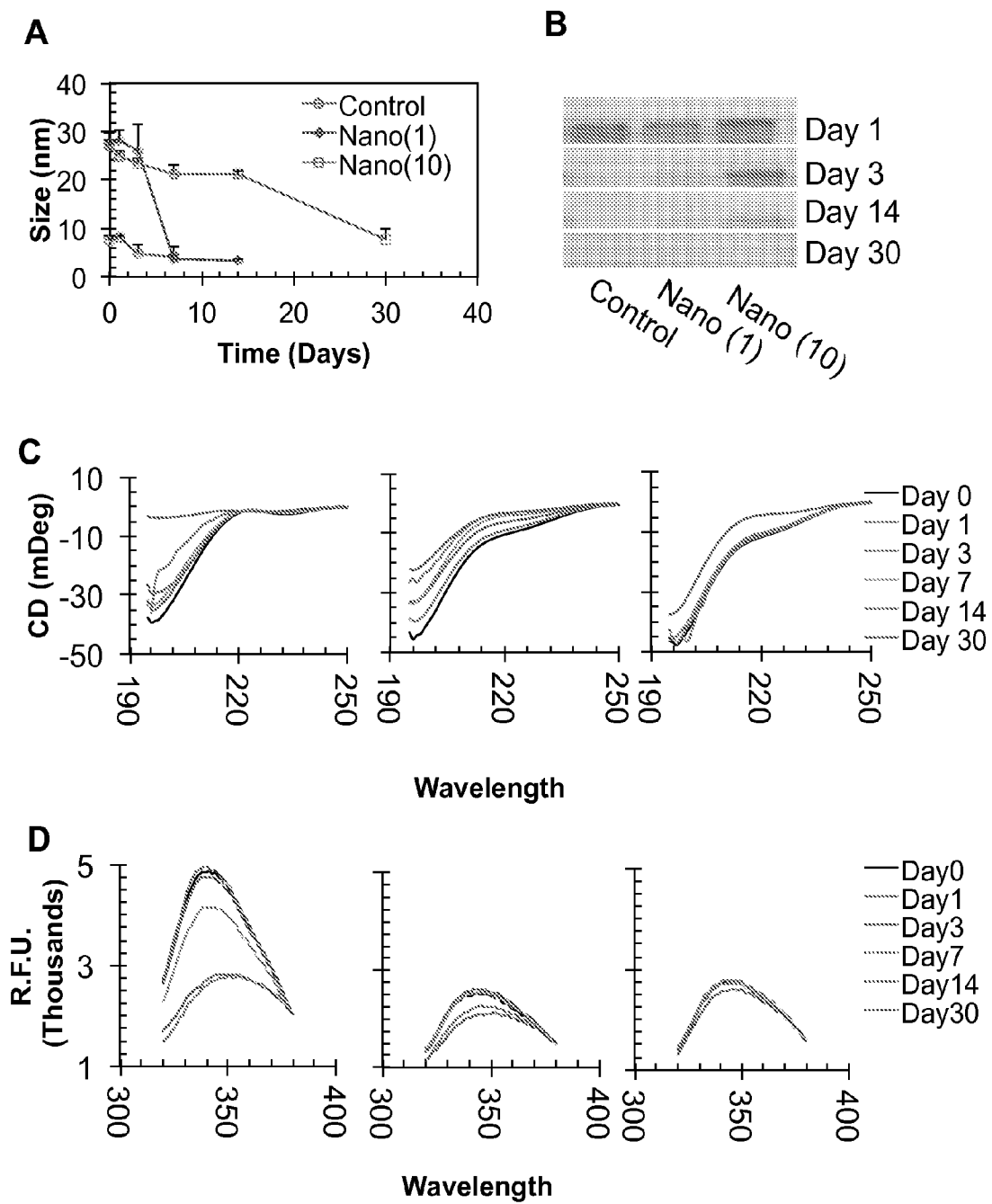
FIGS. 20A-D is a set of graphs and an image of an SDS-PAGE gel demonstrating the increased stability of LEDGF$_{1-326}$ nanoassemblies over time.

The stability of $LEDGF_{1-326}$ in nanoassemblies at 25° C. was monitored for 30 days using DLS, SDS-PAGE, CD, and fluorescence (FIG. 20). Control $LEDGF_{1-326}$ size decreased from 8±1 to 5±1 nm on day 3 (FIG. 20A). Nano (1) assemblies indicated size of 27±1 at day 0 which decreased to 4±3 nm on day 7. On the other hand nano (10) assemblies indicated no change in size until day 30. On day 30 there was a size change from 27±1 to 8±2 nm for nano (10) assemblies.

A 40 kDa band was indicated in SDS-PAGE in control $LEDGF_{1-326}$, nano (1) and nano (10) assemblies on day 0 (FIG. 20B). By day 3 there was complete loss of this band in control $LEDGF_{1-326}$. Nano (1) assemblies lost this band on day 7 while Nano (10) lost it on day 30.

The CD spectrum of control $LEDGF_{1-326}$ indicated a continuous loss in negative ellipticity from day 1 onwards and complete loss of signal on day 30 (FIG. 20C). Nano (1) assemblies indicated a continuous CD signal loss from day 1 onwards; however until day 30 there was CD signal. There was no significant signal loss in nano (10) assemblies until day 14, on day 30 there was decrease in CD signal, however the negative signal was still seen distinctively.

The fluorescence spectrum of control $LEDGF_{1-326}$ indicated significant decrease in fluorescence intensity on day 7 as compared to day 0, further fluorescence loss continued day 30 (FIG. 20D). Nano (1) assemblies on the other hand indicated no loss in fluorescence signals until day 7 as compared to day 0 signals, however on day 14 and onwards there was a signal loss. Nano (10) being most robust indicated no loss in intensity until day 14 as compared to day 0 signal and very less decrease in the intensity on day 30 as compared to other corresponding groups.

ARPE-19 Cells Take Up Higher Amount of Nanoassemblies

Figure 21:
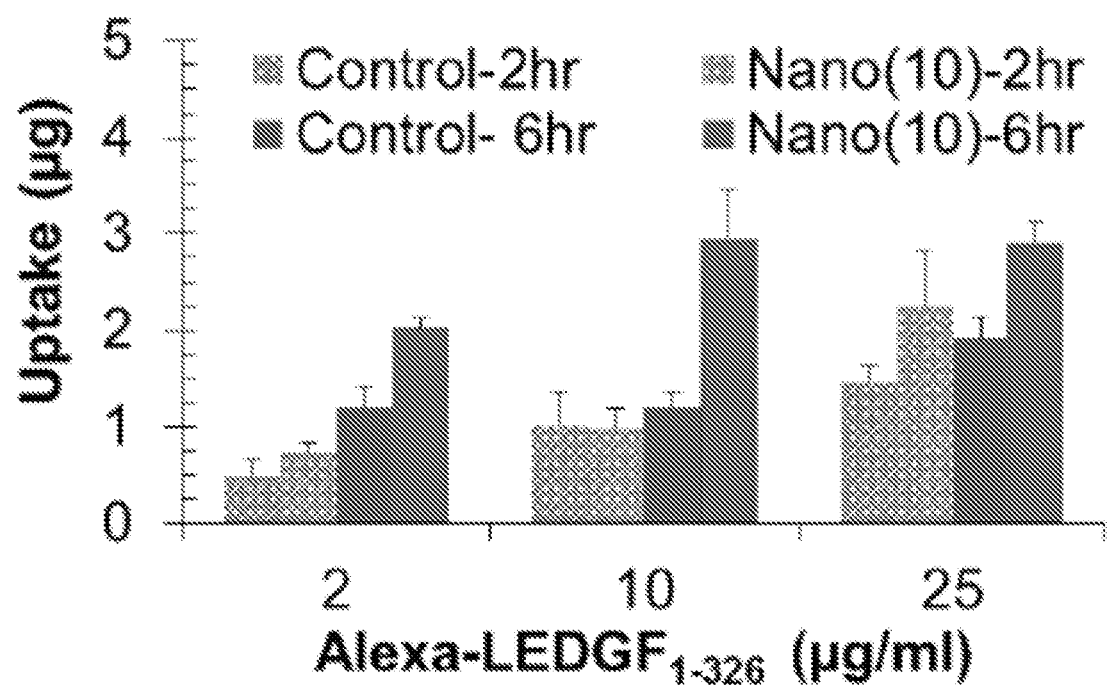
FIG. 21 is a graph demonstrating increased uptake of LEDGF$_{1-326}$ nanoassemblies by ARPE-19 cells.

The cellular uptake of $LEDGF_{1-326}$ was investigated in ARPE-19 cells using Alexa conjugated $LEDGF_{1-326}$ (FIG. 21). ARPE-19 uptake of Alexa-$LEDGF_{1-326}$ was dose dependent. Within 2 hr, 0.5±0.1, 1.0±0.3, and 1.4±0.2 µg of Alexa-$LEDGF_{1-326}$ (control) was taken up by ARPE-19 cells when incubated with 2, 10, and 25 µg/ml of Alexa-$LEDGF_{1-326}$, respectively. When incubation time was increased to 6 hr, there was an increase in the uptake of Alexa-$LEDGF_{1-326}$. $LEDGF_{1-326}$ uptake increased to 1.2±0.2, 1.2±0.2, and 1.9±0.2 µg in 6 hr for 2, 10, and 25 µg/ml of Alexa-$LEDGF_{1-326}$ treatment, respectively.

Alexa-$LEDGF_{1-326}$ nano (10) assemblies indicated higher uptake at 2, and 6 hr as compared to corresponding control groups. At 2 hr there was 0.7±0.08, 1.0±0.2, and 2.2±0.5 µg uptake for 2, 10, and 25 µg/ml of nano (10) assembly treatment, respectively. Although nanoassembly uptake was higher as compared to control, there was no significant difference. Increasing the incubation time from 2 hr to 6 hr increased nano (10) assembly uptake significantly. The uptake of was 2.0±0.09, 2.9±0.5, and 2.9±0.2 µg at 6 hr for 2, 10, and 25 µg/ml of nano (10) assembly treatment, respectively.

Nanoassemblies Survives ARPE-19 Cells from Serum Starvation

Figure 22:
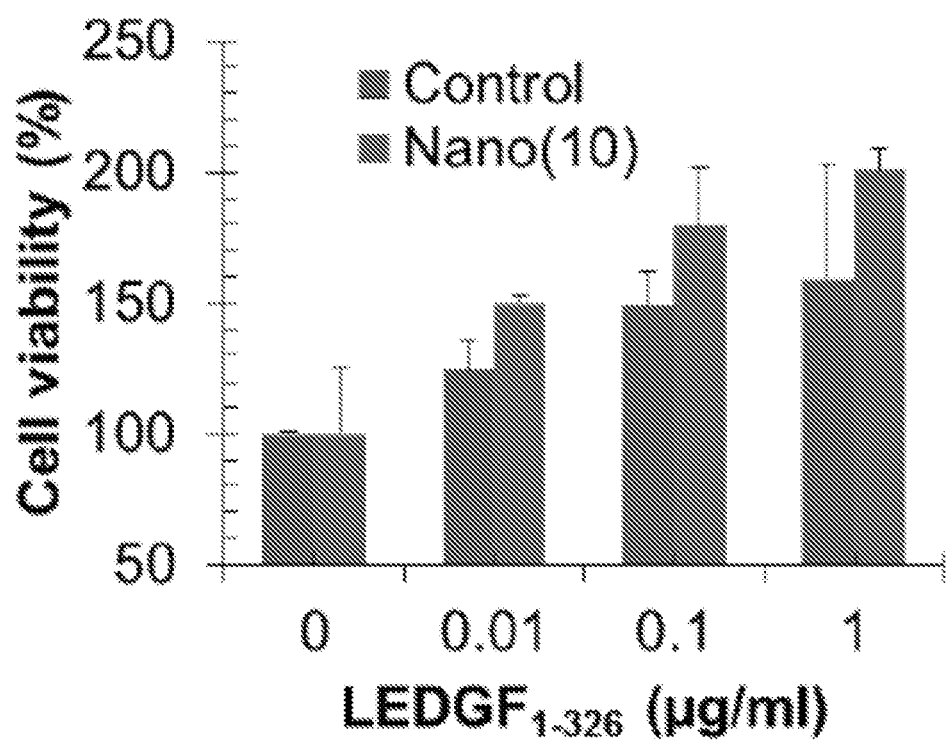
FIG. 22 is a graph depicting the results of a MTT assay demonstrating the ability of LEDGF$_{1-326}$ nanoassemblies to rescue ARPE-19 cells from serum starvation.

Efficacy of nanoassemblies to survive ARPE-19 cells under serum starvation was monitored by MTT assay. (FIG. 22). Compared to untreated groups (100% viability), $LEDGF_{1-326}$ treated group indicated an increase in viability in dose dependent manner. ARPE-19 cell viability increased to 124±11, 148±12, and 160±44% with treatment of 0.01, 0.1, and 1.0 µg/ml of $LEDGF_{1-326}$ treatment, respectively. Nano (10) assemblies treated group indicated higher cell viability compared to corresponding control $LEDGF_{1-326}$ treated groups. ARPE-19 cell viability increased to 150±3, 180±22, and 200±8% with treatment of 0.01, 0.1, and 1.0 µg/ml of $LEDGF_{1-326}$ treatment, respectively.

Figure 23:
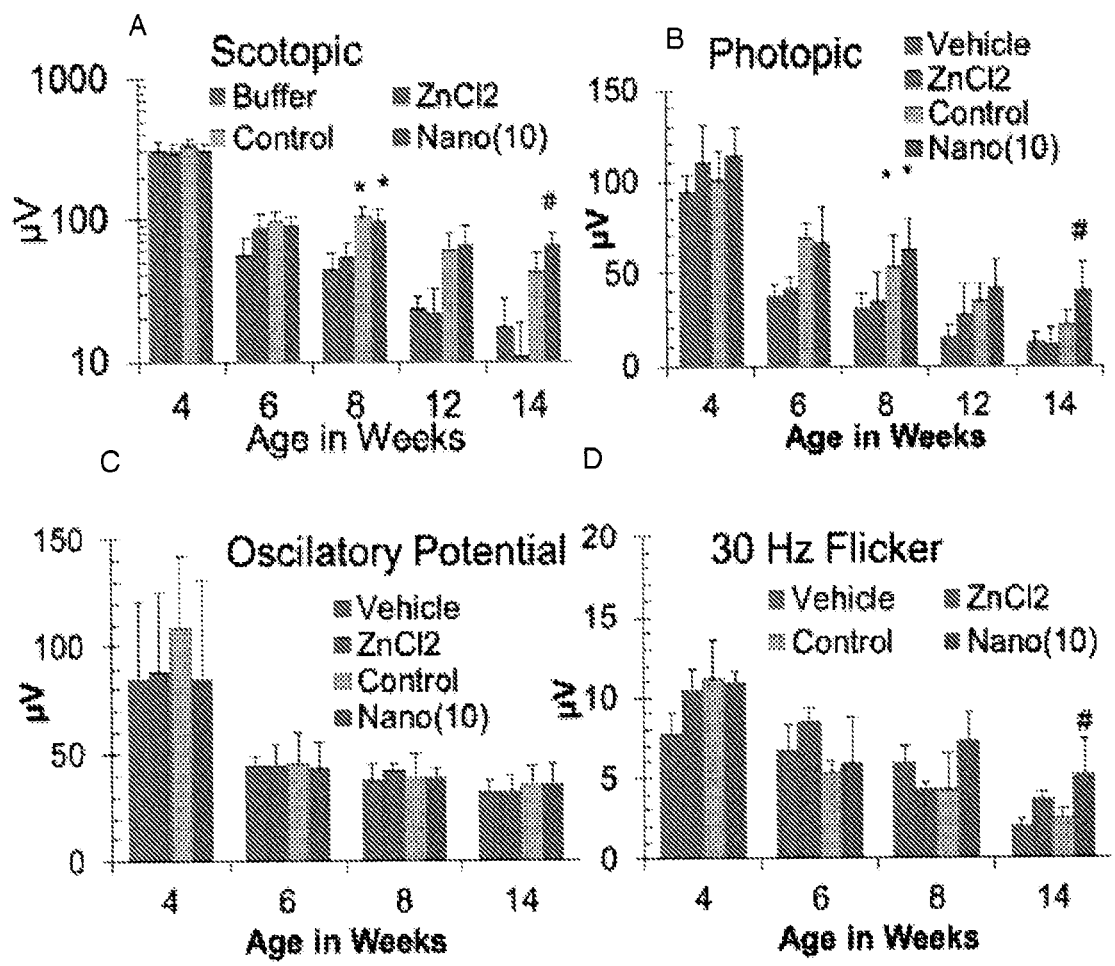
FIGS. 23A-D is a set of graphs demonstrating the ability of LEDGF$_{1-326}$ nanoassemblies to reduce retinal degeneration as examined using electroretinography.

Nanoassembly Increases $LEDGF_{1-326}$ Efficacy in Delaying Retinal Degeneration Efficacy of nanoassemblies to prevent the functional loss in retina was tested in RCS rats using electroretinography (ERG) (FIG. 23A). On week 4, before the intravitreal injection was given to rats, the b-wave amplitude was 313±32 µV, with no significant difference in all groups. Over a period of subsequent 10 weeks i.e. at 14 week the buffer and Zn(II) treated group indicated a decrease in b-wave amplitude from 307±44 to 17±10 and 302±37 to 11±7 µV, respectively. $LEDGF_{1-326}$ treatment (control) slowed the loss in the b-wave amplitude and on $14^{th}$ week the b-wave amplitude declined from 337±30 to 42±15 µV, however, there was no significant difference in the buffer, Zn(II) and, control group b-wave amplitude in week 14. Nano (10) indicated a significant protection against the loss of b wave amplitude until 14 week. The b-wave amplitude declined from 305±36 to 65±15 µV on week 14 indicating significantly high b-wave as compared corresponding buffer or Zn(II) group.

On week 4 the b-wave amplitude of all groups was 105±23 in photopic ERG (FIG. 23B). Similar to scotopic ERG, a decrease in b-wave amplitude was seen. The buffer and Zn(II) treated groups indicated a loss in b-wave amplitude from 94±26 to 12±7 and 109±23 to 11±7 µV, respectively. Control $LEDGF_{1-326}$ and nano (10) assemblies treated group delayed the loss, and the b-wave amplitude decreased from 100±28 to 22±5 and 113±23 to 40±10 µV, respectively. Nano (10) assemblies indicated significantly higher b-wave as compared to corresponding buffer, Zn(II) and control LEDGF$_{1-326}$ treated group.

Further oscillatory potential (OP) amplitude in all groups was 91.8±11.5 µV at week 4. (FIG. 23C). There was decrease in (OP) amplitude was seen across all groups. By week 14 the OP amplitude was 32±5, 33±8, 36±8, and 36±9 µV, in buffer, Zn(II), control, and nano (10) assembly group, respectively. There was no significant difference in all groups.

The 30 hz flicker amplitude was also measured. (FIG. 23D). On week 4 the flicker amplitude was on an average 10±2 µV for all groups. As with any other ERGs there was decease in the flicker amplitude in all groups; however on week 14 the flicker amplitude of nano (10) assembly group was significantly higher than buffer, and Zn(II) group. The flicker amplitude values on week 14 was 2±0.4, 3.7±0.4, 2.4±0.6, 5.2±2.2 µV for buffer, Zn(II), control and nano (10) assemblies, respectively.

Nanoassembly Increases LEDGF$_{1-326}$ Persistence for Days in Ocular Tissues

Figure 24:
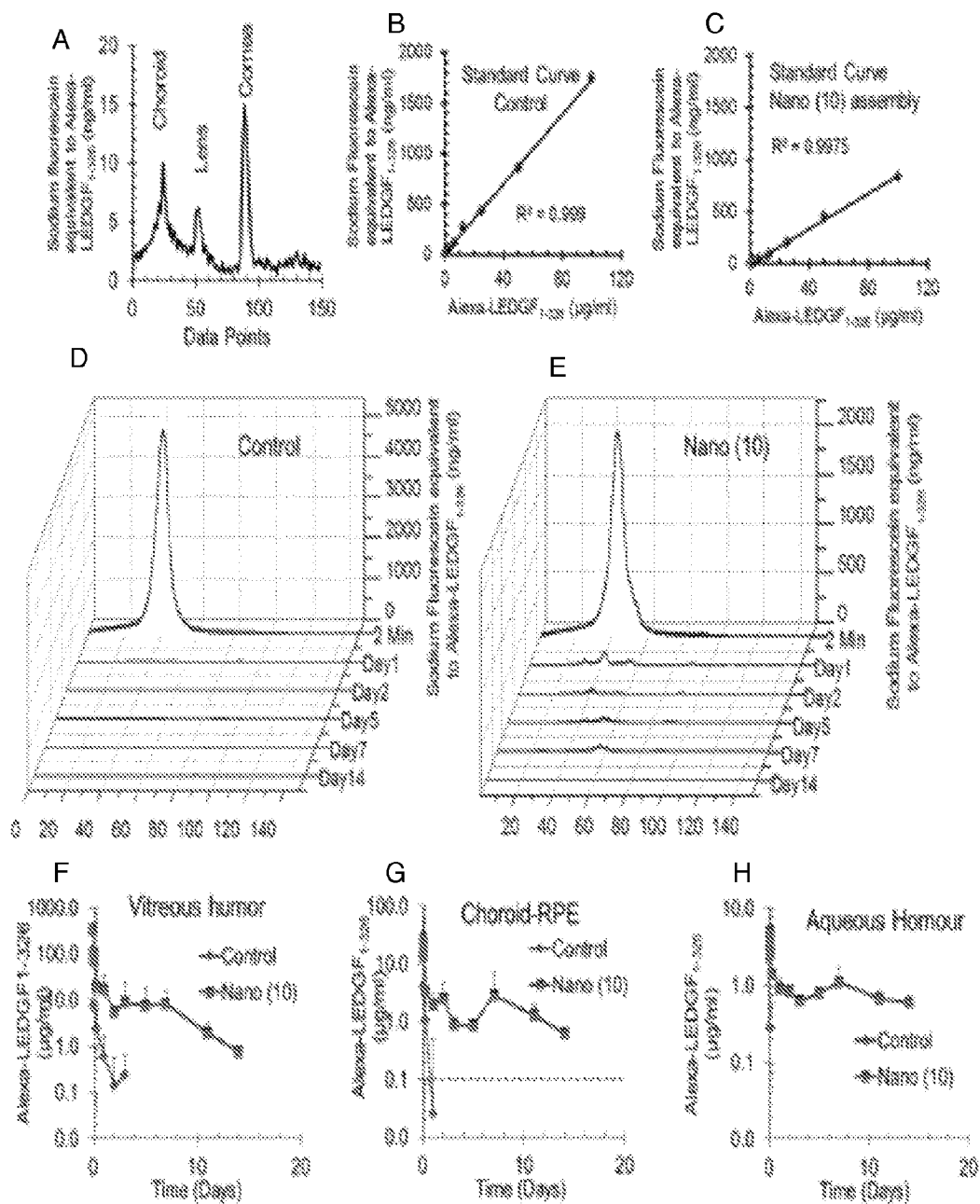
FIGS. 24A-H is a set of graphs demonstrating the persistence of LEDGF$_{1-326}$ nanoassemblies in vitreous for at least 14 days as measured by detecting the fluorescence signal of Alexa-LEDGF$_{1-326}$ in normal SD rats. A) Demonstrates the results of a blank scan before intravitreal injection of the SD rat eye. B) and C) demonstrate the standard curve for control and LEDGF$_{1-326}$ assemblies respectively. D) and E) demonstrate the fluorescence signal in various tissues including vitreous, choroid-RPE, and aqueous humor as obtained from the Flurotron scans; F), G), and H) convert the fluorescent signal measured above to actual LEDGF$_{1-326}$ nanoassemblies for vitreous, choroid-RPF, and aqueous humor respectively.

Persistence of LEDGF$_{1-326}$ in normal SD rat was measured using the fluorescence signal of Alexa-LEDGF$_{1-326}$ (FIG. 24). FIG. 24A indicates an average of blank scan (n=7) before the intravitreal injection of the SD rat eye. The blank scan indicated autofluorescence of choroid, lens, and cornea at about 24, 50, and 88 data points, respectively. Based on this blank scan data points were assigned to various tissues of the eye. The data points assigned were—Choroid-RPE-24, vitreous humor ~40, lens-50, aqueous humor ~70, and cornea-88. FIGS. 24B and 32C is the standard curve for control and nano(10) assembly. This was used to convert the fluorescence signal obtained in term of sodium fluorescein (NaF) concentration (ng/ml) from the Flurotron scans to actual Alexa-LEDGF$_{1-326}$ concentration (µg/ml). FIGS. 24D and 24E are Flurotron scans (N=4) for control and nano (10) assembly groups from 2 min to 14 days after intravitreal injection. The fluorescence signal in vitreous, choroid-RPE, and aqueous humor was obtained from the Flurotron scans (FIGS. 24D, and 24E) and was converted to actual Alexa-LEDGF$_{1-326}$ concentration in FIGS. 24F, 24G, and 24H, respectively. A high peak in the vitreous at 2 min of injection in FIGS. 24C, and 24D indicated intravitreal injection was rightly done.

A fluorescence signal equivalent to 3±0.5 ng/ml of NaF was observed in vitreous in blank scans (FIG. 24A) which when converted resulted in 0 µg/ml of Alexa-LEDGF$_{1-326}$ as base line. After 2 min of the intravitreal injection, a peak value of 292±106 µg/ml of Alexa-LEDGF$_{1-326}$ was indicated in the vitreous for control, which sharply declined to 127±74 µg/ml in 30 min (FIG. 24F). By day 3 the Alexa-LEDGF$_{1-326}$ peak in control groups was below the base line. Nano (10) assembly on the other hand indicated days of persistence. The peak concentration after 2 min of injection was 321±54 µg/ml of Alexa-LEDGF$_{1-326}$, there was initial rapid decline to 100±45 µg/ml in 30 min; thereafter the decline was slow as compared to control and persistence of nanoassembly in vitreous was indicated until day 14. On day 14 Alexa-LEDGF$_{1-326}$ concentration was 0.7±0.1 µg/ml in the nano (10) assembly group which was significantly higher than control group and the base line.

Persistence of Alexa-LEDGF$_{1-326}$ was also indicated in the choroid-RPE as well as in aqueous humor for the nano (10) assembly group. The autofluorescence in the choroid RPE indicated 10±4 ng/ml of NaF, which when converted to Alexa-LEDGF$_{1-326}$ concentration was 0.1 µg/ml. Thus 0.1 µg/ml of Alexa-LEDGF$_{1-326}$ was considered as base line for Choroid-RPE (FIG. 24G). Soon after intravitreal injection 13.2±10.8 µg/ml of ALexa-LEDGF$_{1-326}$ was indicated in choroid-RPE which increased to 30.0±22.6 µg/ml in 30 min in control group. Thereafter, there was decline in Alexa-LEDGF1-326 level and was undetectable by day 1. Nano (10) assembly on the other hand indicated 14.3±9.8 µg/ml of Alexa-LEDGF$_{1-326}$ in 2 min which increased to 21.5±12.8 µg/ml in 30 min. By day 1 Alexa-LEDGF$_{1-326}$ level dropped to 2.0±1.1 µg/ml, however it was significantly high from the base line an control group. Alexa-LEDGF$_{1-326}$ level remained significantly high until day 14 and was detected to be 0.6±0.2 µg/ml on day 14.

In aqueous humor the base line calculated from the blank scan was equivalent to 0 µg/ml of Alexa-LEDGF$_{1-326}$ (FIG. 24A). At 2 min after intravitreal injection, Alexa-LEDGF$_{1-326}$ concentration was 3.4±3 and 4.9±2.4 µg/ml for control, and nano (10) assembly group (FIG. 24H). Alexa-LEDGF$_{1-326}$ dropped below the base line within 6 hr for the control group, while the nano (10) assembly indicated presence of Alexa-LEDGF$_{1-326}$ until day 14, at this time point the concentration of Alexa-LEDGF$_{1-326}$ was 0.6±0.1 µg/ml.

Figure 25:
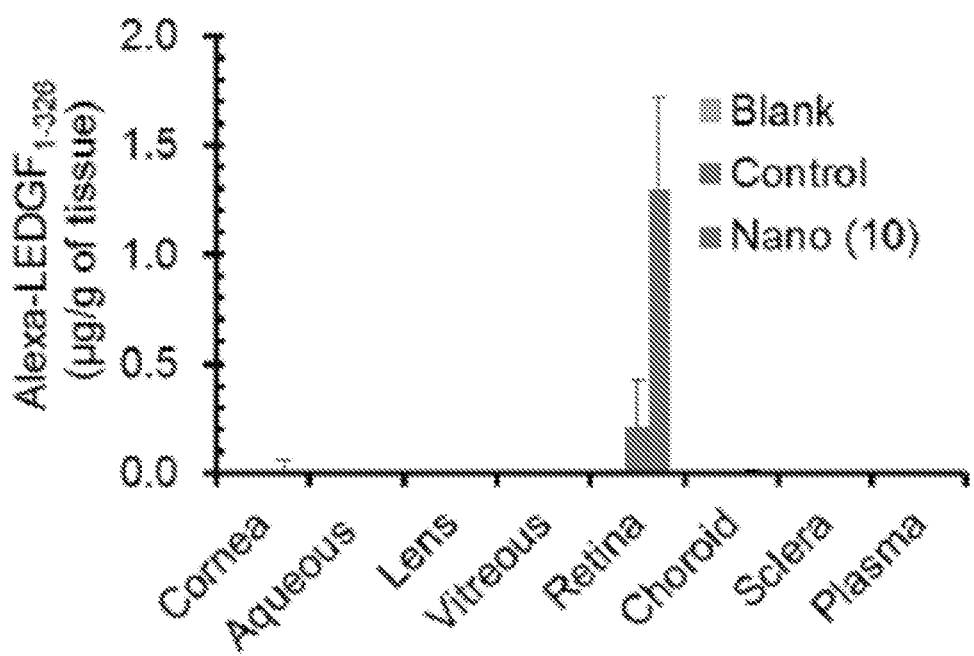
FIG. 25 is a graph demonstrating the ability of nanoassemblies to preserve the immunoreactivity of LEDGF$_{1-326}$.

LEDGF$_{1-326}$ Remains Immune Reactive In Vivo for Days when Dosed as a Nanoassembly Alexa-LEDGF$_{1-326}$ immunoreactivity was investigated in various ocular tissues and in blood after 14 days of single intravitreal injection by indirect ELISA (FIG. 25). There was no detectable level of Alexa-LEDGF$_{1-326}$ in the cornea, aqueous humor, lens, vitreous humor, retina, choroid-RPE, sclera and blood for the un-injected blank eye tissues indicating absence of any detectable quantity of endogenous LEDGF$_{1-326}$. Interestingly, Alexa-LEDGF$_{1-326}$ was detectable in retina for both control and nano(10) assembly group being 0.2±0.2 and 1.3±0.4 µg/g of tissue weight, respectively. There was no significant difference in the control and blank group, while nano(10) assembly had significantly higher amount of Alexa-LEDGF$_{1-326}$ as compared to control or blank group.

Example 4

Live/Dead Cell Count Assay—

Figure 26:
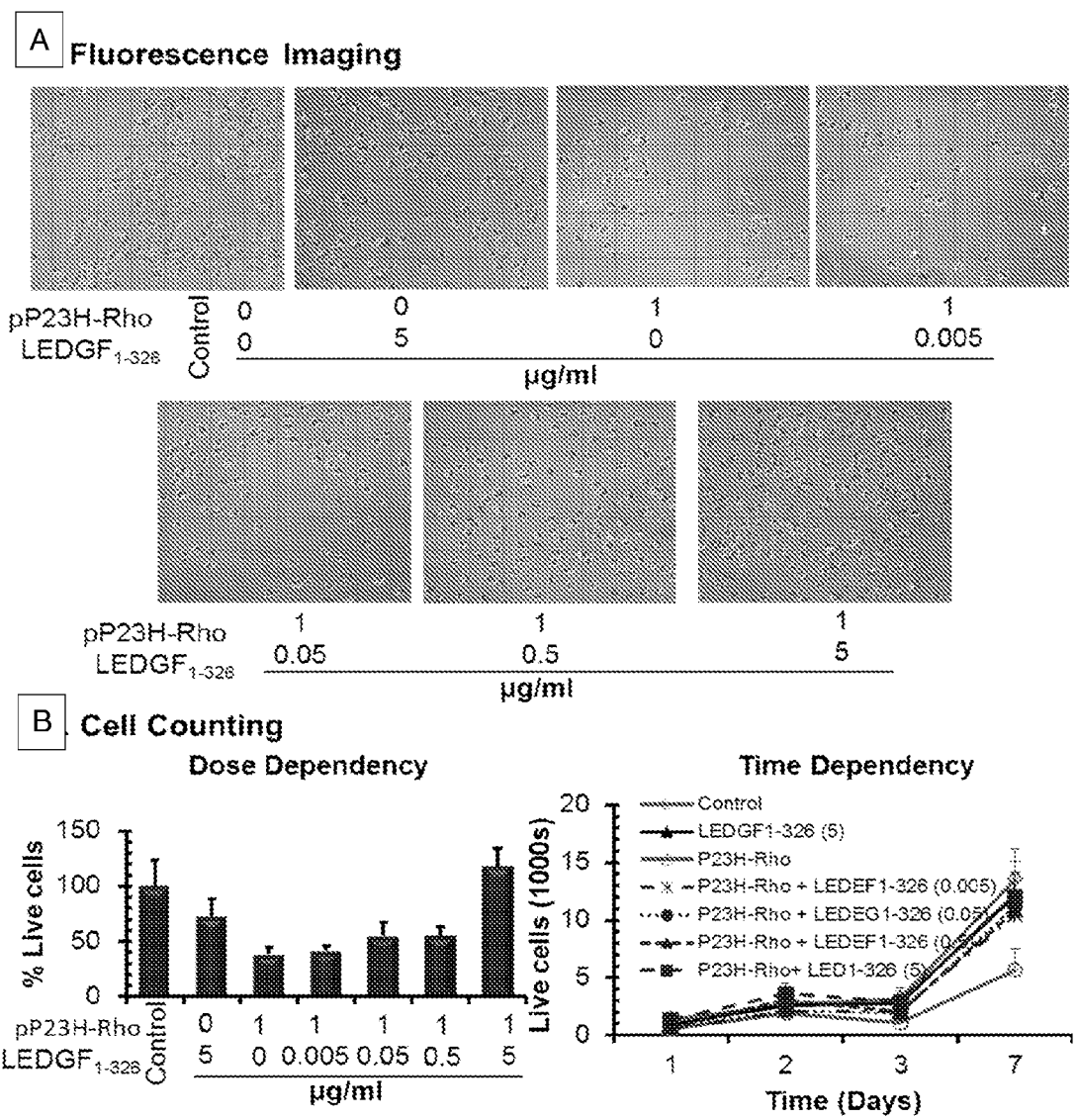
FIGS. 26A-B are A) a set of images of a cell count assay of ARPE-19 cells transfected with LEDGF$_{1-326}$ and B) graphs demonstrating the results of the cell count assay as a function of time and concentration of LEDGF$_{1-326}$.

For cell count assay, 10000 ARPE-19 cells were plated in 96-well plate and incubated for 24 hours. (FIG. 26). After 24 hours, the serum containing medium was aspirated out. The test groups (pP23H-Rho+ LEDGF$_{1-326}$) were transiently transfected with pP23H-Rho plasmid (1 µg/ml) using 1:3 ratio of lipofectamine 2000 (LP-2000) in serum free medium as per manufacturer's protocol. After six hours of transfection, the medium were aspirated out and cells were treated with increasing amount of LEDGF$_{1-326}$. No cells (just the medium), cells with no LP-2000 and cells with LP-2000 were also maintained as control. At the end of LEDGF$_{1-326}$ treatment period, cells were washed with PBS. The cells were labeled with a combination of plasma membrane permeant (Hoechst 33342), a plasma membrane impermeanble molecule (BOBO™ 3), and a nuclear dye (4',6-diamidino-2-phenylindole, dihydrochloride; DAPI). Hoechst 33342 labeled cell nuclei, whereas BOBO™ 3 labeled dying or dead cells. The cells were visualized using Operetta® high content imaging system. Cell count was obtained using automated software tool in the Operetta® instrument. Number and percentage of live cells were calculated by subtracting the dead cell count from "all cell" count. As shown in FIG. 26, LEDGF$_{1-326}$ increases ARPE-19 cell viability.

Imunoblotting:

For immunoblotting CFP tagged P23H-Rho (pP23H-CFP-Rho) was used instead of P23H-Rho for transfection. ARPE-19 cells were plated in 60 mm plates; transfection and drug treatment was up scaled proportionately relative to 96-well plate study. After LEDGF$_{1-326}$ treatment is over, cells were washed once with cold PBS and lysed by sonication in RIPA buffer containing protease inhibitor. Equal amount of supernatant were loaded into SDS-PAGE gel and was immunoblotted for Hsp70, Hsp40, Hsp27, CFP (for P23H-CFP-Rho), and LEDGF$_{1-326}$, and β-actin. Protein bands were visualized using enhanced chemiluminecence ECL™ detection kit (GE Healthcare, Piscataway, N.J.). The observed data indicate that LEDGF$_{1-326}$ is internalized Phagocytic Assay—

Figure 27:
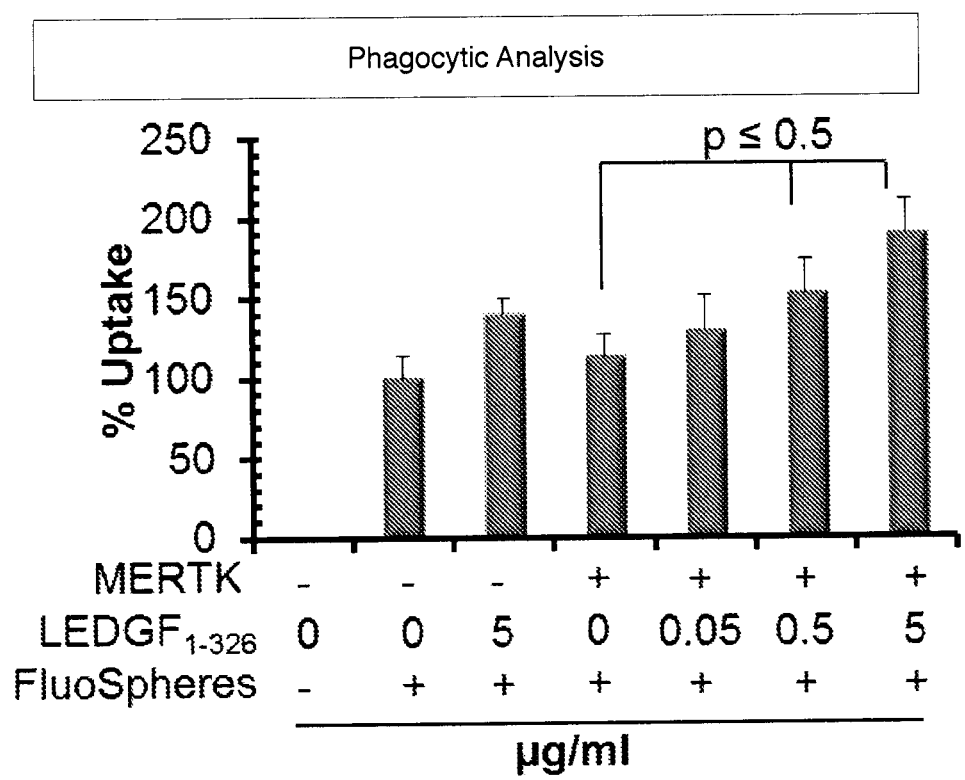
FIG. 27 is a graph demonstrating the results of an assay measuring phagocytic activity and indicating increased phagocytic activity in ARPE-19 cells transfected with LEDGF$_{1-326}$.

ARPE-19 cells were seeded in 24-well plates and transfected with 20 μM/ml of MERTK siRNA (Santa Cruz Biotechnology Inc., Dallas, Tex.), using siRNAtransfecting agent (Santa Cruz Biotechnology Inc., Dallas, Tex.) for 6 hours. The transfecting medium was removed and cells were further incubated in serum free medium for 24 hours. Cells transfected only with the transfecting medium and no MERTK siRNA were maintained as control. Cells were washed once and treated with 0.05, 0.5, or 5 μg/ml of LEDGF$_{1-326}$ for 24 hours and then phagocytosis of 2 μm particles were monitored. Briefly, 100 μg/ml of 2 μm blue FluoSpheres (Life Technologies, Grand Island, N.Y.) was incubated with cells for 3 hours. Thereafter, cells were washed twice with cold PBS pH 7.4, followed by two washes of cold PBS pH 5.0 to remove adherent FluoSpheres. Cells were lysed using 1% Triton-x, and the fluorescence of the particles in the cell lysate was measured using 350 nm excitation and 430 nm emission. Cells transfected with only transfecting agent without siRNA was taken as control for particle uptake. Cells with no particle treatment were used for background fluorescence measurements. As shown in FIG. 27, LEDGF$_{1-326}$ increases phagocytic activity. Decreased phagocytosis of retinal pigment epithelial cells is a hallmark of several retinal diseases including degenerative diseases. LEDGF$_{1-326}$ will be useful in treating diseases with impaired phagocytosis.

Figure 28:
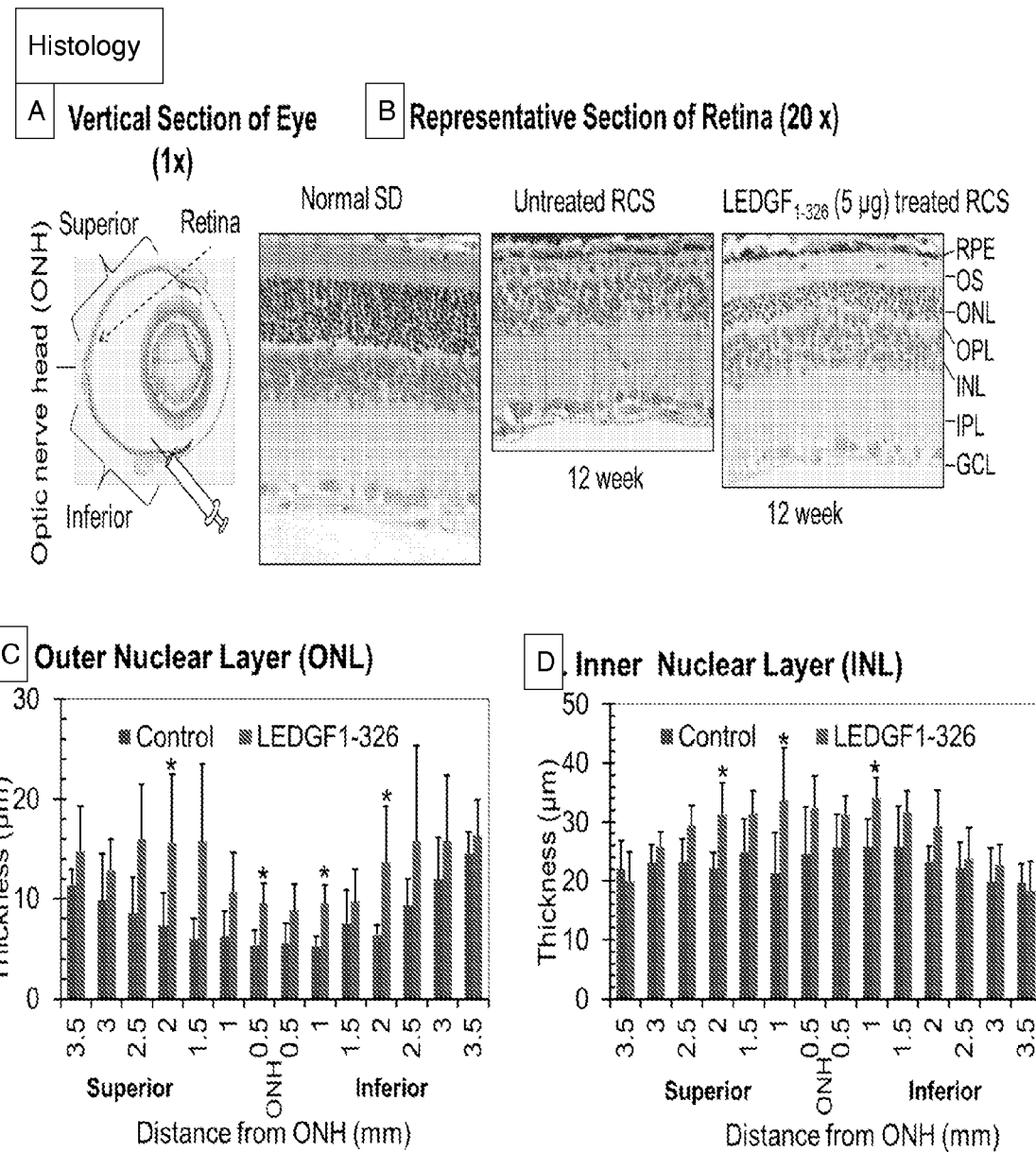
FIGS. 28A-D are a set of images and graphs demonstrating the results of a histological analysis of SD rat eyes injected with LEDGF$_{1-326}$. A) is a graphical depiction of a vertical section of an eye at the site of intravitreal injection. B) is a set of images of cross sections of normal SD, untreated RCS, and LEDGF$_{1-326}$ treated RCS retinas. C) and D) are graphs depicting the measured thickness of outer and inner nuclear layers of the eye in control and LEDGF$_{1-326}$ treated retinas respectively.

Histology:

At the end of the study i.e. on 12$^{th}$ week, eyes were enucleated after ERG measurements and fixed in Davidson's fixative (2% of 37-40% formaldehyde, 35% ethanol, 10% glacial acetic acid, and 53% distilled water) for 24 hours at room temperature. The eyes were then stored in 70% ethanol for subsequent serial dehydration and embedment in paraffin. Three vertical sections of 6 lam thick were cut from the nasal to the temporal side at the optical nerve (500 μm apart) on a standard microtome. Gross retinal morphology was assessed by light microscope following hematoxylin/eosin staining of tissue sections. The thickness of outer nuclear layer (ONL) and inner nuclear layer (INL) was measured methodically using Aperio ImageScope software v11.1.2.760. Since the photoreceptor cell protection may be uneven across the retina, every 500 μm from the superior edge to the inferior edge in each section was analyzed and average of three sections was done for each point. Data represent average of three eyes. As shown in FIG. 28, LEDGF$_{1-326}$ delays both retinal nuclear photoreceptors loss.

Figure 29:
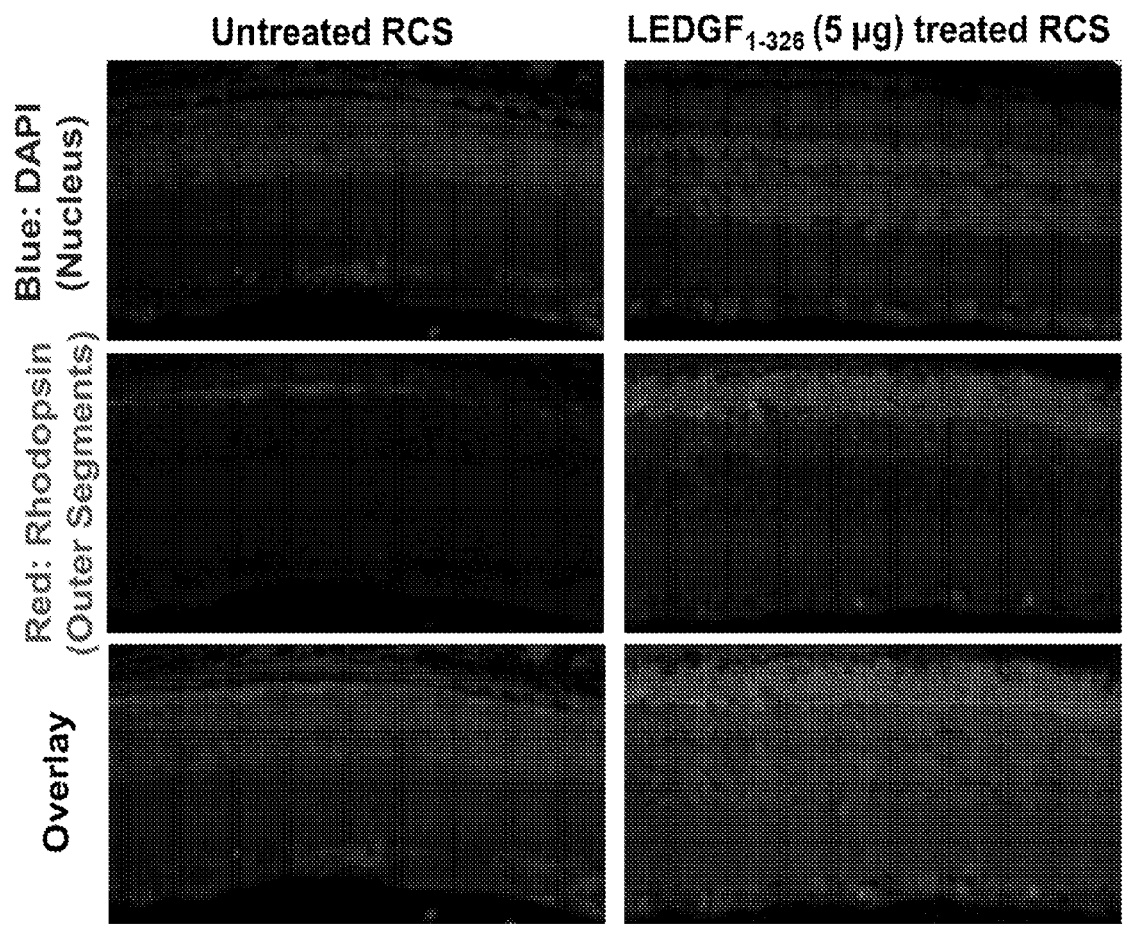
FIG. 29 is panel of immunofluorescence images of control and LEDGF$_{1-326}$ treated rat SD retinas.

Immunofluorescence:

For immunofluorescence, after removal of paraffin, eye sections were processed through the following sequential steps at room temperature, unless otherwise indicated. Antigen was retrieved by boiling the sections at 80° C. for 15 min. After blocking the nonspecific binding, sections were incubated with mouse anti-rhodopsin (1D4) primary antibody at 4° C. overnight followed by 30 min incubation with Alexa Fluor® 594 conjugated donkey anti-mouse IgG and DAPI. Finally, eye sections were washed and mounted by Supermount H (Biogenex, San Ramon, Calif.) mounting medium to prevent rapid loss of fluorescence. The fluorescence was visualized using confocal microscope (Nikon Eclipse C1) at 20× optical zoom. The excitation-emission wavelengths used for DAPI and, Alexa Fluor were 408-450/35, and 637-605/75 nm, respectively. Images were captured using Nikon EZ-C1 software version 3.40. As show in FIG. 29, LEDGF$_{1-326}$ delays rod outer segment loss.

Example 5

In Vitro Cumulative Release of His-LEDGF$_{1-326}$

Figure 30:
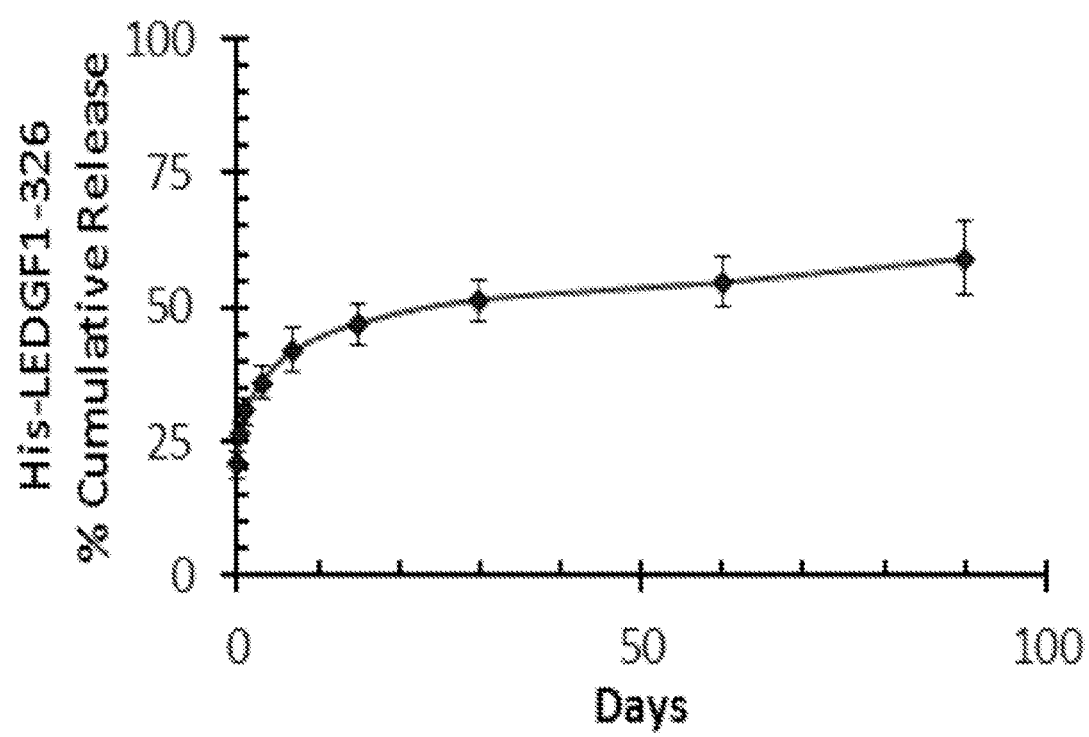
FIG. 30 is a graph showing the cumulative release of His-LEDGF$_{1-326}$ from example PinP compositions FIG. 31 are graphs showing the results of non-invasive ocular fluorophotometry after intravitreal injection in rat eyes with Alexa-His-LEDGF$_{1-326}$.

His-LEDGF$_{1-326}$ encapsulated NPinPMP were evaluated for in vitro release in PBS pH 7.4. Particles (2-3 mg) were weighed and dispersed in 1 ml of PBS pH 7.4 and incubated at 37° C. under shaking at 200 rpm (Max Q shaker incubator). At predetermined time points the suspended particles were centrifuged at 13,000 g for 15 min and the supernatant was collected. The pellet comprising particles was resuspended in 1 ml of fresh PBS pH 7.4 and incubated. The His-LEDGF$_{1-326}$ content in the samples was estimated using micro BCA assay as per the manufacturer's instructions (Pierce Biotechnology, IL, USA). The in vitro cumulative data showed the sustained release of His-LEDGF$_{1-326}$ from NPinPMP. As shown in FIG. 30, a cumulative 60% release of His-LEDGF$_{1-326}$ was observed by the end of 3 months.

In Vivo Delivery of his-LEDGF$_{1-326}$ in Rats

In vivo delivery of His-LEDGF$_{1-326}$ was evaluated following intravitreal administration of Alexa Fluor 488 conjugated His-LEDGF$_{1-326}$ in NPinPMP in a rat model. No unlabeled LEDGF$_{1-326}$ was used in the NPinPMP. The rat eyes were injected with Alexa-His-LEDGF$_{1-326}$ encapsulated NPinPMP (6.0 μg of His-LEDGF$_{1-326}$/5 μl) and as a control Alexa-His-LEDGF$_{1-326}$=at equivalent concentration (1.5 μg labeled protein and 4.5 μg unlabeled protein/5 μl) was injected. This ratio allowed us to start with a similar fluorescence intensity for both groups to begin with. Ocular fluorescence due to the release of Alexa-His-LEDGF$_{1-326}$ was monitored periodically using Fluorotron Master™ (Ocumetrics, Calif., USA) until the fluorescence reached the lower detection limit or baseline. Baseline fluorescence values of eyes were monitored before injecting the formulations. At each time point, three fluorometric scans were taken and mean value was used. Standard curve for Alexa-His-LEDGF$_{1-326}$ at different concentrations was obtained using a cuvette and ocular flurophotometry with a rat lens adapter. The standard curve was used to convert fluorescein equivalent concentrations provided by fluorophotometer to actual Alexa-His-LEDGF$_{1-326}$ concentration.

Figure 31:
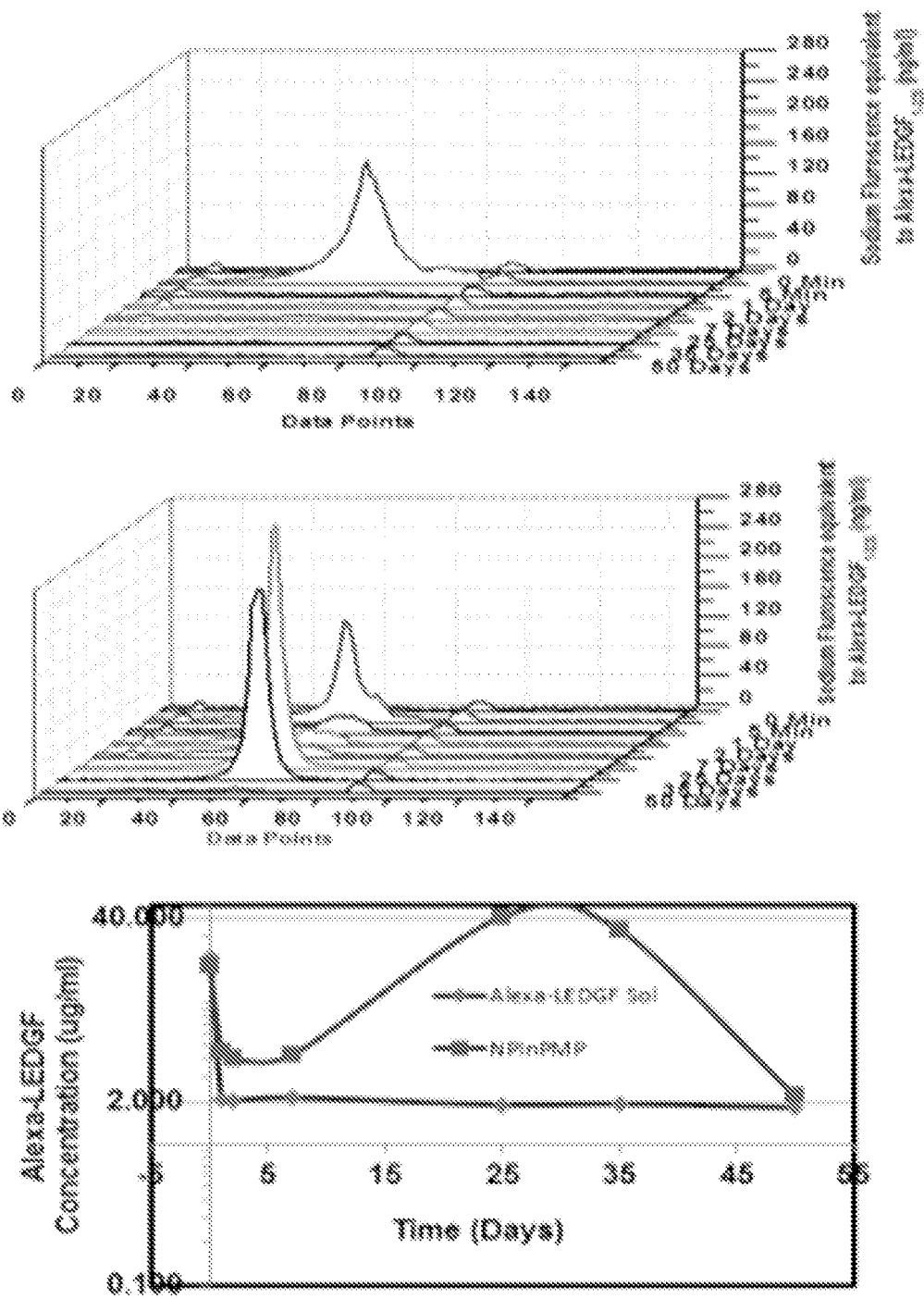

After intravitreal injection of Alexa-His-LEDGF$_{1-326}$ encapsulating NPinPMP, and soluble Alexa-His-LEDGF$_{1-326}$, the concentrations distribution of His-LEDGF$_{1-326}$ along the eye optical axis was determined indirectly by measuring the alexa fluorescence intensity distribution (equivalent of sodium fluresciene concentration) curve along axial planes, indicated as data points in an anterior to posterior direction. The fluorescence scans revealed sustained delivery of Alexa-His-LEDGF$_{1-326}$ from NPinPMP compared to solution. Fluorescein equivalent concentrations reported by Fluorotron Master were converted to Alexa-His-LEDGF$_{1-326}$ concentrations. The Alexa-His-LEDGF$_{1-326}$ concentration in the vitreous region from solution and NPinPMP group at different time points was plotted. Only the concentrations of the labeled bevacizumab are reported. Before intravitreal injection, the baseline fluorescence readings of normal eyes were taken and the baseline fluorescence concentration was found to be 2.03 μg/ml. As show in FIG. 31, the Alexa-His-LEDGF$_{1-326}$ solution injected group showed Alexa-His-LEDGF$_{1-326}$ concentration of 2.02 μg/ml on day 1 indicating rapid elimination from vitreous region. In NPinPMP injected group the Alexa-His-LEDGF$_{1-326}$ the initial concentration in the vitreous was found to be 18.23 μg/ml and the Alexa-His-LEDGF$_{1-326}$ concentration above the baseline was maintained until 35th day and reached normal base line levels by end of 50 days. The observed data indicate the ability to achieve sustained in vivo release of Alexa-His-LEDGF$_{1-326}$ from an exemplary PinP composition.

---

What is claimed is:

1. A purified peptide which is a fragment of full-length lens epithelium derived growth factor (LEDGF), selected from the group consisting of:
   (a) a first peptide consisting essentially of N-terminal amino acids of (LEDGF) wherein the N-terminal amino acids are amino acids 1-326 (LEDGF$_{1-326}$) (SEQ ID NO: 2),
   (b) a second peptide having the N-terminal stress related binding domain of the full-length LEDGF, wherein the second peptide has an amino acid sequence with at least 80%, at least 85%, at least 90%, or at least 95% sequence identity to the amino acid sequence of LEDGF$_{1-326}$ (SEQ ID NO: 2),
   (c) a third peptide having the N-terminal stress related binding domain and TAT binding domain of the full-length LEDGF, wherein third peptide has an amino acid sequence with at least 80%, at least 85%, at least 90%, or at least 95% sequence identity to the amino acid sequence of LEDGF$_{1-326}$ (SEQ ID NO: 2), and
   (d) a fourth peptide having more than said amino acids 1-326, wherein the purified peptide does not show a decrease in biological activity or stability during biosynthesis or production and purification relative to the full-length LEDGF.

2. The purified peptide of claim 1, wherein the peptide further comprises a TAT binding domain.

3. The purified peptide of claim 1, wherein the peptide is LEDGF$_{1-326}$ (SEQ ID NO: 2).

4. The purified peptide of claim 1, wherein the peptide has at least 95% sequence identity to SEQ ID NO: 2.

5. A composition comprising the purified peptide of claim 1.

6. The composition of claim 5, further comprising a pharmaceutical carrier, diluent, excipient or combination thereof.

7. The composition of claim 5, wherein the purified peptide is bound to or associated with a colloidal metal nanoparticle.

8. The composition of claim 5, wherein the purified peptide is bound to, or encapsulated in, an inner particle, and wherein the inner particle is loaded in a porous outer particle.

9. The composition of claim 8, wherein the inner particle is made from a particle material that does not expand in supercritical carbon dioxide.

10. The composition of claim 8, wherein the inner particle material is a polymeric material.

11. The composition of claim 8, wherein the outer particles are made from a particle material that expands in supercritical carbon dioxide.

12. The composition of claim 11, wherein the outer particle is a polymeric material.

13. A method of treating a protein aggregation-mediated disease comprising administering to a patient in need thereof a composition comprising a purified peptide, wherein the peptide is $LEDGF_{1-326}$ (SEQ ID NO: 2).

14. The method of claim 13, wherein the aggregation-mediated disease is an ocular disease.

15. The method of claim 14, wherein the ocular disease is retinal degeneration disease.

16. The method of claim 15, wherein the retinal degeneration disease is age related macular degeneration (AMD), or retinitis pigmentosa (RP).

17. A method of reducing protein aggregation in a protein aggregation-mediated disease comprising administering to a patient in need thereof a composition comprising a purified peptide wherein the peptide is $LEDGF_{1-326}$ (SEQ ID NO: 2).

18. The method of claim 17, wherein protein aggregation is caused by endoplasmic reticulum stress, oxidative stress, or both.

19. The method of claim 17, wherein the patient has retinal degeneration disease.

20. The purified peptide of claim 1, wherein (d) is His-tagged $LEDGF_{1-326}$ (His-$LEDGF_{1-326}$) (SEQ ID NO.1).

21. The composition of claim 7, wherein the colloidal metal nanoparticle selected from the group consisting of: gold, silver, aluminum, ruthenium, zinc, iron, nickel, calcium, lithium, sodium, magnesium, potassium, scandium, titanium, vanadium, chromium, manganese, cobalt, copper, gallium, strontium, niobium, molybdenum, palladium, indium, tin, tungsten, rhenium, platinum and gadolinum colloidal metal nanoparticle.

22. The method of claim 17, where in the aggregation-mediated disease is a neurodegenerative disease.

23. The method of claim 19, wherein the retinal degeneration disease is age related macular degeneration (AMD), or retinitis pigmentosa (RP).

24. The method of claim 17, wherein the patient has a neurodegenerative disease.

25. The method of claim 24, wherein the neurodegenerative disease is Alzheimer's disease (AD), Parkinson's disease (PD), Huntington's disease (HD), amyotrophic lateral sclerosis, or a prion disease.

26. The method of claim 23, wherein the neurodegenerative disease is Alzheimer's disease (AD), Parkinson's disease (PD), Huntington's disease (HD), amyotrophic lateral sclerosis, or a prion disease.

* * * * *

SEQUENCE LISTING

```
<160> NUMBER OF SEQ ID NOS: 6

<210> SEQ ID NO 1
<211> LENGTH: 360
<212> TYPE: PRT
<213> ORGANISM: Artificial Sequence
<220> FEATURE:
<223> OTHER INFORMATION: Homo sapiens

<400> SEQUENCE: 1

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Met Thr Arg Asp Phe Lys Pro Gly Asp Leu Ile Phe Ala Lys
        35                  40                  45

Met Lys Gly Tyr Pro His Trp Pro Ala Arg Val Asp Glu Val Pro Asp
    50                  55                  60

Gly Ala Val Lys Pro Pro Thr Asn Lys Leu Pro Ile Phe Phe Phe Gly
65                  70                  75                  80

Thr His Glu Thr Ala Phe Leu Gly Pro Lys Asp Ile Phe Pro Tyr Ser
                85                  90                  95

Glu Asn Lys Glu Lys Tyr Gly Lys Pro Asn Lys Arg Lys Gly Phe Asn
            100                 105                 110

Glu Gly Leu Trp Glu Ile Asp Asn Asn Pro Lys Val Lys Phe Ser Ser
        115                 120                 125

Gln Gln Ala Ala Thr Lys Gln Ser Asn Ala Ser Ser Asp Val Glu Val
    130                 135                 140

Glu Glu Lys Glu Thr Ser Val Ser Lys Glu Asp Thr Asp His Glu Glu
145                 150                 155                 160

Lys Ala Ser Asn Glu Asp Val Thr Lys Ala Val Asp Ile Thr Thr Pro
                165                 170                 175

Lys Ala Ala Arg Arg Gly Arg Lys Arg Lys Ala Glu Lys Gln Val Glu
            180                 185                 190

Thr Glu Glu Ala Gly Val Val Thr Thr Ala Thr Ala Ser Val Asn Leu
        195                 200                 205

Lys Val Ser Pro Lys Arg Gly Arg Pro Ala Ala Thr Glu Val Lys Ile
    210                 215                 220

Pro Lys Pro Arg Gly Arg Pro Lys Met Val Lys Gln Pro Cys Pro Ser
225                 230                 235                 240

Glu Ser Asp Ile Ile Thr Glu Glu Asp Lys Ser Lys Lys Lys Gly Gln
                245                 250                 255

Glu Glu Lys Gln Pro Lys Lys Gln Pro Lys Lys Asp Glu Glu Gly Gln
            260                 265                 270

Lys Glu Glu Asp Lys Pro Arg Lys Glu Pro Asp Lys Lys Glu Gly Lys
        275                 280                 285

Lys Glu Val Glu Ser Lys Arg Lys Asn Leu Ala Lys Thr Gly Val Thr
    290                 295                 300
```

```
Ser Thr Ser Asp Ser Glu Glu Gly Asp Asp Gln Glu Gly Glu Lys
305                 310                 315                 320

Lys Arg Lys Gly Gly Arg Asn Phe Gln Thr Ala His Arg Arg Asn Met
            325                 330                 335

Leu Lys Gly Gln His Glu Lys Glu Ala Ala Asp Arg Lys Arg Lys Gln
        340                 345                 350

Glu Glu Gln Met Glu Thr Glu Gln
        355                 360

<210> SEQ ID NO 2
<211> LENGTH: 326
<212> TYPE: PRT
<213> ORGANISM: Artificial Sequence
<220> FEATURE:
<223> OTHER INFORMATION: Homo sapiens

<400> SEQUENCE: 2

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205

Asp Ile Ile Thr Glu Glu Asp Lys Ser Lys Lys Lys Gly Gln Glu Glu
    210                 215                 220

Lys Gln Pro Lys Lys Gln Pro Lys Lys Asp Glu Glu Gly Gln Lys Glu
225                 230                 235                 240

Glu Asp Lys Pro Arg Lys Glu Pro Asp Lys Lys Glu Gly Lys Lys Glu
                245                 250                 255

Val Glu Ser Lys Arg Lys Asn Leu Ala Lys Thr Gly Val Thr Ser Thr
            260                 265                 270

Ser Asp Ser Glu Glu Glu Gly Asp Asp Gln Glu Gly Glu Lys Lys Arg
        275                 280                 285

Lys Gly Gly Arg Asn Phe Gln Thr Ala His Arg Arg Asn Met Leu Lys
    290                 295                 300
```

```
Gly Gln His Glu Lys Glu Ala Ala Asp Arg Lys Arg Lys Gln Glu Glu
305                 310                 315                 320

Gln Met Glu Thr Glu Gln
                325

<210> SEQ ID NO 3
<211> LENGTH: 31
<212> TYPE: DNA
<213> ORGANISM: Artificial Sequence
<220> FEATURE:
<223> OTHER INFORMATION: Synthetic primer

<400> SEQUENCE: 3
agtagtggat ccatgactcg cgatttcaaa c                               31

<210> SEQ ID NO 4
<211> LENGTH: 36
<212> TYPE: DNA
<213> ORGANISM: Artificial Sequence
<220> FEATURE:
<223> OTHER INFORMATION: Synthetic Primer

<400> SEQUENCE: 4
aataataagc tttcactgct cagtttccat ttgttc                          36

<210> SEQ ID NO 5
<211> LENGTH: 38
<212> TYPE: DNA
<213> ORGANISM: Artificial Sequence
<220> FEATURE:
<223> OTHER INFORMATION: Synthetic Primer

<400> SEQUENCE: 5
agcaagccat gggcatgact cgcgatttca aacctgga                        38

<210> SEQ ID NO 6
<211> LENGTH: 39
<212> TYPE: DNA
<213> ORGANISM: Artificial Sequence
<220> FEATURE:
<223> OTHER INFORMATION: Synthetic Primer

<400> SEQUENCE: 6
agcaagaagc ttctactgct cagtttccat ttgttcctc                       39
```